(12) United States Patent
Kirst

(10) Patent No.: US 9,650,646 B2
(45) Date of Patent: May 16, 2017

(54) MATERIALS AND METHODS TO INCREASE PLANT GROWTH AND YIELD

(71) Applicant: University of Florida Research Foundation, Inc., Gainesville, FL (US)

(72) Inventor: Matias Kirst, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 110 days.

(21) Appl. No.: 14/329,225

(22) Filed: Jul. 11, 2014

(65) Prior Publication Data

US 2015/0007366 A1 Jan. 1, 2015

Related U.S. Application Data

(63) Continuation-in-part of application No. 14/152,865, filed on Jan. 10, 2014, now Pat. No. 9,133,470.

(60) Provisional application No. 61/751,648, filed on Jan. 11, 2013.

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01); *C12N 15/8261* (2013.01)

(58) Field of Classification Search
None
See application file for complete search history.

(56) References Cited

U.S. PATENT DOCUMENTS

| | | |
|---|---|---|
| 5,023,179 A | 6/1991 | Lam et al. |
| 5,034,322 A | 7/1991 | Fraley et al. |
| 5,106,739 A | 4/1992 | Comai et al. |
| 5,164,316 A | 11/1992 | McPherson et al. |
| 5,196,525 A | 3/1993 | McPherson et al. |
| 5,256,558 A | 10/1993 | Coruzzi et al. |
| 5,322,938 A | 6/1994 | McPherson et al. |
| 5,359,142 A | 10/1994 | McPherson et al. |
| 5,424,200 A | 6/1995 | McPherson et al. |
| 5,625,136 A | 4/1997 | Koziel et al. |
| 6,831,208 B1 | 12/2004 | Chiang et al. |
| 7,723,575 B2 | 5/2010 | Alibhai et al. |
| 2004/0031072 A1 | 2/2004 | La Rosa et al. |
| 2008/0196125 A1 | 8/2008 | Papes et al. |
| 2009/0031441 A1 | 1/2009 | Matsuoka et al. |
| 2011/0167514 A1 | 7/2011 | Brover et al. |
| 2011/0214207 A1 | 9/2011 | Frankard et al. |
| 2012/0180165 A1 | 7/2012 | Hatzfeld et al. |
| 2015/0368657 A1 | 12/2015 | Kirst |

FOREIGN PATENT DOCUMENTS

WO WO 2013/026740 2/2013

OTHER PUBLICATIONS

Zhang, Curr Opin Plant Biol 6:430-40 (2003).*
Guo et al., Proc Natl Acad Sci USA 101:9205-10 (2004).*
Jones et al., Plant J 26(2):205-16 (2001).*
Mitsuda et al., Plant Cell 19:270-80 (2007).*
Olsen et al., Trends Plant Sci 10(2):79-87 (2005).*
Whisstock & Lesk, Q Rev Biophys. 36(3):307-40 (2003).*
Hill & Preiss, Biochem Biophys Res Commun 244(2):573-77 (1998).*
U.S. Appl. No. 14/822,782, filed Aug. 10, 2015, Kirst.
Albert et al., "Site-specific integration of DNA into wild-type and mutant *lox* sites placed in the plant genome," *The Plant Journal* 7:649-659, 1995.
Benfey et al., "Tissue-specific expression from CaMV 35S enhancer subdomains in early stages of plant development," *EMBO J* 9:1677-1684, 1990.
Chen et al., "Rice α-amylase transcriptional enhancers direct multiple mode regulation of promoters in transgenic rice," *Journal of Biological Chemistry* 277:13641-13649, 2002.
Chua et al. "The transcriptional enhancer of the pea plastocyanin gene associates with the nuclear matrix and regulates gene expression through histone acetylation," *Plant Cell* 15:1468-1479, 2003.
Drost et al., "Diversification in the genetic architecture of gene expression and transcriptional networks in organ differentiation of Populus," *PNAS USA* 107(18):8492-7, 2010.
Feng, et al., "Efficient genome editing in plants using a CRIPR/Cas system," *Cell Research* 23:1229-1232, 2013.
Guo et al., "Protein tolerance to random amino acid change," *PNAS USA* 101:9205-9210, 2004.
International Search Report and Written Opinion issued in PCT/US2014/011128, dated Mar. 24, 2014.
Li et al., "Site-Specific Integration of Transgenes in Soybean via Recombinase-Mediated DNA Cassette Exchange," *Plant Physiology* 151:1087-1095, 2009.
Lyznik et al., "Application of Site-Specific Recombination Systems for Targeted Modification of Plant Genomes," *Transgenic Plant J* 1:1-9, 2007.
Martinez De Alba et al., "The miRNA pathway limits AGO1 availability during siRNA-mediated PTGS defense against exogenous RNA," *Nucleic Acids Research* 39:9339-9344, 2011.
Novaes et al., "Quantitative genetic analysis of biomass and wood chemistry of Populus under different nitrogen levels," *New Phytol* 182(4):878-90, 2009.

(Continued)

*Primary Examiner* — Amjad Abraham
*Assistant Examiner* — Russell Boggs
(74) *Attorney, Agent, or Firm* — Dentons US LLP

(57) ABSTRACT

The present invention relates to materials and methods for modulating growth rates, yield, and/or resistance to drought conditions in plants. In one embodiment, a method of the invention comprises increasing expression of an hc1 gene (or a homolog thereof that provides for substantially the same activity), or increasing expression or activity of the protein encoded by an hc1 gene thereof, in a plant, wherein expression of the hc1 gene or expression or activity of the protein encoded by an hc1 gene results in increased growth rate, yield, and/or drought resistance in the plant.

30 Claims, 9 Drawing Sheets

(56) References Cited

OTHER PUBLICATIONS

Puchta, "Gene replacement by homologous recombination in plants," *Plant Mol Biol* 48:173-182, 2002.
Quesada et al., "Comparative analysis of the transcriptomes of Populus trichocarpa and Arabidopsis thaliana suggests extensive evolution of gene expression regulation in angiosperms," *New Phytol* 180(2):408-20, 2008.
Ribeiro et al., "HC Regulates Growth and Hydraulic Conductivity in Poplar," *Plant & Animal Genome XXI*, Abstract, 2013.
Ribeiro et al., "'Unknown Function' Gene *HC1* Regulates Growth and Hydraulic Conductivity in Poplar Trees," *Plant & Animal Genome* XXII, Abstract, 2014.
Sade et al., "The Role of Tobacco Aquaporin 1 in Improving Water Use Efficiency, Hydraulic Conductivity, and Yield Production Under Salt Stress," *Plant Physiol* 152(1):245-254, 2009.
Tyree et al., Xylem Structure and the Ascent of Sap., 2nd ed. New York, NY: Springer-Verlag, 2002.
Whisstock et al., "Prediction of protein function from protein sequence structure," *Quarterly Reviews of Biophysics* 36:307-340, 2003.
Wright et al., "High-frequency homologous recombination in plants mediated by zinc-finger nucleases," *Plant J* 44:693-705, 2005.
Zhang et al., "Overexpression analysis of plant transcription factors," *Current Opinion in Plant Biology* 6:430-440, 2003.
"Straight into the Cotton Genome," *Bayer Research* 24:68-71, 2012.
Cai et al., "Targeted transgene integration in plant cells using designed zinc finger nucleases," *Plant Molecular Biology* 69:699-709, 2009.
Chudalayandi, "Enhancer Trapping in Plants," in Plant Chromosome Engineering: Methods and Protocols, James A. Birchler (ed.), *Methods Molecular Biology* 701:285-300, 2011.
Lieberman-Lazarovich et al., "Homologous recombination in plants: an antireview," *Methods in Molecular Biology* 701:51-65, 2011.
Podevin et al., "Site-directed nucleases: a paradigm shift in predictable, knowledge-based plant breeding," *Trends Biotech* 31(6):375-383, 2013.
Wei et al., "TALEN or Cas9—Rapid, Efficient and Specific Choices for Genome Modifications," *J Gen Genomics* 40(6):281-289, 2013.
Yau et al. "Method for Bxb1-Mediated Site-Specific Integration In Planta," *Methods in Molecular Biology* 701:147-166, 2011.
Zhang et al., "Transcription activator-like effector nucleases enable efficient plant genome engineering," *Plant Physiol* 161:20-27, 2012.
USPTO: Non-Final Office Action regarding U.S. Appl. No. 14/822,782, dated Nov. 18, 2016.

\* cited by examiner

SEQUENCE LISTING

<160> NUMBER OF SEQ ID NOS: 105

<210> SEQ ID NO 1
<211> LENGTH: 228
<212> TYPE: DNA
<213> ORGANISM: Populus trichocarpa

<400> SEQUENCE: 1

```
atgtcggatt ggggaccggt atttgtggcg gtggtgctgt ttatactctt aacaccaggt    60
ttgctgattc agataccggg tcgtcagcga ttagttgagt ttggcaactt tcagaccagt   120
ggagtttcca tactggttca ctccatcctc tactttgctc tcatttgcat tttcttgtta   180
gctgttggtg tccacgtgtg ctctttgtgt acaccatcta tgcttgat                228
```

<210> SEQ ID NO 2
<211> LENGTH: 76
<212> TYPE: PRT
<213> ORGANISM: Populus trichocarpa

<400> SEQUENCE: 2

```
Met Ser Asp Trp Gly Pro Val Phe Val Ala Val Val Leu Phe Ile Leu
1               5                   10                  15

Leu Thr Pro Gly Leu Leu Ile Gln Ile Pro Gly Arg Gln Arg Leu Val
            20                  25                  30

Glu Phe Gly Asn Phe Gln Thr Ser Gly Val Ser Ile Leu Val His Ser
        35                  40                  45

Ile Leu Tyr Phe Ala Leu Ile Cys Ile Phe Leu Leu Ala Val Gly Val
    50                  55                  60

His Val Cys Ser Leu Cys Thr Pro Ser Met Leu Asp
65                  70                  75
```

<210> SEQ ID NO 3
<211> LENGTH: 773
<212> TYPE: DNA
<213> ORGANISM: Populus trichocarpa

<400> SEQUENCE: 3

```
atgtcggatt ggggaccggt atttgtggcg gtggtgctgt ttatactctt aacaccaggt    60
ttgctgattc agataccggg tcgtcagcga ttagttgagt ttggcaactt tcagaccagt   120
ggagtttcca tactggttca ctccatcctc tactttgctc tcatttgcat tttcttgtta   180
gctgttggtg tccacgtgta tgtaggttca tagccttcga atgctgatct gcctgtcaca   240
cagggatgtg agacttaatc gttctgattt tcttgaattg tgataactct gcttttcttt   300
tcccatttat gatagatgtt ttgaaactga ttcgtgtagc aaatctttgt acttgatttc   360
tttagttaaa tctaatgcag ttctgtcttt gctttgtggt ttcaagttgg aattcttggc   420
taaatcaatt aacagacgag actggattta cttgcagagc aacttcataa acatgacaca   480
tatttcaagc acaatggatt gtatatttag gaagcactac gcaccatagg ttggcttttg   540
cctgtcactg aagaactgtt gctagtgaga gagaagcaaa aatttaggtt gatgatgact   600 agggggtaact tgaatgaaag tggattaaaa agggttggag gatctggaat ctttgcataa   660
gcacggccag tgaagataga gactgaggga tcgcaaggca agaaaagtta aggaacata    720 tcaattttct tcatgctagg tgctctttgt gtacaccatc tatgcttgat tga           773
```

<210> SEQ ID NO 4
<211> LENGTH: 70
<212> TYPE: PRT
<213> ORGANISM: Populus trichocarpa

<400> SEQUENCE: 4

```
Met Ser Asp Trp Gly Pro Val Phe Val Ala Val Val Leu Phe Ile Leu
1               5                   10                  15

Leu Thr Pro Gly Leu Leu Ile Gln Ile Pro Gly Arg Gln Arg Leu Val
            20                  25                  30
```

```
Glu Phe Gly Asn Phe Gln Thr Ser Gly Val Ser Ile Leu Val His Ser
            35                  40                  45

Ile Leu Tyr Phe Ala Leu Ile Cys Ile Phe Leu Leu Ala Val Gly Val
 50                  55                  60

His Val Tyr Val Gly Ser
 65                  70

<210> SEQ ID NO 5
<211> LENGTH: 5
<212> TYPE: PRT
<213> ORGANISM: Populus trichocarpa

<400> SEQUENCE: 5

Leu Thr Pro Gly Leu
 1               5

<210> SEQ ID NO 6
<211> LENGTH: 12
<212> TYPE: PRT
<213> ORGANISM: Populus trichocarpa

<400> SEQUENCE: 6

Gly Asn Phe Gln Thr Ser Gly Val Ser Ile Leu Val
 1               5                  10

<210> SEQ ID NO 7
<211> LENGTH: 76
<212> TYPE: PRT
<213> ORGANISM: Populus trichocarpa

<400> SEQUENCE: 7

Met Ser Asp Trp Gly Pro Val Phe Val Ala Val Val Leu Phe Ile Leu
 1               5                  10                  15

Leu Thr Pro Gly Leu Leu Ile Gln Ile Pro Gly Arg Gln Arg Leu Val
                20                  25                  30

Glu Phe Gly Asn Phe Gln Thr Ser Gly Val Ser Ile Leu Val His Ser
            35                  40                  45

Ile Leu Tyr Phe Ala Leu Ile Cys Ile Phe Leu Leu Ala Val Gly Val
 50                  55                  60

His Val Cys Ser Leu Cys Thr Pro Ser Met Leu Asp
 65                  70                  75

<210> SEQ ID NO 8
<211> LENGTH: 70
<212> TYPE: PRT
<213> ORGANISM: Morus notabilis

<400> SEQUENCE: 8

Met Ser Asp Trp Gly Pro Val Phe Val Ala Val Val Leu Phe Ile Leu
 1               5                  10                  15

Leu Thr Pro Gly Leu Leu Ile Gln Ile Pro Gly Lys Ser Arg Met Ile
                20                  25                  30

Glu Tyr Gly Asn Phe Gln Thr Ser Gly Val Ser Ile Leu Val His Ser
            35                  40                  45

Val Leu Tyr Phe Ala Leu Ile Cys Ile Phe Leu Leu Ala Ile Gly Val
 50                  55                  60

His Met Tyr Leu Gly Ser
 65                  70

<210> SEQ ID NO 9
```

<211> LENGTH: 70
<212> TYPE: PRT
<213> ORGANISM: Theobroma cacao

<400> SEQUENCE: 9

Met Ser Asp Trp Gly Pro Val Phe Val Ala Val Val Leu Phe Ile Leu
1               5                   10                  15

Leu Thr Pro Gly Leu Leu Ile Gln Val Pro Gly Lys Ser Arg Phe Ile
            20                  25                  30

Glu Phe Gly Asn Phe Gln Thr Ser Gly Leu Ser Ile Leu Val His Ser
        35                  40                  45

Ile Ile Tyr Phe Ala Leu Ile Cys Ile Phe Leu Leu Ala Val Gly Val
    50                  55                  60

His Met Tyr Val Gly Ser
65                  70

<210> SEQ ID NO 10
<211> LENGTH: 70
<212> TYPE: PRT
<213> ORGANISM: Populus trichocarpa

<400> SEQUENCE: 10

Met Ser Asp Trp Gly Pro Val Phe Val Ala Val Val Leu Phe Ile Leu
1               5                   10                  15

Leu Thr Pro Gly Leu Leu Ile Gln Met Pro Gly His His Arg Phe Ile
            20                  25                  30

Glu Phe Gly Asn Phe Lys Thr Ser Gly Val Ser Ile Leu Val His Ser
        35                  40                  45

Ile Leu Tyr Phe Ala Leu Ile Cys Ile Phe Leu Leu Ala Val Gly Val
    50                  55                  60

His Met Tyr Val Gly Ser
65                  70

<210> SEQ ID NO 11
<211> LENGTH: 70
<212> TYPE: PRT
<213> ORGANISM: Eucalyptus grandis

<400> SEQUENCE: 11

Met Ser Asp Trp Gly Pro Val Phe Val Ala Met Val Leu Phe Val Leu
1               5                   10                  15

Leu Thr Pro Gly Leu Leu Ile Gln Ile Pro Gly Lys His Arg Phe Ile
            20                  25                  30

Glu Phe Gly Asn Phe Gln Thr Ser Gly Ala Ser Val Leu Val His Ser
        35                  40                  45

Ile Leu Tyr Phe Ala Leu Val Cys Ile Phe Leu Leu Ala Val Gly Val
    50                  55                  60

His Val Tyr Ile Gly Ser
65                  70

<210> SEQ ID NO 12
<211> LENGTH: 70
<212> TYPE: PRT
<213> ORGANISM: Glycine max

<400> SEQUENCE: 12

Met Ala Asp Trp Gly Pro Val Phe Val Ser Val Val Leu Phe Ile Leu
1               5                   10                  15

Leu Thr Pro Gly Leu Leu Ile Gln Ile Pro Gly Lys Gly Lys Met Val

```
                    20                  25                  30

Glu Phe Gly Asn Phe Gln Thr Ser Gly Val Ser Ile Leu Val His Ser
                35                  40                  45

Ile Leu Tyr Phe Ala Leu Val Cys Ile Phe Leu Met Ala Ile Gly Val
        50                  55                  60

His Met Tyr Thr Gly Ser
 65                  70

<210> SEQ ID NO 13
<211> LENGTH: 69
<212> TYPE: PRT
<213> ORGANISM: Lotus japonicus

<400> SEQUENCE: 13

Met Ala Asp Trp Gly Pro Val Phe Val Ser Val Val Leu Phe Ile Leu
  1               5                  10                  15

Leu Thr Pro Gly Leu Leu Ile Gln Ile Pro Gly Lys Ser Arg Met Val
                20                  25                  30

Glu Phe Gly Asn Phe Gln Thr Ser Gly Ala Ser Ile Leu Val His Ser
                35                  40                  45

Ile Leu Tyr Phe Val Leu Val Cys Ile Phe Leu Leu Ala Ile Gly Val
        50                  55                  60

His Met Tyr Met Gly
 65

<210> SEQ ID NO 14
<211> LENGTH: 161
<212> TYPE: PRT
<213> ORGANISM: Fragaria vesca subsp. vesca

<400> SEQUENCE: 14

Met Ser Asp Trp Gly Pro Val Phe Ile Ala Val Val Leu Phe Ile Leu
  1               5                  10                  15

Leu Thr Pro Gly Leu Leu Ile Gln Ile Pro Gly Lys Ser Arg Phe Val
                20                  25                  30

Glu Phe Gly Asn Phe Gln Thr Ser Gly Val Ser Ile Leu Val His Ser
                35                  40                  45

Ile Ile Tyr Phe Thr Leu Ile Cys Ile Phe Leu Leu Ala Ile Gly Val
        50                  55                  60

His Met Tyr Ile Val His Gly Leu Gly Ile Leu Ile Leu Thr Ser Tyr
 65                  70                  75                  80

Ser Asp Val Lys Phe Glu Ala Leu Asp Leu Lys Glu Met Ala Asp Trp
                85                  90                  95

Gly Pro Val Leu Ile Gly Val Val Leu Phe Ile Leu Leu Gln Pro Gly
               100                 105                 110

Leu Leu Phe Ser Leu Pro Gly Asn Gly Lys Gln Val Glu Phe Gly Ser
           115                 120                 125

Met Lys Thr Asn Gly Lys Ala Ile Ala Val His Thr Leu Ile Phe Phe
       130                 135                 140

Ala Leu Tyr Ala Ile Leu Ile Leu Ala Val His Val His Ile Tyr Thr
145                 150                 155                 160

Gly

<210> SEQ ID NO 15
<211> LENGTH: 69
<212> TYPE: PRT
<213> ORGANISM: Citrus clementina
```

<400> SEQUENCE: 15

Met Ser Asp Trp Gly Pro Val Phe Val Gly Val Val Leu Phe Ile Leu
1               5                   10                  15

Leu Ser Pro Gly Leu Leu Ile Gln Val Pro Gly Arg Asn Arg Phe Phe
            20                  25                  30

Glu Phe Gly Asn Phe Gln Thr Ser Gly Ala Ser Ile Leu Val His Ser
        35                  40                  45

Ile Leu Tyr Phe Ala Leu Met Cys Ile Phe Leu Leu Ala Ile Gly Val
    50                  55                  60

His Met Tyr Leu Gly
65

<210> SEQ ID NO 16
<211> LENGTH: 139
<212> TYPE: PRT
<213> ORGANISM: Prunus persica

<400> SEQUENCE: 16

Met Ser Asp Trp Gly Pro Val Phe Ile Ala Val Val Leu Phe Ile Leu
1               5                   10                  15

Leu Thr Pro Gly Leu Leu Ile Gln Met Pro Gly Lys Ser Arg Phe Val
            20                  25                  30

Glu Phe Gly Asn Phe Gln Thr Ser Gly Ile Ser Ile Leu Val His Ser
        35                  40                  45

Ile Ile Tyr Phe Ala Leu Ile Cys Ile Phe Leu Leu Ala Ile Gly Val
    50                  55                  60

His Met Tyr Glu Ile Ile Met Ala Asp Trp Gly Pro Ile Leu Ile Gly
65                  70                  75                  80

Val Val Leu Phe Ile Leu Leu Gln Pro Gly Leu Leu Phe Ser Leu Pro
                85                  90                  95

Gly Asn Ser Arg Gln Val Glu Phe Gly Ser Met Lys Thr Asn Gly Lys
            100                 105                 110

Ala Ile Ala Val His Thr Leu Ile Phe Phe Ala Leu Tyr Ala Ile Leu
        115                 120                 125

Ile Leu Ala Val His Val His Ile Tyr Thr Gly
    130                 135

<210> SEQ ID NO 17
<211> LENGTH: 69
<212> TYPE: PRT
<213> ORGANISM: Cicer arietinum

<400> SEQUENCE: 17

Met Ser Asp Trp Gly Pro Val Phe Val Ser Val Leu Phe Ile Leu
1               5                   10                  15

Leu Thr Pro Gly Leu Leu Val Gln Ile Pro Gly Lys Ala Lys Met Val
            20                  25                  30

Glu Phe Gly Asn Phe Gln Thr Ser Gly Leu Ser Ile Leu Ile His Ser
        35                  40                  45

Val Leu Tyr Phe Ala Leu Val Cys Ile Phe Leu Leu Ala Ile Arg Ile
    50                  55                  60

His Met Tyr Leu Gly
65

<210> SEQ ID NO 18
<211> LENGTH: 142

```
<212> TYPE: PRT
<213> ORGANISM: Cucumis sativus

<400> SEQUENCE: 18

Met Ala Asp Trp Gly Pro Val Phe Val Ala Val Met Leu Phe Val Leu
1               5                   10                  15

Leu Thr Pro Gly Leu Leu Val Gln Met Pro Gly Lys Ser Arg Phe Val
            20                  25                  30

Glu Phe Gly Asn Phe Gln Thr Ser Gly Val Ser Ile Leu Val His Ser
        35                  40                  45

Ile Leu Tyr Phe Ala Leu Ile Cys Ile Phe Leu Leu Ala Val Arg Val
    50                  55                  60

His Val Tyr Asn Gly Ile Ser Glu Thr Met Ser Asp Trp Ala Pro Val
65                  70                  75                  80

Val Ile Gly Val Val Leu Phe Val Leu Leu Ser Pro Gly Leu Leu Phe
                85                  90                  95

Gln Phe Pro Gly Asn Asn Arg Gln Phe Glu Phe Gly Ser Met Lys Thr
            100                 105                 110

Asn Gly Lys Ala Val Ala Ile His Thr Leu Ile Phe Phe Val Leu Tyr
        115                 120                 125

Ala Val Phe Ile Leu Ala Leu His Ile His Ile Tyr Thr Gly
    130                 135                 140

<210> SEQ ID NO 19
<211> LENGTH: 69
<212> TYPE: PRT
<213> ORGANISM: Glycine max

<400> SEQUENCE: 19

Met Gly Asp Trp Gly Pro Val Phe Val Ser Val Val Leu Phe Ile Leu
1               5                   10                  15

Leu Thr Pro Gly Leu Leu Val Gln Ile Pro Gly Arg Gly Arg Phe Ile
            20                  25                  30

Glu Phe Gly Asn Phe Gln Thr Ser Gly Leu Ser Ile Leu Ile His Ala
        35                  40                  45

Ile Leu Tyr Phe Ala Leu Val Cys Ile Phe Met Leu Ala Ile Gly Ile
    50                  55                  60

His Met Tyr Met Gly
65

<210> SEQ ID NO 20
<211> LENGTH: 69
<212> TYPE: PRT
<213> ORGANISM: Populus trichocarpa

<400> SEQUENCE: 20

Met Ser Asp Trp Gly Pro Val Phe Met Ala Val Val Leu Phe Ile Leu
1               5                   10                  15

Leu Thr Pro Gly Leu Leu Phe Gln Val Pro Gly Arg His Arg Ser Ile
            20                  25                  30

Glu Phe Gly Asn Phe Gln Thr Ser Gly Ala Ser Ile Met Val His Thr
        35                  40                  45

Leu Leu Tyr Phe Ala Leu Ile Cys Val Phe Leu Leu Ala Val Lys Val
    50                  55                  60

His Leu Tyr Leu Gly
65
```

-continued

```
<210> SEQ ID NO 21
<211> LENGTH: 69
<212> TYPE: PRT
<213> ORGANISM: Glycine max

<400> SEQUENCE: 21

Met Gly Asp Trp Gly Pro Val Phe Val Ser Val Val Leu Phe Ile Leu
1               5                   10                  15

Leu Ser Pro Gly Leu Leu Val Gln Ile Pro Gly Arg Gly Arg Phe Ile
            20                  25                  30

Glu Phe Gly Asn Phe Gln Thr Ser Gly Leu Ser Ile Leu Ile His Ala
        35                  40                  45

Ile Leu Tyr Phe Ala Leu Val Cys Ile Phe Met Leu Ala Ile Gly Ile
    50                  55                  60

His Met Tyr Met Gly
65

<210> SEQ ID NO 22
<211> LENGTH: 69
<212> TYPE: PRT
<213> ORGANISM: Medicago truncatula

<400> SEQUENCE: 22

Met Ser Asp Trp Gly Pro Val Phe Val Ser Val Val Leu Phe Ile Leu
1               5                   10                  15

Leu Thr Pro Gly Leu Leu Val Gln Ile Pro Gly Lys Gly Lys Met Val
            20                  25                  30

Glu Phe Gly Asn Phe Gln Thr Ser Gly Leu Ser Ile Leu Ile His Ser
        35                  40                  45

Ile Leu Tyr Phe Ala Leu Val Cys Ile Phe Phe Leu Ala Ile Arg Ile
    50                  55                  60

His Met Tyr Met Gly
65

<210> SEQ ID NO 23
<211> LENGTH: 69
<212> TYPE: PRT
<213> ORGANISM: Phaseolus vulgaris

<400> SEQUENCE: 23

Met Gly Asp Trp Gly Pro Val Phe Val Ser Val Val Leu Phe Ile Leu
1               5                   10                  15

Leu Thr Pro Gly Leu Leu Val Gln Ile Pro Gly Arg Gly Ser Phe Ile
            20                  25                  30

Glu Phe Gly Asn Phe Gln Thr Ser Gly Leu Ser Ile Leu Ile His Ala
        35                  40                  45

Ile Leu Tyr Phe Ala Leu Val Cys Ile Phe Met Leu Ala Ile Gly Ile
    50                  55                  60

His Met Tyr Met Gly
65

<210> SEQ ID NO 24
<211> LENGTH: 69
<212> TYPE: PRT
<213> ORGANISM: Cicer arietinum

<400> SEQUENCE: 24

Met Ala Asp Trp Gly Pro Ile Phe Val Ser Val Val Leu Phe Ile Leu
1               5                   10                  15
```

```
Leu Thr Pro Gly Leu Leu Phe Gln Ile Pro Gly Arg Asn Lys Ile Val
            20                  25                  30

Glu Phe Gly Asn Phe Gln Thr Ser Gly Leu Ser Ile Leu Ile His Ala
        35                  40                  45

Leu Leu Tyr Phe Gly Leu Val Cys Ile Phe Met Leu Ala Ile Gly Ile
    50                  55                  60

His Met Tyr Ala Gly
65

<210> SEQ ID NO 25
<211> LENGTH: 69
<212> TYPE: PRT
<213> ORGANISM: Populus trichocarpa

<400> SEQUENCE: 25

Met Ser Asp Trp Gly Pro Val Phe Met Ala Val Val Leu Phe Ile Leu
1               5                   10                  15

Leu Thr Pro Gly Leu Leu Phe Gln Val Pro Gly Arg His Arg Tyr Val
            20                  25                  30

Glu Phe Gly Asn Phe Gln Thr Ser Gly Ala Ser Ile Met Val His Thr
        35                  40                  45

Leu Leu Tyr Phe Ala Leu Ile Cys Val Ser Leu Leu Ala Val Lys Val
    50                  55                  60

His Leu Tyr Leu Gly
65

<210> SEQ ID NO 26
<211> LENGTH: 69
<212> TYPE: PRT
<213> ORGANISM: Glycine max

<400> SEQUENCE: 26

Met Ser Asp Trp Gly Pro Val Phe Val Ser Leu Val Leu Phe Val Leu
1               5                   10                  15

Leu Thr Pro Gly Leu Leu Phe Gln Val Pro Gly Arg Ser Arg Val Val
            20                  25                  30

Glu Phe Gly Asn Phe Gln Thr Ser Gly Ala Ala Ile Leu Ile His Ser
        35                  40                  45

Leu Leu Tyr Phe Ala Leu Ile Cys Val Phe Leu Ala Val Arg Ile
    50                  55                  60

His Phe Tyr Leu Gly
65

<210> SEQ ID NO 27
<211> LENGTH: 69
<212> TYPE: PRT
<213> ORGANISM: Citrus clementina

<400> SEQUENCE: 27

Met Ser Asp Trp Gly Pro Val Phe Ala Val Ile Leu Phe Val Leu
1               5                   10                  15

Leu Ser Pro Gly Leu Leu Phe Gln Val Pro Gly Arg His Arg Cys Val
            20                  25                  30

Glu Phe Gly Asn Phe Gln Thr Ser Gly Ala Ala Ile Met Val His Ser
        35                  40                  45

Leu Leu Tyr Phe Ala Leu Val Cys Val Phe Leu Ala Val Lys Val
    50                  55                  60

His Leu Tyr Leu Gly
```

<210> SEQ ID NO 28
<211> LENGTH: 140
<212> TYPE: PRT
<213> ORGANISM: Citrus sinensis

<400> SEQUENCE: 28

Met Ser Asp Trp Gly Pro Val Phe Val Gly Val Leu Phe Ile Leu
1               5                   10                  15

Leu Ser Pro Gly Leu Leu Ile Gln Val Pro Gly Arg Asn Arg Phe Phe
                20                  25                  30

Glu Phe Gly Asn Phe Gln Thr Ser Gly Ala Ser Ile Leu Val His Ser
                35                  40                  45

Ile Leu Tyr Phe Ala Leu Met Cys Ile Phe Leu Leu Ala Ile Gly Val
        50                  55                  60

His Ile Cys Asn Thr Ser Thr Met Ala Asp Trp Gly Pro Val Val Ile
65                  70                  75                  80

Gly Val Val Leu Phe Val Leu Leu Gln Pro Gly Leu Leu Phe Gln Leu
                    85                  90                  95

Pro Gly His Ser Arg Leu Leu Glu Phe Gly Ser Met Lys Thr Asn Gly
                100                 105                 110

Lys Ala Ile Ser Val His Thr Leu Ile Phe Phe Val Leu Tyr Ala Ile
            115                 120                 125

Leu Ile Leu Ala Val His Val His Ile Tyr Ser Gly
        130                 135                 140

<210> SEQ ID NO 29
<211> LENGTH: 69
<212> TYPE: PRT
<213> ORGANISM: Vitis vinifera

<400> SEQUENCE: 29

Met Ser Asp Trp Gly Ala Val Phe Val Ser Val Met Leu Phe Ile Leu
1               5                   10                  15

Leu Met Pro Gly Leu Leu Ile Gln Ile Pro Gly Arg Gly Arg Phe Ile
                20                  25                  30

Glu Phe Thr Asn Phe Gln Thr Ser Gly Val Ser Ile Leu Val His Ser
                35                  40                  45

Leu Ile Tyr Phe Thr Leu Ile Cys Ile Phe Leu Leu Ala Ile Gly Val
        50                  55                  60

His Met Tyr Ile Gly
65

<210> SEQ ID NO 30
<211> LENGTH: 69
<212> TYPE: PRT
<213> ORGANISM: Arabidopsis lyrata subsp. lyrata

<400> SEQUENCE: 30

Met Ser Asp Trp Gly Pro Val Leu Val Thr Val Ile Leu Phe Val Met
1               5                   10                  15

Leu Thr Pro Gly Leu Leu Phe Gln Leu Pro Gly Arg Gln Arg Tyr Val
                20                  25                  30

Glu Phe Gly Asn Phe Gln Thr Ser Ala Val Ser Val Ile Val His Ser
                35                  40                  45

Leu Leu Tyr Phe Ser Leu Val Cys Val Phe Leu Leu Ala Leu Lys Ile
        50                  55                  60

His Ile Tyr Ile Gly
65

<210> SEQ ID NO 31
<211> LENGTH: 102
<212> TYPE: PRT
<213> ORGANISM: Eucalyptus grandis

<400> SEQUENCE: 31

Thr Ser Ser Ile Thr Phe Phe Val Ile Ile Phe Thr Ile Ile Leu Pro
1               5                   10                  15

Gln Asn Tyr Pro Ser Lys Ile Ser Ser Glu Arg Glu Arg Ala Gly Glu
            20                  25                  30

Met Thr Asp Trp Gly Ser Val Phe Val Ala Ser Val Leu Phe Ile Leu
        35                  40                  45

Leu Thr Pro Gly Met Leu Phe Gln Ile Pro Gly Gln His Arg Tyr Val
    50                  55                  60

Glu Phe Gly Asn Phe His Thr Ser Gly Val Ser Ile Leu Val His Ser
65                  70                  75                  80

Ile Leu Tyr Leu Ala Phe Met Cys Ile Phe Leu Ile Ala Ile Gly Val
                85                  90                  95

His Met Tyr Ile Gly Ser
            100

<210> SEQ ID NO 32
<211> LENGTH: 69
<212> TYPE: PRT
<213> ORGANISM: Oryza sativa Japonica Group

<400> SEQUENCE: 32

Met Ala Asp Trp Gly Pro Val Phe Ile Gly Leu Val Leu Phe Ile Leu
1               5                   10                  15

Leu Ser Pro Gly Leu Leu Phe Gln Ile Pro Gly Lys Gly Arg Ile Val
            20                  25                  30

Glu Phe Gly Asn Phe Gln Thr Ser Gly Leu Ser Ile Leu Val His Ser
        35                  40                  45

Ile Ile Tyr Phe Ala Leu Ile Ala Ile Phe Leu Leu Ala Val Asn Val
    50                  55                  60

His Met Tyr Leu Gly
65

<210> SEQ ID NO 33
<211> LENGTH: 69
<212> TYPE: PRT
<213> ORGANISM: Arabidopsis thaliana

<400> SEQUENCE: 33

Met Ser Asp Trp Gly Pro Val Leu Val Thr Val Ile Leu Phe Val Met
1               5                   10                  15

Leu Thr Pro Gly Leu Leu Phe Gln Leu Pro Gly Arg Gln Lys Tyr Val
            20                  25                  30

Glu Phe Gly Asn Phe Gln Thr Ser Ala Val Ser Val Ile Val His Ser
        35                  40                  45

Leu Leu Tyr Phe Ser Leu Val Cys Val Phe Leu Leu Ala Leu Lys Ile
    50                  55                  60

His Ile Tyr Ile Gly
65

<210> SEQ ID NO 34
<211> LENGTH: 69
<212> TYPE: PRT
<213> ORGANISM: Brachypodium distachyon

<400> SEQUENCE: 34

Met Ala Asp Trp Gly Pro Val Phe Ile Gly Leu Val Leu Phe Ile Leu
1               5                   10                  15

Leu Ser Pro Gly Leu Leu Phe Gln Ile Pro Gly Lys Gly Arg Met Val
                20                  25                  30

Glu Phe Gly Asn Phe Gln Thr Ser Gly Leu Ser Ile Leu Val His Ala
            35                  40                  45

Val Ile Tyr Phe Ala Leu Ile Ala Ile Phe Ile Leu Ala Leu Gly Val
        50                  55                  60

His Val Tyr Leu Gly
65

<210> SEQ ID NO 35
<211> LENGTH: 69
<212> TYPE: PRT
<213> ORGANISM: Phaseolus vulgaris

<400> SEQUENCE: 35

Met Ser Asp Trp Gly Pro Val Phe Val Ser Leu Val Leu Phe Val Leu
1               5                   10                  15

Leu Thr Pro Gly Leu Leu Phe Gln Val Pro Gly Arg Gly Arg Cys Val
                20                  25                  30

Glu Phe Gly Asn Phe Gln Thr Ser Gly Ala Ser Val Leu Ile His Ser
            35                  40                  45

Leu Leu Tyr Phe Gly Phe Ile Cys Val Phe Leu Leu Ala Ile Lys Ile
        50                  55                  60

His Leu Tyr Leu Gly
65

<210> SEQ ID NO 36
<211> LENGTH: 69
<212> TYPE: PRT
<213> ORGANISM: Solanum lycopersicum

<400> SEQUENCE: 36

Met Ala Asp Trp Gly Pro Val Leu Ile Ala Val Val Leu Phe Val Leu
1               5                   10                  15

Leu Thr Pro Gly Leu Leu Phe Gln Leu Pro Gly Arg Gly Lys Thr Val
                20                  25                  30

Glu Phe Gly Asn Met Gln Thr Ser Gly Val Ser Ile Leu Val His Ala
            35                  40                  45

Val Ile Tyr Phe Gly Leu Ile Thr Ile Phe Leu Leu Ala Ile Gly Val
        50                  55                  60

His Val Tyr Val Gly
65

<210> SEQ ID NO 37
<211> LENGTH: 69
<212> TYPE: PRT
<213> ORGANISM: Amborella trichopoda

<400> SEQUENCE: 37

Met Ala Asp Trp Gly Pro Val Val Ile Ala Val Val Leu Phe Val Leu
1               5                   10                  15

-continued

Leu Ser Pro Gly Leu Leu Phe Gln Leu Pro Gly Lys Ser Arg Val Val
            20                  25                  30

Glu Phe Gly Asn Phe Gln Thr Ser Gly Ile Ser Ile Leu Val His Thr
        35                  40                  45

Ile Ile Tyr Phe Gly Leu Ile Thr Ile Phe Leu Ile Ala Ile Gly Val
    50                  55                  60

His Ile Tyr Thr Gly
65

<210> SEQ ID NO 38
<211> LENGTH: 70
<212> TYPE: PRT
<213> ORGANISM: Cucumis sativus

<400> SEQUENCE: 38

Met Ala Asp Trp Gly Pro Ile Phe Val Ala Val Ile Leu Phe Val Leu
1               5                   10                  15

Leu Thr Pro Gly Leu Leu Phe Gln Leu Pro Gly Asn Arg Arg Cys Leu
            20                  25                  30

Glu Phe Gly Asn Phe His Thr Ser Ala Ala Ala Ile Ile Val His Ser
        35                  40                  45

Ile Leu Tyr Phe Gly Leu Ile Cys Val Phe Leu Leu Ala Ile Lys Val
    50                  55                  60

His Leu Tyr Ile Gly Ser
65                  70

<210> SEQ ID NO 39
<211> LENGTH: 69
<212> TYPE: PRT
<213> ORGANISM: Zea mays

<400> SEQUENCE: 39

Met Ala Asp Trp Gly Pro Val Leu Ile Gly Leu Val Leu Phe Ile Leu
1               5                   10                  15

Leu Ser Pro Gly Leu Leu Phe Gln Ile Pro Gly Lys Gly Arg Ile Ile
            20                  25                  30

Glu Phe Gly Asn Phe Gln Thr Ser Gly Leu Ser Ile Leu Val His Ala
        35                  40                  45

Val Ile Tyr Phe Ala Leu Leu Ala Ile Phe Leu Leu Ala Val Gly Val
    50                  55                  60

His Ile Tyr Leu Gly
65

<210> SEQ ID NO 40
<211> LENGTH: 69
<212> TYPE: PRT
<213> ORGANISM: Sorghum bicolor

<400> SEQUENCE: 40

Met Ala Asp Trp Gly Pro Val Leu Ile Gly Leu Val Leu Phe Ile Leu
1               5                   10                  15

Leu Ser Pro Gly Leu Leu Phe Gln Ile Pro Gly Lys Gly Arg Ile Ile
            20                  25                  30

Glu Phe Gly Asn Phe Gln Thr Ser Gly Leu Ser Ile Leu Ile His Ala
        35                  40                  45

Val Ile Tyr Phe Ala Leu Leu Ala Ile Phe Leu Leu Ala Val Gly Val
    50                  55                  60

His Ile Tyr Leu Gly
65

<210> SEQ ID NO 41
<211> LENGTH: 69
<212> TYPE: PRT
<213> ORGANISM: Solanum tuberosum

<400> SEQUENCE: 41

Met Glu Asp Trp Gly Pro Val Leu Ile Ala Val Val Leu Phe Val Leu
1               5                   10                  15

Leu Thr Pro Gly Leu Leu Phe Gln Leu Pro Gly Arg Gly Lys Thr Val
            20                  25                  30

Glu Phe Gly Asn Met Gln Thr Ser Gly Val Ser Ile Leu Val His Ala
        35                  40                  45

Val Ile Tyr Phe Gly Leu Ile Thr Ile Leu Leu Ala Ile Gly Val
    50                  55                  60

His Val Tyr Val Gly
65

<210> SEQ ID NO 42
<211> LENGTH: 69
<212> TYPE: PRT
<213> ORGANISM: Solanum lycopersicum

<400> SEQUENCE: 42

Met Ser Asp Trp Gly Pro Val Leu Ile Ala Val Val Leu Phe Val Leu
1               5                   10                  15

Leu Ser Pro Gly Leu Leu Phe Gln Leu Pro Gly Arg His Lys Ile Val
            20                  25                  30

Glu Phe Gly Asn Met Gln Thr Ser Gly Leu Ser Val Leu Val His Thr
        35                  40                  45

Val Leu Tyr Phe Ala Leu Ile Thr Val Phe Leu Ile Ala Ile Gly Val
    50                  55                  60

His Ile His Thr Gly
65

<210> SEQ ID NO 43
<211> LENGTH: 143
<212> TYPE: PRT
<213> ORGANISM: Cicer arietinum

<400> SEQUENCE: 43

Met Ser Asp Trp Gly Pro Val Phe Val Ser Ile Val Leu Phe Val Leu
1               5                   10                  15

Leu Thr Pro Gly Leu Leu Phe Gln Leu Pro Gly Arg Ser Arg Cys Val
            20                  25                  30

Glu Phe Gly Asn Phe Gln Thr Ser Gly Ala Ser Ile Leu Ile His Ser
        35                  40                  45

Leu Leu Tyr Phe Ala Phe Ile Cys Ile Phe Leu Ile Ala Val Lys Ile
    50                  55                  60

His Leu Cys Asn Leu Gln Lys Leu Val Met Ala Ala Asp Trp Gly Pro
65                  70                  75                  80

Val Val Ile Ser Val Val Leu Phe Val Leu Leu Ser Pro Gly Leu Leu
                85                  90                  95

Phe Gln Leu Pro Ala Lys Gly Arg Val Val Ala Phe Gly Ser Met Gln
            100                 105                 110

Thr Ser Gly Ile Ser Ile Leu Val His Thr Ile Ile Phe Phe Gly Leu

```
            115                 120                 125
Ile Thr Ile Phe Leu Leu Ala Ile Gly Ile His Ile Tyr Ser Gly
        130                 135                 140
```

<210> SEQ ID NO 44
<211> LENGTH: 69
<212> TYPE: PRT
<213> ORGANISM: Eucalyptus grandis

<400> SEQUENCE: 44

```
Met Ala Asp Trp Gly Pro Val Ile Ala Val Val Leu Phe Val Leu
1               5                   10                  15

Leu Ser Pro Gly Leu Leu Phe Gln Leu Pro Gly Arg Gln Arg Phe Ile
            20                  25                  30

Glu Phe Gly Asn Met Gln Thr Ser Gly Leu Ser Ile Leu Val His Thr
        35                  40                  45

Ile Ile Phe Phe Gly Leu Ile Thr Ile Phe Leu Ile Ala Ile Gly Val
    50                  55                  60

His Ile Tyr Thr Gly
65
```

<210> SEQ ID NO 45
<211> LENGTH: 76
<212> TYPE: PRT
<213> ORGANISM: Oryza sativa Japonica Group

<400> SEQUENCE: 45

```
Met Ala Asp Trp Gly Pro Val Phe Ile Gly Leu Val Leu Phe Ile Leu
1               5                   10                  15

Leu Ser Pro Gly Leu Leu Phe Gln Ile Pro Gly Lys Gly Arg Ile Val
            20                  25                  30

Glu Phe Gly Asn Phe Gln Thr Ser Gly Leu Ser Ile Leu Val His Ser
        35                  40                  45

Ile Ile Tyr Phe Ala Leu Ile Ala Ile Phe Leu Leu Ala Val Asn Val
    50                  55                  60

His Met Phe Leu Glu Phe Gly Tyr Leu Pro Trp Ile
65                  70                  75
```

<210> SEQ ID NO 46
<211> LENGTH: 69
<212> TYPE: PRT
<213> ORGANISM: Setaria italica

<400> SEQUENCE: 46

```
Met Ala Asp Trp Ala Pro Val Phe Ile Gly Leu Val Leu Phe Ile Leu
1               5                   10                  15

Leu Ser Pro Gly Leu Leu Phe Gln Ile Pro Gly Lys Gly Arg Ile Ile
            20                  25                  30

Glu Phe Gly Asn Phe Gln Thr Ser Gly Leu Ser Ile Leu Ile His Ala
        35                  40                  45

Ile Ile Tyr Phe Thr Leu Ile Ala Ile Leu Leu Leu Ala Val Gly Val
    50                  55                  60

His Val Tyr Leu Gly
65
```

<210> SEQ ID NO 47
<211> LENGTH: 69
<212> TYPE: PRT
<213> ORGANISM: Arabidopsis thaliana

<400> SEQUENCE: 47

Met Pro Asp Trp Gly Pro Val Phe Val Ala Val Thr Leu Phe Val Leu
1               5                   10                  15

Leu Thr Pro Gly Leu Leu Ile Gln Val Pro Gly Arg Gly Arg Val Val
            20                  25                  30

Glu Phe Gly Thr Phe Gln Thr Ser Gly Leu Ser Val Ile Val His Thr
        35                  40                  45

Leu Ile Tyr Phe Thr Leu Val Cys Ile Leu Leu Ala Leu Gln Ile
    50                  55                  60

His Met Tyr Ile Gly
65

<210> SEQ ID NO 48
<211> LENGTH: 72
<212> TYPE: PRT
<213> ORGANISM: Fragaria vesca subsp. vesca

<400> SEQUENCE: 48

Met Ala Asp Trp Gly Pro Val Leu Ile Ala Val Ala Leu Phe Val Leu
1               5                   10                  15

Leu Thr Pro Gly Leu Leu Phe Gln Leu Pro Gly Lys Ser Arg Val Val
            20                  25                  30

Glu Phe Asn Asn Met Gln Thr Ser Gly Val Ser Ile Leu Val His Thr
        35                  40                  45

Ile Ile Tyr Phe Gly Leu Ile Thr Ile Phe Leu Ile Ala Ile Gly Val
    50                  55                  60

His Ile Tyr Thr Gly Gly Gly Asp
65                  70

<210> SEQ ID NO 49
<211> LENGTH: 70
<212> TYPE: PRT
<213> ORGANISM: Zea mays

<400> SEQUENCE: 49

Met Gln Asp Trp Ala Pro Val Phe Val Ser Leu Val Leu Phe Ile Leu
1               5                   10                  15

Leu Ser Pro Gly Leu Leu Phe Gln Met Pro Gly Lys Cys Arg Ile Ile
            20                  25                  30

Glu Phe Gly Asn Phe Gln Thr Ser Ala Ile Ser Ile Leu Val His Ala
        35                  40                  45

Ile Leu Phe Phe Ala Leu Ala Ala Ile Phe Leu Val Ala Val Gly Val
    50                  55                  60

His Met Tyr Leu Gly Ser
65                  70

<210> SEQ ID NO 50
<211> LENGTH: 69
<212> TYPE: PRT
<213> ORGANISM: Fragaria vesca subsp. vesca

<400> SEQUENCE: 50

Met Ala Asp Trp Gly Pro Val Ile Ile Ala Val Val Leu Phe Val Leu
1               5                   10                  15

Leu Thr Pro Gly Leu Leu Phe Gln Ile Pro Gly Lys Gly Arg Val Val
            20                  25                  30

Glu Phe Gly Asn Met Gln Thr Ser Gly Ala Ser Ile Val Val His Ala 35                  40                  45
Ile Ile Tyr Phe Gly Leu Leu Thr Ile Phe Leu Ile Ala Ile Gly Val
            50                  55                  60

His Ile Tyr Thr Gly
 65

<210> SEQ ID NO 51
<211> LENGTH: 70
<212> TYPE: PRT
<213> ORGANISM: Sorghum bicolor

<400> SEQUENCE: 51

Met Gln Asp Trp Ala Pro Val Phe Ile Ser Leu Val Leu Phe Ile Leu
 1               5                  10                  15

Leu Ser Pro Gly Leu Leu Phe Gln Met Pro Gly Lys Cys Arg Ile Ile
            20                  25                  30

Glu Phe Gly Asn Phe Gln Thr Ser Ala Ile Ser Ile Leu Val His Ala
        35                  40                  45

Ile Leu Phe Phe Ala Leu Ala Ala Ile Phe Leu Ile Ala Val Gly Val
    50                  55                  60

His Met Tyr Leu Gly Ser
 65                  70

<210> SEQ ID NO 52
<211> LENGTH: 69
<212> TYPE: PRT
<213> ORGANISM: Solanum tuberosum

<400> SEQUENCE: 52

Met Ser Asp Trp Gly Pro Val Leu Ile Ala Val Val Leu Phe Val Leu
 1               5                  10                  15

Leu Ser Pro Gly Leu Leu Phe Gln Leu Pro Gly Arg His Lys Ile Val
            20                  25                  30

Glu Phe Gly Asn Met Gln Thr Ser Gly Leu Ser Ile Leu Val His Thr
        35                  40                  45

Val Leu Tyr Phe Gly Val Ile Thr Ile Phe Leu Ile Ala Ile Gly Val
    50                  55                  60

His Ile His Thr Gly
 65

<210> SEQ ID NO 53
<211> LENGTH: 69
<212> TYPE: PRT
<213> ORGANISM: Capsella rubella

<400> SEQUENCE: 53

Met Pro Asp Trp Gly Pro Val Phe Val Ala Val Thr Leu Phe Val Leu
 1               5                  10                  15

Leu Thr Pro Gly Leu Leu Ile Gln Ile Pro Gly Arg Gly Arg Val Val
            20                  25                  30

Glu Phe Gly Thr Phe Gln Thr Ser Gly Leu Ser Val Ile Val His Thr
        35                  40                  45

Leu Ile Tyr Phe Thr Ile Val Cys Ile Leu Leu Ala Leu Gln Ile
    50                  55                  60

His Met Tyr Ile Gly
 65

<210> SEQ ID NO 54

-continued

```
<211> LENGTH: 69
<212> TYPE: PRT
<213> ORGANISM: Eucalyptus grandis

<400> SEQUENCE: 54

Met Ala Asp Trp Gly Pro Val Val Ile Ala Val Val Leu Phe Val Leu
1               5                   10                  15

Leu Ser Pro Gly Leu Leu Phe Gln Ile Pro Gly Arg His Arg Val Val
                20                  25                  30

Glu Phe Gly Asn Met Glu Thr Ser Gly Ala Ser Ile Leu Val His Thr
            35                  40                  45

Ile Ile Tyr Phe Gly Leu Ile Thr Ile Leu Ile Ala Ile Gly Val
        50                  55                  60

His Ile Tyr Thr Gly
65

<210> SEQ ID NO 55
<211> LENGTH: 69
<212> TYPE: PRT
<213> ORGANISM: Prunus persica

<400> SEQUENCE: 55

Met Ala Asp Trp Gly Pro Val Val Ile Ala Val Val Leu Phe Val Leu
1               5                   10                  15

Leu Thr Pro Gly Leu Leu Phe Gln Leu Pro Gly Asn Ser Arg Val Val
                20                  25                  30

Glu Phe Asn Asn Met Gln Thr Ser Gly Val Ser Ile Leu Val His Thr
            35                  40                  45

Ile Ile Tyr Phe Gly Leu Val Thr Ile Phe Leu Ile Ala Ile Gly Val
        50                  55                  60

His Ile Tyr Thr Gly
65

<210> SEQ ID NO 56
<211> LENGTH: 69
<212> TYPE: PRT
<213> ORGANISM: Cicer arietinum

<400> SEQUENCE: 56

Met Ala Asp Trp Gly Pro Val Ile Ile Ala Val Val Leu Phe Val Leu
1               5                   10                  15

Leu Ser Pro Gly Leu Leu Phe Gln Ile Pro Gly Arg Gly Arg Val Ile
                20                  25                  30

Glu Phe Gly Asn Met Gln Thr Ser Gly Ala Ser Ile Leu Val His Ala
            35                  40                  45

Ile Ile Tyr Phe Gly Leu Ile Thr Ile Leu Leu Ile Ala Ile Gly Val
        50                  55                  60

His Ile Tyr Thr Gly
65

<210> SEQ ID NO 57
<211> LENGTH: 105
<212> TYPE: PRT
<213> ORGANISM: Populus trichocarpa

<400> SEQUENCE: 57

Ser Cys Asn Thr Phe Ala Leu Pro Tyr Ile Asn Arg Glu Phe Asp Ile
1               5                   10                  15

Arg Ala Ala Val Arg Arg Ile Ser Ile Lys His Gln His Pro Glu Lys
```

-continued

```
                    20                  25                  30
Lys Lys Glu Ala Met Ser Asp Trp Gly Pro Val Val Ile Ala Val Val
            35                  40                  45

Leu Phe Val Leu Leu Ser Pro Gly Leu Leu Phe Gln Leu Pro Gly Arg
        50                  55                  60

Asn Arg Val Val Glu Phe Gly Asn Met Gln Thr Ser Ala Leu Ser Ile
 65                 70                  75                  80

Leu Val His Thr Ile Ile Phe Phe Gly Leu Ile Thr Ile Phe Leu Ile
                85                  90                  95

Ala Ile Gly Val His Ile Tyr Thr Gly
            100                 105

<210> SEQ ID NO 58
<211> LENGTH: 69
<212> TYPE: PRT
<213> ORGANISM: Ricinus communis

<400> SEQUENCE: 58

Met Ala Asp Trp Gly Pro Val Val Ile Ala Val Val Leu Phe Val Leu
 1               5                  10                  15

Leu Ser Pro Gly Leu Leu Phe Gln Leu Pro Gly Lys Gly Arg Val Val
            20                  25                  30

Glu Phe Gly Asn Met Gln Thr Ser Gly Leu Ser Ile Leu Val His Thr
        35                  40                  45

Ile Ile Phe Phe Ala Leu Val Thr Ile Phe Leu Ile Ala Ile Gly Val
    50                  55                  60

His Ile Tyr Thr Gly
 65

<210> SEQ ID NO 59
<211> LENGTH: 69
<212> TYPE: PRT
<213> ORGANISM: Citrus sinensis

<400> SEQUENCE: 59

Met Ala Asp Trp Gly Pro Val Val Ile Ala Thr Val Leu Phe Val Leu
 1               5                  10                  15

Leu Thr Pro Gly Leu Leu Phe Gln Ile Pro Gly Arg Asn Arg Val Val
            20                  25                  30

Glu Phe Gly Asn Met Gln Thr Ser Gly Ala Ser Ile Leu Val His Ser
        35                  40                  45

Val Ile Phe Phe Gly Leu Ile Thr Ile Phe Leu Ile Ala Ile Thr Val
    50                  55                  60

His Ile Tyr Thr Gly
 65

<210> SEQ ID NO 60
<211> LENGTH: 140
<212> TYPE: PRT
<213> ORGANISM: Vitis vinifera

<400> SEQUENCE: 60

Met Ser Asp Trp Gly Ala Val Phe Val Ser Val Met Leu Phe Ile Leu
 1               5                  10                  15

Leu Met Pro Gly Leu Leu Ile Gln Ile Pro Gly Arg Gly Arg Phe Ile
            20                  25                  30

Glu Phe Thr Asn Phe Gln Thr Ser Gly Val Ser Ile Leu Val His Ser
        35                  40                  45
```

```
Leu Ile Tyr Phe Thr Leu Ile Cys Ile Phe Leu Leu Ala Ile Gly Val
         50                  55                  60

His Met Cys Asp Ile Phe Glu Met Ala Asp Trp Ala Pro Val Leu Val
 65                  70                  75                  80

Gly Val Val Leu Phe Val Leu Leu Ser Pro Gly Leu Leu Phe Gln Leu
                 85                  90                  95

Pro Gly His Tyr Arg His Val Asp Phe Gly Gly Met Lys Thr Asn Gly
            100                 105                 110

Lys Ser Ile Ala Val His Thr Leu Ile Phe Val Ala Ile Phe Ala Val
        115                 120                 125

Leu Ile Met Ala Leu His Leu His Ile Tyr Thr Gly
        130                 135                 140

<210> SEQ ID NO 61
<211> LENGTH: 69
<212> TYPE: PRT
<213> ORGANISM: Cucumis sativus

<400> SEQUENCE: 61

Met Ala Asp Trp Gly Pro Val Ile Ala Val Val Leu Phe Val Leu
 1               5                  10                  15

Leu Ser Pro Gly Leu Leu Phe Gln Ile Pro Ala Lys Gly Arg Val Val
                 20                  25                  30

Glu Phe Gly Asn Met Gln Thr Ser Gly Ala Ser Ile Leu Val His Ala
             35                  40                  45

Ile Ile Tyr Phe Gly Leu Ile Thr Ile Phe Leu Ile Ala Ile Gly Val
         50                  55                  60

His Ile Tyr Thr Gly
 65

<210> SEQ ID NO 62
<211> LENGTH: 71
<212> TYPE: PRT
<213> ORGANISM: Vitis vinifera

<400> SEQUENCE: 62

Met Thr Asp Trp Gly Pro Val Val Ala Thr Val Leu Phe Val Leu
 1               5                  10                  15

Leu Thr Pro Gly Leu Leu Cys Gln Ile Pro Gly Arg Gly Arg Val Val
                 20                  25                  30

Glu Phe Gly Asn Met Ser Thr Ser Gly Leu Ser Ile Leu Val His Ala
             35                  40                  45

Val Ile Tyr Phe Ala Leu Val Thr Ile Phe Val Ile Ala Val Ser Val
         50                  55                  60

His Ile Tyr Ser Gly Ser Gly
 65                  70

<210> SEQ ID NO 63
<211> LENGTH: 69
<212> TYPE: PRT
<213> ORGANISM: Vitis vinifera

<400> SEQUENCE: 63

Met Ala Asp Trp Gly Pro Val Ile Ala Val Val Leu Phe Val Leu
 1               5                  10                  15

Leu Thr Pro Gly Leu Leu Phe Gln Leu Pro Gly Asn Asn Arg Val Val
                 20                  25                  30
```

Glu Phe Gly Asn Met Gln Thr Ser Arg Ile Ser Ile Leu Val His Thr
               35                  40                  45

Ile Ile Tyr Phe Gly Leu Ile Thr Ile Phe Leu Ile Ala Ile Gly Val
        50                  55                  60

His Ile Tyr Thr Gly
 65

<210> SEQ ID NO 64
<211> LENGTH: 69
<212> TYPE: PRT
<213> ORGANISM: Triticum urartu

<400> SEQUENCE: 64

Met Ala Asp Trp Ala Pro Val Phe Ile Gly Leu Val Leu Phe Ile Leu
  1               5                  10                  15

Leu Ser Pro Gly Leu Leu Phe Gln Ile Pro Gly Lys Gly Arg Met Val
               20                  25                  30

Glu Phe Gly Asn Phe Gln Thr Ser Gly Ile Ser Ile Leu Val His Ala
               35                  40                  45

Val Ile Tyr Phe Ala Leu Ile Ala Ile Leu Leu Ala Val Asn Val
        50                  55                  60

His Val Phe Leu Gly
 65

<210> SEQ ID NO 65
<211> LENGTH: 69
<212> TYPE: PRT
<213> ORGANISM: Glycine max

<400> SEQUENCE: 65

Met Ala Asp Trp Gly Pro Val Val Ile Ala Val Val Leu Phe Val Leu
  1               5                  10                  15

Leu Ser Pro Gly Leu Leu Phe Gln Leu Pro Gly Arg Ser Arg Val Val
               20                  25                  30

Glu Phe Gly Asn Met Gln Thr Ser Ala Ile Ser Ile Leu Val His Thr
               35                  40                  45

Ile Ile Phe Phe Gly Leu Ile Thr Ile Phe Leu Ile Ala Ile Gly Val
        50                  55                  60

His Ile Tyr Thr Gly
 65

<210> SEQ ID NO 66
<211> LENGTH: 121
<212> TYPE: PRT
<213> ORGANISM: Eucalyptus grandis

<400> SEQUENCE: 66

Met Lys Gly Gly Ile Arg Gly Trp Ala Glu Gln Gly Asn Gly Trp Phe
  1               5                  10                  15

Glu Ser Ala Val Thr Asn Arg Ala Lys Pro Gln Lys Trp Ser Arg Arg
               20                  25                  30

Ser Arg Phe Lys Phe Lys Lys Phe Thr Arg Arg Arg Arg Arg
               35                  40                  45

Arg Lys Gly Arg Met Ala Asp Trp Gly Pro Val Val Ile Ala Val Val
        50                  55                  60

Leu Phe Val Leu Leu Ser Pro Gly Leu Leu Phe Gln Ile Pro Gly Arg
 65                   70                  75                  80

His Arg Val Val Glu Phe Gly Asn Met Glu Thr Ser Gly Ala Ser Ile

```
                85                  90                  95
Leu Val His Thr Ile Ile Tyr Phe Gly Leu Ile Thr Ile Leu Leu Ile
            100                 105                 110

Ala Ile Gly Val His Ile Tyr Thr Gly
        115                 120

<210> SEQ ID NO 67
<211> LENGTH: 69
<212> TYPE: PRT
<213> ORGANISM: Medicago truncatula

<400> SEQUENCE: 67

Met Ala Asp Trp Gly Pro Val Ile Ala Val Val Leu Phe Val Leu
1               5                   10                  15

Leu Ser Pro Gly Leu Leu Phe Gln Met Pro Gly Arg Asn Lys Val Val
            20                  25                  30

Glu Phe Gly Asn Met Gln Thr Ser Gly Val Ser Ile Leu Val His Thr
        35                  40                  45

Ile Leu Phe Phe Gly Leu Ile Thr Ile Phe Leu Ile Ala Ile Gly Val
    50                  55                  60

His Ile Asn Thr Gly
65

<210> SEQ ID NO 68
<211> LENGTH: 69
<212> TYPE: PRT
<213> ORGANISM: Phaseolus vulgaris

<400> SEQUENCE: 68

Met Ala Asp Trp Gly Pro Val Ile Ile Ala Val Val Leu Phe Val Leu
1               5                   10                  15

Leu Ser Pro Gly Leu Leu Phe Gln Ile Pro Ser Arg Gly Arg Ile Ala
            20                  25                  30

Glu Phe Gly Asn Met Gln Thr Ser Gly Ala Ser Ile Leu Val His Ala
        35                  40                  45

Val Ile Tyr Phe Gly Leu Ile Thr Ile Phe Leu Ile Ala Ile Gly Val
    50                  55                  60

His Ile Tyr Thr Gly
65

<210> SEQ ID NO 69
<211> LENGTH: 69
<212> TYPE: PRT
<213> ORGANISM: Ricinus communis

<400> SEQUENCE: 69

Met Ala Asp Trp Gly Pro Val Ile Ile Ala Val Ile Leu Phe Val Leu
1               5                   10                  15

Leu Thr Pro Gly Leu Leu Phe Gln Ile Pro Gly Arg Asn Arg Val Val
            20                  25                  30

Glu Phe Gly Asn Met His Thr Ser Gly Ala Ser Ile Val Val His Ala
        35                  40                  45

Ile Ile Tyr Phe Gly Leu Ile Thr Ile Leu Leu Ile Ala Ile Gly Ile
    50                  55                  60

His Ile Tyr Ala Gly
65

<210> SEQ ID NO 70
```

```
<211> LENGTH: 69
<212> TYPE: PRT
<213> ORGANISM: Cicer arietinum

<400> SEQUENCE: 70

Met Ala Asp Trp Gly Pro Val Val Ile Ala Val Val Leu Phe Val Leu
1               5                   10                  15

Leu Ser Pro Gly Leu Leu Phe Gln Leu Pro Gly Arg Ser Arg Val Val
            20                  25                  30

Glu Phe Gly Asn Met Gln Thr Ser Gly Val Ser Ile Leu Val His Thr
        35                  40                  45

Ile Ile Phe Phe Gly Leu Ile Thr Ile Phe Leu Ile Ala Ile Gly Val
    50                  55                  60

His Ile Asn Thr Gly
65

<210> SEQ ID NO 71
<211> LENGTH: 70
<212> TYPE: PRT
<213> ORGANISM: Setaria italica

<400> SEQUENCE: 71

Met Gln Asp Trp Ala Pro Val Phe Ile Ser Leu Val Leu Phe Ile Leu
1               5                   10                  15

Leu Ser Pro Gly Leu Leu Phe Gln Ile Pro Gly Lys Cys Arg Ile Ile
            20                  25                  30

Glu Phe Gly Asn Phe His Thr Ser Ala Leu Ser Ile Leu Val His Ala
        35                  40                  45

Ile Leu Tyr Phe Ala Leu Ile Ala Ile Phe Leu Ile Ala Ile Gly Val
    50                  55                  60

Arg Met Tyr Leu Gly Ser
65                  70

<210> SEQ ID NO 72
<211> LENGTH: 135
<212> TYPE: PRT
<213> ORGANISM: Theobroma cacao

<400> SEQUENCE: 72

Met Asn Met Phe Tyr Ser Ile Phe Ile Val Asp Phe Ile Gly Glu Phe
1               5                   10                  15

Val Phe Asn Leu Gly Ser Gln Ala Glu Ser Trp Phe Cys Asn Ser Ser
            20                  25                  30

Thr Ser Ala Thr Ile Met Pro Leu Gln Glu Val Asn Val Cys His Leu
        35                  40                  45

Phe Val Asn Ser Val Gly Gln Ser Ser Arg Leu Gln Arg Lys Ile Gly
    50                  55                  60

Lys Ser Met Ala Asp Trp Gly Pro Val Val Ile Ala Val Val Leu Phe
65                  70                  75                  80

Val Leu Leu Ser Pro Gly Leu Leu Phe Gln Leu Pro Gly Arg Ser Lys
                85                  90                  95

Val Val Glu Phe Gly Asn Met Gln Thr Ser Gly Ile Ser Ile Leu Val
            100                 105                 110

His Thr Ile Ile Phe Phe Gly Leu Ile Thr Ile Phe Leu Ile Ala Ile
        115                 120                 125

Gly Val His Ile Tyr Thr Gly
    130                 135
```

-continued

<210> SEQ ID NO 73
<211> LENGTH: 103
<212> TYPE: PRT
<213> ORGANISM: Glycine max

<400> SEQUENCE: 73

Met Leu Thr Arg Leu Ala Arg Arg Arg Ser Ile Arg Phe Arg Leu Ser
1               5                   10                  15

Asp Phe Val Tyr Leu Cys Pro Pro Glu Ala Leu Lys Leu Phe Ser Ala
            20                  25                  30

Leu Lys Met Ala Asp Trp Gly Pro Val Val Ile Ala Val Val Leu Phe
        35                  40                  45

Val Leu Leu Ser Pro Gly Leu Leu Phe Gln Met Pro Ala Arg Gly Arg
    50                  55                  60

Val Ala Glu Phe Gly Asn Met Gln Thr Ser Gly Ala Ser Ile Leu Val
65                  70                  75                  80

His Ala Ile Ile Tyr Phe Gly Leu Ile Thr Ile Phe Leu Ile Ala Ile
                85                  90                  95

Gly Val His Ile Tyr Thr Gly
            100

<210> SEQ ID NO 74
<211> LENGTH: 69
<212> TYPE: PRT
<213> ORGANISM: Eucalyptus grandis

<400> SEQUENCE: 74

Met Ala Asp Trp Gly Pro Val Val Ile Ala Val Val Leu Phe Ile Leu
1               5                   10                  15

Leu Ser Pro Gly Leu Leu Phe Gln Leu Pro Gly Lys Met Lys Ala Val
            20                  25                  30

Glu Phe Gly Asn Met Gln Thr Thr Gly Ala Ser Ile Leu Val His Thr
        35                  40                  45

Ile Ile Phe Phe Cys Leu Ile Thr Ile Phe Leu Ile Ala Val Gly Val
    50                  55                  60

His Ile Tyr Thr Gly
65

<210> SEQ ID NO 75
<211> LENGTH: 141
<212> TYPE: PRT
<213> ORGANISM: Vitis vinifera

<400> SEQUENCE: 75

Met Ala Asp Trp Ala Pro Ile Leu Ile Gly Leu Leu Leu Phe Ile Leu
1               5                   10                  15

Leu Ser Pro Gly Leu Ile Phe Gln Leu Pro Gly Ser Val Arg His Ile
            20                  25                  30

Glu Phe Gly Ser Phe Gly Thr Asn Gly Lys Ala Met Leu Ile His Thr
        35                  40                  45

Ile Leu Phe Phe Gly Ile Phe Thr Ile Leu Met Ala Leu Asn Ile
    50                  55                  60

His Ile Tyr Leu Ala Glu Ser Val Met Ala Asp Trp Gly Pro Val Leu
65                  70                  75                  80

Ile Ala Val Val Leu Phe Val Leu Leu Thr Pro Gly Leu Leu Phe Gln
                85                  90                  95

Val Pro Gly Lys Asn Arg Val Val Glu Phe Gly Ser Met His Thr Ser

```
                100             105             110
Gly Ala Ser Ile Leu Val His Thr Ile Ile Tyr Phe Gly Leu Ile Thr
            115                 120                 125
Ile Phe Leu Ile Ala Ile Gly Val His Ile Tyr Thr Gly
        130                 135                 140

<210> SEQ ID NO 76
<211> LENGTH: 69
<212> TYPE: PRT
<213> ORGANISM: Solanum lycopersicum

<400> SEQUENCE: 76

Met Ala Asp Trp Gly Pro Val Val Ile Ala Val Val Leu Phe Val Leu
1               5                   10                  15
Leu Ser Pro Gly Leu Leu Phe Gln Leu Pro Gly Asn Asn Arg Ala Val
            20                  25                  30
Glu Phe Ala Asn Phe Gln Thr Ser Gly Leu Ser Ile Phe Ile His Thr
        35                  40                  45
Ile Leu Phe Phe Gly Leu Ile Thr Ile Phe Leu Ile Ala Ile Gly Val
    50                  55                  60
His Ile Tyr Thr Gly
65

<210> SEQ ID NO 77
<211> LENGTH: 69
<212> TYPE: PRT
<213> ORGANISM: Glycine max

<400> SEQUENCE: 77

Met Ala Asp Trp Gly Pro Val Val Ile Ala Val Val Leu Phe Val Leu
1               5                   10                  15
Leu Ser Pro Gly Leu Val Phe Gln Leu Pro Gly Lys Ser Arg Val Val
            20                  25                  30
Glu Phe Gly Asn Met Gln Thr Ser Ala Val Ser Ile Leu Val His Thr
        35                  40                  45
Ile Ile Phe Phe Gly Leu Ile Thr Ile Phe Leu Val Ala Ile Gly Val
    50                  55                  60
His Ile Tyr Thr Gly
65

<210> SEQ ID NO 78
<211> LENGTH: 69
<212> TYPE: PRT
<213> ORGANISM: Erythranthe guttata

<400> SEQUENCE: 78

Met Ala Asp Trp Gly Pro Val Val Ile Ala Val Val Leu Phe Val Leu
1               5                   10                  15
Leu Ser Pro Gly Leu Leu Phe Gln Leu Pro Gly Arg Gly Arg Val Val
            20                  25                  30
Glu Phe Gly Asn Met Gln Thr Ser Gly Leu Ser Ile Leu Val His Thr
        35                  40                  45
Val Ile Phe Phe Gly Leu Ile Thr Ile Phe Leu Ile Ala Ile Gly Val
    50                  55                  60
His Ile Tyr Ala Ala
65

<210> SEQ ID NO 79
```

```
<211> LENGTH: 101
<212> TYPE: PRT
<213> ORGANISM: Citrus clementina

<400> SEQUENCE: 79

Met Ala Asp Trp Gly Pro Val Ile Ala Thr Val Leu Phe Val Leu
1               5                   10                  15

Leu Thr Pro Gly Leu Leu Phe Gln Ile Pro Gly Arg Asn Arg Val Val
            20                  25                  30

Glu Phe Gly Asn Met Gln Thr Ser Gly Ala Ser Ile Leu Val His Ser
        35                  40                  45

Val Ile Phe Phe Gly Leu Ile Thr Ile Phe Leu Ile Ala Ile Thr Val
    50                  55                  60

His Ile Tyr Leu Ala Asp Phe Leu Tyr Pro Val Ser Ser Val Ser Cys
65                  70                  75                  80

Cys Phe Tyr Leu Phe Leu Val Ser Thr Phe Leu Phe Phe Lys Val
                85                  90                  95

Phe Leu Phe Val Leu
            100

<210> SEQ ID NO 80
<211> LENGTH: 175
<212> TYPE: PRT
<213> ORGANISM: Eutrema salsugineum

<400> SEQUENCE: 80

Met Ser Asp Trp Gly Pro Val Phe Val Ala Val Thr Leu Phe Val Leu
1               5                   10                  15

Leu Thr Pro Gly Val Leu Ile Gln Ile Pro Gly Lys Asn Arg Val Val
            20                  25                  30

Glu Phe Gly Thr Phe Gln Thr Ser Gly Val Ser Val Ile Val His Thr
        35                  40                  45

Leu Ile Tyr Phe Thr Leu Val Cys Ile Leu Leu Ala Leu Gln Ile
    50                  55                  60

His Ile Val Ile Val Lys Phe Leu Ser Phe Phe Leu Leu Glu Leu Cys
65                  70                  75                  80

Val Asn Ser Leu Phe Cys Leu Ala Pro Leu Ser Lys Gly Val Thr Phe
                85                  90                  95

Leu Pro Ser His Ser Gln Lys Thr Thr Thr Met Ala Asp Trp Ala Pro
            100                 105                 110

Val Leu Val Gly Val Ile Leu Phe Val Ile Leu Ser Pro Gly Leu Leu
        115                 120                 125

Phe Ser Leu Pro Gly Asn Asn Arg Ala Val Asp Phe Gly Thr Leu Lys
    130                 135                 140

Thr Asn Gly Lys Ala Ile Ala Val His Thr Leu Ile Phe Phe Ala Ile
145                 150                 155                 160

Tyr Ser Ile Leu Ile Leu Ala Val Asn Leu His Ile Tyr Thr Gly
                165                 170                 175

<210> SEQ ID NO 81
<211> LENGTH: 69
<212> TYPE: PRT
<213> ORGANISM: Aegilops tauschii

<400> SEQUENCE: 81

Met Ala Asp Trp Gly Pro Val Ile Val Ala Thr Val Leu Phe Val Leu
1               5                   10                  15
```

Leu Thr Pro Gly Leu Leu Cys Thr Leu Pro Gly Arg Gly Arg Val Ala
            20                  25                  30

Glu Phe Gly Ser Met His Thr Ser Gly Leu Ser Ile Leu Ile His Ala
            35                  40                  45

Val Leu Tyr Phe Ala Leu Val Thr Ile Phe Leu Ile Ala Val Gly Val
            50                  55                  60

His Val Tyr Thr Gly
65

<210> SEQ ID NO 82
<211> LENGTH: 69
<212> TYPE: PRT
<213> ORGANISM: Eutrema salsugineum

<400> SEQUENCE: 82

Met Ala Asp Trp Gly Pro Val Val Ala Val Ile Leu Phe Val Leu
1               5                   10                  15

Leu Thr Pro Gly Leu Leu Phe Gln Ile Pro Ala Arg Gly Arg Ile Val
            20                  25                  30

Glu Phe Gly Asn Met Gln Thr Ser Gly Ala Ser Ile Leu Val His Thr
            35                  40                  45

Ile Ile Tyr Phe Gly Leu Ile Thr Ile Phe Thr Ile Ala Ile Arg Leu
            50                  55                  60

His Ile Tyr Thr Gly
65

<210> SEQ ID NO 83
<211> LENGTH: 69
<212> TYPE: PRT
<213> ORGANISM: Citrus clementina

<400> SEQUENCE: 83

Met Ala Asp Trp Gly Pro Val Val Ile Ala Val Val Leu Phe Val Leu
1               5                   10                  15

Leu Ser Pro Gly Leu Leu Phe Gln Leu Pro Gly Arg Asn Arg Val Val
            20                  25                  30

Glu Phe Gly Asn Met His Thr Ser Gly Leu Ser Ile Leu Val His Thr
            35                  40                  45

Ile Ile Phe Phe Gly Leu Val Thr Ile Phe Leu Ile Ala Ile Gly Val
            50                  55                  60

His Ile His Thr Gly
65

<210> SEQ ID NO 84
<211> LENGTH: 69
<212> TYPE: PRT
<213> ORGANISM: Solanum tuberosum

<400> SEQUENCE: 84

Met Ala Asp Trp Gly Pro Val Ile Ala Val Val Leu Phe Val Leu
1               5                   10                  15

Leu Ser Pro Gly Leu Leu Phe Gln Leu Pro Gly Asn Asn Arg Val Val
            20                  25                  30

Gln Phe Ala Asn Phe Gln Thr Ser Gly Leu Ser Ile Phe Ile His Thr
            35                  40                  45

Ile Leu Phe Phe Gly Leu Ile Thr Ile Phe Leu Ile Ala Ile Gly Val
            50                  55                  60

His Ile Tyr Thr Gly

<210> SEQ ID NO 85
<211> LENGTH: 173
<212> TYPE: PRT
<213> ORGANISM: Theobroma cacao

<400> SEQUENCE: 85

Met Lys Arg Ser Glu Ile Arg Lys Asp Pro Thr Gln Asp Asn Arg Ser
1               5                   10                  15

Arg Trp Asn His Asn Thr Ser Ser Gly Glu Ser Ser His Val Arg Ser
            20                  25                  30

Leu Val Ser Arg His Pro Arg Ser Ile Gln Cys Glu Arg Asn Pro Ser
        35                  40                  45

Arg Phe Val Cys Ile Leu Cys Pro Ile Ser Phe Thr Leu Pro Ser Leu
    50                  55                  60

Phe Ser Ser Phe Leu Phe Pro Lys Pro Phe Ser His Ser Arg Cys Thr
65                  70                  75                  80

Leu Leu Phe Leu Leu Phe Ile Phe Ile Leu Ser Gly Lys Asn Gln
                85                  90                  95

Lys Pro Gln Gly Arg Gly Gln Met Ala Asp Trp Gly Pro Val Leu Val
            100                 105                 110

Ala Thr Val Leu Phe Val Leu Leu Ser Pro Gly Leu Leu Phe Gln Ile
        115                 120                 125

Pro Gly Arg Asn Lys Val Val Glu Phe Gly Asn Met Gln Thr Ser Gly
    130                 135                 140

Ala Ser Ile Leu Val His Ala Ile Ile Tyr Phe Gly Leu Ile Thr Ile
145                 150                 155                 160

Phe Cys Ile Ala Ile Gly Val His Ile Tyr Ala Ser Gln
                165                 170

<210> SEQ ID NO 86
<211> LENGTH: 70
<212> TYPE: PRT
<213> ORGANISM: Populus trichocarpa

<400> SEQUENCE: 86

Met Ala Asp Trp Gly Pro Val Ile Val Ala Val Leu Phe Val Leu
1               5                   10                  15

Leu Thr Pro Gly Leu Leu Phe Gln Ile Pro Gly Lys Ser Arg Val Val
            20                  25                  30

Glu Phe Gly Asn Met Gln Thr Ser Gly Ala Ser Ile Ala Val His Ala
        35                  40                  45

Ile Val Phe Ser Gly Leu Ile Thr Ile Phe Leu Val Ala Ile Gly Val
    50                  55                  60

His Ile Tyr Ala Ala Lys
65                  70

<210> SEQ ID NO 87
<211> LENGTH: 69
<212> TYPE: PRT
<213> ORGANISM: Solanum lycopersicum

<400> SEQUENCE: 87

Met Leu Asp Trp Gly Pro Val Leu Val Ser Val Ile Leu Phe Ile Leu
1               5                   10                  15

Leu Ser Pro Gly Leu Leu Phe Gln Leu Pro Gly His Arg His Cys Val
            20                  25                  30

Glu Phe Gly Asn Phe His Thr Ser Gly Ala Ser Ile Met Ile His Thr
                35                  40                  45

Leu Leu Tyr Phe Ala Leu Val Cys Val Phe Phe Leu Ala Val Lys Val
        50                  55                  60

His Leu Tyr Leu Gly
 65

<210> SEQ ID NO 88
<211> LENGTH: 70
<212> TYPE: PRT
<213> ORGANISM: Sorghum bicolor

<400> SEQUENCE: 88

Met Ser Asp Trp Gly Pro Val Val Ile Gly Leu Val Leu Phe Val Leu
 1               5                  10                  15

Leu Ser Pro Gly Leu Leu Ile Gln Leu Pro Gly Arg His His Phe Val
                20                  25                  30

Glu Phe Gly Asn Leu Gln Thr Ser Ala Val Ser Ile Leu Val His Ser
                35                  40                  45

Ile Ile Tyr Phe Ala Leu Ile Thr Ile Phe Val Ile Val Ile Gly Val
        50                  55                  60

His Ile Thr Thr Gly Asn
 65                  70

<210> SEQ ID NO 89
<211> LENGTH: 69
<212> TYPE: PRT
<213> ORGANISM: Oryza sativa Japonica Group

<400> SEQUENCE: 89

Met Ala Asp Trp Gly Pro Val Val Val Ala Thr Val Leu Phe Val Leu
 1               5                  10                  15

Leu Thr Pro Gly Leu Leu Cys Thr Val Pro Gly Arg Gly Arg Val Ala
                20                  25                  30

Glu Phe Gly Ser Phe His Thr Ser Gly Leu Ala Ile Ile Val His Ala
                35                  40                  45

Val Leu Tyr Phe Ala Leu Leu Thr Ile Phe Leu Ile Ala Ile Gly Val
        50                  55                  60

His Ile Tyr Ala Gly
 65

<210> SEQ ID NO 90
<211> LENGTH: 69
<212> TYPE: PRT
<213> ORGANISM: Phaseolus vulgaris

<400> SEQUENCE: 90

Met Ala Asp Trp Gly Pro Val Val Ile Ala Val Val Leu Phe Val Leu
 1               5                  10                  15

Leu Ser Pro Gly Leu Leu Phe Gln Leu Pro Gly Lys Asn Arg Val Val
                20                  25                  30

Glu Phe Gly Lys Met Gln Thr Ser Gly Val Ser Ile Leu Val His Thr
                35                  40                  45

Ile Ile Phe Phe Gly Leu Ile Thr Ile Phe Leu Ile Ala Ile Gly Val
        50                  55                  60

His Ile Asn Thr Gly
 65

```
<210> SEQ ID NO 91
<211> LENGTH: 69
<212> TYPE: PRT
<213> ORGANISM: Triticum urartu

<400> SEQUENCE: 91

Met Ala Asp Trp Gly Pro Val Ile Val Ala Thr Val Leu Phe Val Leu
1               5                   10                  15

Leu Thr Pro Gly Leu Leu Cys Thr Leu Pro Gly Arg Gly Arg Val Ala
            20                  25                  30

Glu Phe Gly Ser Met His Thr Ser Gly Leu Ser Leu Leu Ile His Ala
        35                  40                  45

Val Leu Tyr Phe Ala Leu Val Thr Ile Phe Leu Ile Ala Val Gly Val
    50                  55                  60

His Val Tyr Thr Gly
65

<210> SEQ ID NO 92
<211> LENGTH: 69
<212> TYPE: PRT
<213> ORGANISM: Hordeum vulgare subsp. vulgare

<400> SEQUENCE: 92

Met Ala Asp Trp Gly Pro Val Ile Val Ala Thr Val Leu Phe Val Leu
1               5                   10                  15

Leu Thr Pro Gly Leu Leu Cys Thr Leu Pro Gly Arg Gly Arg Val Ala
            20                  25                  30

Glu Phe Gly Ser Met His Thr Ser Gly Leu Ser Ile Leu Ile His Ala
        35                  40                  45

Val Leu Tyr Phe Ala Leu Val Thr Ile Phe Ile Ile Ala Val Gly Val
    50                  55                  60

His Val Tyr Thr Gly
65

<210> SEQ ID NO 93
<211> LENGTH: 138
<212> TYPE: PRT
<213> ORGANISM: Vitis vinifera

<400> SEQUENCE: 93

Met Gly Thr Gly Met Gly Thr Phe Pro Asp Pro Ala Ser Phe Phe Leu
1               5                   10                  15

Glu Ala Glu Ser Val Met Ala Asp Trp Gly Pro Val Leu Ile Ala Val
            20                  25                  30

Val Leu Phe Val Leu Leu Thr Pro Gly Leu Leu Phe Gln Val Pro Gly
        35                  40                  45

Lys Asn Arg Val Val Glu Phe Gly Ser Met His Thr Ser Gly Ala Ser
    50                  55                  60

Ile Leu Val His Thr Ile Ile Tyr Phe Gly Leu Ile Thr Ile Phe Leu
65                  70                  75                  80

Ile Ala Ile Gly Val His Ile Tyr Thr Asp Leu Gln Thr Leu Ala Ser
                85                  90                  95

Ile Cys Phe Lys Asn Arg Gly Asn Cys Met Ile Arg Lys Pro Val Pro
            100                 105                 110

His Ala Leu Lys Asn Arg Gly Leu Asp Asp Val Asn Leu Trp Arg Ser
        115                 120                 125

Thr Pro Gln Leu Pro Thr Trp His Tyr Pro
```

130             135

<210> SEQ ID NO 94
<211> LENGTH: 69
<212> TYPE: PRT
<213> ORGANISM: Prunus persica

<400> SEQUENCE: 94

Met Ala Asp Trp Gly Pro Val Val Ala Val Val Leu Phe Val Leu
1               5                   10                  15

Leu Ser Pro Gly Leu Leu Phe Gln Leu Pro Gly Arg Gly Arg Val Val
            20                  25                  30

Glu Phe Gly Ser Met His Thr Ser Gly Ile Ser Ile Leu Val His Thr
        35                  40                  45

Ile Ile Phe Phe Gly Leu Leu Thr Ile Phe Leu Ile Ala Ile Gly Val
    50                  55                  60

His Ile Tyr Thr Gly
65

<210> SEQ ID NO 95
<211> LENGTH: 71
<212> TYPE: PRT
<213> ORGANISM: Vitis vinifera

<400> SEQUENCE: 95

Met Ser Ala Asp Trp Gly Pro Ile Phe Val Ser Val Val Leu Phe Val
1               5                   10                  15

Leu Leu Ser Pro Gly Leu Leu Phe Gln Leu Pro Gly Ser Asn Arg Cys
            20                  25                  30

Val Glu Phe Gly Asn Leu Arg Thr Ser Gly Ala Ser Ile Met Leu His
        35                  40                  45

Ala Leu Leu Phe Phe Ala Leu Ile Cys Leu Phe Leu Leu Gly Phe Lys
    50                  55                  60

Ile His Leu Tyr Ile Gly Ser
65                  70

<210> SEQ ID NO 96
<211> LENGTH: 89
<212> TYPE: PRT
<213> ORGANISM: Arabidopsis thaliana

<400> SEQUENCE: 96

Met Ala Asp Trp Gly Pro Val Val Ala Val Ile Leu Phe Val Leu
1               5                   10                  15

Leu Thr Pro Gly Leu Leu Phe Gln Ile Pro Ala Arg Gly Arg Val Val
            20                  25                  30

Glu Phe Gly Asn Met Gln Thr Ser Gly Ala Ser Ile Leu Val His Thr
        35                  40                  45

Ile Ile Phe Phe Gly Leu Ile Thr Ile Phe Thr Ile Ala Ile Arg Leu
    50                  55                  60

His Ile Tyr Thr Gly Thr Arg Gln Leu Ala Leu Val Trp Phe Ile Gly
65                  70                  75                  80

Ile Arg Val Gln Ile Gly Ile Glu Tyr
                85

<210> SEQ ID NO 97
<211> LENGTH: 69
<212> TYPE: PRT
<213> ORGANISM: Glycine max

<400> SEQUENCE: 97

Met Ala Asp Trp Gly Pro Met Val Ile Ala Val Val Leu Phe Val Leu
1               5                   10                  15

Leu Ser Pro Gly Leu Leu Phe Gln Leu Pro Gly Lys Ser Lys Val Val
                20                  25                  30

Glu Phe Gly Asn Met Gln Thr Arg Ala Val Ser Ile Leu Val His Thr
            35                  40                  45

Ile Ile Phe Phe Gly Leu Ile Thr Ile Phe Leu Val Ala Ile Gly Val
        50                  55                  60

His Ile Tyr Thr Gly
65

<210> SEQ ID NO 98
<211> LENGTH: 70
<212> TYPE: PRT
<213> ORGANISM: Zea mays

<400> SEQUENCE: 98

Met Ser Asp Trp Gly Pro Val Val Ile Gly Leu Val Leu Phe Val Leu
1               5                   10                  15

Leu Ser Pro Gly Leu Leu Val Gln Leu Pro Gly Arg His His Leu Val
                20                  25                  30

Glu Phe Gly Asn Leu Lys Thr Ser Ala Val Ser Ile Leu Val His Ser
            35                  40                  45

Ile Ile Tyr Phe Ala Leu Ile Thr Leu Phe Val Ile Val Ile Gly Val
        50                  55                  60

His Ile Thr Thr Gly Asp
65                  70

<210> SEQ ID NO 99
<211> LENGTH: 69
<212> TYPE: PRT
<213> ORGANISM: Zea mays

<400> SEQUENCE: 99

Met Ala Asp Trp Gly Pro Val Ile Val Ala Thr Val Leu Phe Val Val
1               5                   10                  15

Leu Thr Pro Gly Leu Leu Cys Thr Leu Pro Gly Arg Gly Arg Val Ala
                20                  25                  30

Glu Phe Gly Ser Met His Thr Ser Gly Leu Ala Ile Leu Val His Ala
            35                  40                  45

Val Leu Tyr Phe Ala Leu Ile Thr Ile Phe Leu Ile Ala Ile Gly Ile
        50                  55                  60

His Val Tyr Ala Gly
65

<210> SEQ ID NO 100
<211> LENGTH: 142
<212> TYPE: PRT
<213> ORGANISM: Arabidopsis thaliana

<400> SEQUENCE: 100

Met Pro Asp Trp Gly Pro Val Phe Val Ala Val Thr Leu Phe Val Leu
1               5                   10                  15

Leu Thr Pro Gly Leu Leu Ile Gln Val Pro Gly Arg Gly Arg Val Val
                20                  25                  30

Glu Phe Gly Thr Phe Gln Thr Ser Gly Leu Ser Val Ile Val His Thr

```
              35                  40                  45
Leu Ile Tyr Phe Thr Leu Val Cys Ile Leu Leu Ala Leu Gln Ile
         50                  55                  60
His Ile Cys Asn Leu Phe Ser Thr Ser Met Ala Asp Trp Ala Pro Val
 65                  70                  75                  80
Leu Val Gly Val Val Leu Phe Val Ile Leu Ser Pro Gly Leu Leu Phe
                 85                  90                  95
Ser Leu Pro Gly Asn Asn Arg Thr Val Asp Phe Gly Gly Leu Lys Thr
                100                 105                 110
Asn Gly Lys Ala Ile Ala Val His Thr Leu Ile Phe Phe Ala Ile Tyr
                115                 120                 125
Thr Ile Leu Ile Leu Ala Leu Asn Leu His Ile Tyr Thr Gly
                130                 135                 140
```

<210> SEQ ID NO 101
<211> LENGTH: 142
<212> TYPE: PRT
<213> ORGANISM: Arabidopsis lyrata subsp. lyrata

<400> SEQUENCE: 101

```
Met Pro Asp Trp Gly Pro Val Phe Val Ala Val Thr Leu Phe Val Leu
 1               5                  10                  15
Leu Thr Pro Gly Leu Leu Ile Gln Val Pro Gly Arg Gly Arg Val Val
                 20                  25                  30
Glu Phe Gly Thr Phe Gln Thr Ser Gly Leu Ser Val Ile Val His Thr
                 35                  40                  45
Leu Ile Tyr Phe Thr Leu Val Cys Ile Leu Leu Ala Leu Gln Ile
         50                  55                  60
His Ile Cys Asn Leu Phe Ser Thr Ser Met Ala Asp Trp Ala Pro Val
 65                  70                  75                  80
Leu Val Gly Val Val Leu Phe Val Ile Leu Ser Pro Gly Leu Leu Phe
                 85                  90                  95
Ser Leu Pro Gly Asn Asn Arg Thr Val Asp Phe Gly Gly Leu Lys Thr
                100                 105                 110
Asn Gly Lys Ala Ile Ala Val His Thr Leu Ile Phe Phe Ala Ile Tyr
                115                 120                 125
Ser Ile Leu Ile Leu Ala Leu Asn Leu His Ile Tyr Thr Gly
                130                 135                 140
```

<210> SEQ ID NO 102
<211> LENGTH: 69
<212> TYPE: PRT
<213> ORGANISM: Genlisea aurea

<400> SEQUENCE: 102

```
Met Ala Asp Trp Gly Pro Val Leu Ile Ala Thr Val Leu Phe Val Leu
 1               5                  10                  15
Leu Thr Pro Gly Leu Leu Phe Gln Leu Pro Gly Arg Asn Arg Val Val
                 20                  25                  30
Asp Phe Gly Thr Met His Thr Ser Gly Leu Ser Ile Leu Val His Thr
                 35                  40                  45
Val Ile Tyr Phe Gly Leu Ile Thr Leu Leu Val Ala Val Gly Val
         50                  55                  60
His Ile Tyr Ala Gly
 65
```

```
<210> SEQ ID NO 103
<211> LENGTH: 69
<212> TYPE: PRT
<213> ORGANISM: Capsella rubella

<400> SEQUENCE: 103

Met Ala Asp Trp Gly Pro Val Val Ile Ala Val Ile Leu Phe Val Leu
1               5                   10                  15

Leu Thr Pro Gly Leu Leu Phe Gln Ile Pro Ala Arg Gly Arg Val Val
            20                  25                  30

Glu Phe Gly Asn Met Gln Thr Ser Gly Ala Ser Ile Leu Val His Thr
        35                  40                  45

Ile Ile Phe Phe Gly Leu Ile Thr Ile Phe Thr Ile Ala Ile Arg Leu
    50                  55                  60

His Ile Tyr Thr Gly
65

<210> SEQ ID NO 104
<211> LENGTH: 69
<212> TYPE: PRT
<213> ORGANISM: Aegilops tauschii

<400> SEQUENCE: 104

Met Ala Asp Trp Ala Pro Val Phe Ile Ala Leu Val Leu Phe Val Leu
1               5                   10                  15

Leu Ser Pro Gly Leu Leu Phe Gln Val Pro Gly Lys Asn Arg Phe Leu
            20                  25                  30

Glu Phe Gly Asn Lys Gln Thr Ser Gly Val Ser Val Leu Phe His Ala
        35                  40                  45

Val Ile Tyr Phe Ala Leu Ile Ala Ile Phe Thr Leu Ala Val Arg Val
    50                  55                  60

His Val Ile Leu Gly
65

<210> SEQ ID NO 105
<211> LENGTH: 69
<212> TYPE: PRT
<213> ORGANISM: Brachypodium distachyon

<400> SEQUENCE: 105

Met Ala Asp Trp Gly Pro Val Ile Val Ala Thr Val Leu Phe Val Leu
1               5                   10                  15

Leu Thr Pro Gly Leu Leu Cys Thr Leu Pro Gly Arg Gly Arg Val Ala
            20                  25                  30

Glu Phe Gly Ser Met His Thr Thr Gly Leu Ala Ile Leu Val His Ala
        35                  40                  45

Val Leu Tyr Phe Ala Leu Ala Thr Ile Phe Leu Ile Ala Ile Gly Val
    50                  55                  60

His Val Tyr Thr Gly
65
```

MATERIALS AND METHODS TO INCREASE PLANT GROWTH AND YIELD

REFERENCE TO RELATED APPLICATIONS

This application is a continuation-in-part of U.S. patent application Ser. No. 14/152,865, filed Jan. 10, 2014, which claims the benefit of U.S. provisional application No. 61/751,648, filed Jan. 11, 2013, each of which is incorporated herein by reference in its entirety.

STATEMENT OF GOVERNMENT SUPPORT

This invention was made with government support under grant number DE-FG02-05ER64114 awarded by the U.S. Department of Energy. The government has certain rights in the invention.

INCORPORATION OF SEQUENCE LISTING

The sequence listing that is contained in the file named "UFFL042USCP1_ST25.txt," which is 78.2 kilobytes as measured in Microsoft Windows operating system and was created on Jul. 11, 2014, is filed electronically herewith and incorporated herein by reference.

FIELD OF THE INVENTION

The invention relates generally to the field of molecular biology and genetics. More particularly, the invention relates to methods of increasing growth and yield of plants.

BACKGROUND OF THE INVENTION

Water deficit and drought are the main factors that limit crop production and productivity, and are a major threat to food security worldwide. Plant varieties can be bred to be more productive per unit of water supplied, i.e., higher water-use efficiency (WUE). However, our lack of knowledge of the genetic mechanisms underlying WUE has hindered the improvement of this trait. Water-use efficiency may be impacted by a number of factors, including stomatal conductance, which is partially regulated by hydraulic conductivity. Hydraulic conductivity increases rapidly with greater xylem vessel diameter because flow is proportional to the fourth power of conduit diameter. Genes that regulate meristematic cell differentiation into vessels were unknown until recently, but their manipulation could increase hydraulic conductivity and, consequently, the photosynthetic rate and plant productivity.

BRIEF SUMMARY OF THE INVENTION

The subject invention concerns materials and methods for modulating growth rates, yield, and/or drought resistance in plants. In one embodiment, a method of the invention comprises upregulating expression of a hydraulic conductivity 1 (hc1) gene (or a homolog thereof that provides for substantially the same activity), or increasing expression or activity of the protein encoded by an hc1 gene thereof, in a plant, wherein increased expression of the hc1 gene or increased expression or activity of the protein encoded by an hc1 gene results in increased growth in the plant. In one embodiment, the hc1 gene encodes a protein comprising the amino acid sequence shown in SEQ ID NOs:2, 4 or 7-105, or a fragment or variant thereof having substantially the same activity. In a specific embodiment, the hc1 gene comprises the nucleotide sequence shown in SEQ ID NO:1 or SEQ ID NO:3. In one embodiment, a plant is transformed with a polynucleotide encoding an Hc1 protein, or a fragment or variant thereof having substantially the same activity, wherein the Hc1 protein is expressed in the plant.

In another embodiment, a method of the invention provides for increased expression of an hc1 gene of the invention (or a homolog thereof that provides for substantially the same activity), or increased expression or activity of a protein encoded by the hc1 gene (or a homolog thereof). In one embodiment, multiple copies of an hc1 gene of the invention, or a protein encoding portion thereof, are incorporated in a plant. In one embodiment, the hc1 gene encodes a protein comprising the amino acid sequence shown in SEQ ID NOs:2, 4 or 7-105, or a fragment or variant thereof having substantially the same activity. In a specific embodiment, the hc1 gene comprises the nucleotide sequence shown in SEQ ID NO:1 or SEQ ID NO:3.

In one aspect, the invention provides methods for modulating growth rate, yield, and/or resistance to drought conditions in a plant, comprising modulating expression of an hc1 gene, and/or modulating expression and/or activity of a protein encoded by an hc1 gene, wherein said hc1 gene comprises a nucleotide sequence encoding a polypeptide comprising the amino acid sequence any of SEQ ID NOs:2, 4, or 7-105, or a fragment thereof having substantially the same biological activity. In some embodiments, expression of said hc1 gene and/or expression or activity of a protein encoded by said hc1 gene is up-regulated in said plant. In other embodiments, said plant is of the genus *Abies, Acacia, Acer, Aegilops, Aesculus, Ailanthus, Alnus, Amborella, Amelanchier, Arabidopsis, Arbutus, Arctostaphylos, Artemisia, Asiminia, Atriplex, Aucuba, Berberis, Betula, Brachypodium, Buddleia, Buxus, Calocedrus, Camellia, Campsis, Capsella, Carpinus, Carya, Castanea, Catalpa, Ceanothus, Cedrus, Celastrus, Celtis, Cephalanthus, Cercidium, Cercis, Chaenomeles, Chamaecyparis, Chilopsis, Chionanthus, Chrysothamnus, Cicer, Cistus, Citrus, Cladrastis, Clematis, Coleogynia, Cornus, Corylus, Cotinus, Cotoneaster, Cowania, Crataegus, Crataegus, Cucumis, Cupressus, Cytisus, Daphne, Deutzia, Diospyros, Elaeagnus, Ephedra, Erythranthe, Escallonia, Eucalyptus, Euonymus, Eutrema, Fagus, Forsythia, Fragaria, Fraxinus, Gaultheria, Genlisea, Ginkgo, Gleditsia, Glycine, Grevillea, Gymnocladus, Hamamelis, Hebe, Hibiscus, Hordeum, Hydrangea, Hypericum, Ilex, Juglans, Juniperus, Kalmia, Kerria, Koelreuteria, Lagerstroemia, Larix, Larrea, Libocedrus, Ligustrum, Liquidambar, Liriodendron, Lonicera, Lotus, Maclura, Magnolia, Mahonia, Malus, Medicago, Menispermum, Morus, Myrica, Nyssa, Oryza, Osmanthus, Ostrya, Oxydendron, Parthenocissus, Phaseolus, Philadelphus, Photinia, Physocarpus, Picea, Pinus, Pittosporum, Platanus, Populus, Prosopis, Prunus, Pseudotsuga, Ptelea, Purshia, Pyrus, Quercus, Rhamnus, Rhaphiolepis, Rhododendron, Rhus, Ribes, Ricinus, Robinia, Rosa, Rubus, Salix, Sambucus, Sassafras, Sequoia, Setaria, Shepherdia, Smilax, Solanum, Sophora, Sorbus, Sorghum, Spiraea, Staphylea, Stewartia, Symphoricarpos, Syringa, Taxodium, Taxus, Theobroma, Thuja, Tilia, Triticum, Tsuga, Ulmus, Umbellularia, Vaccinium, Viburnum, Vitis, Zanthoxylum, Zea,* or *Zelkova.*

In some embodiments, said plant is transformed with a polynucleotide that is stably incorporated into the genome of the plant, wherein expression of the polynucleotide up-regulates expression of said hc1 gene, and/or up-regulates expression and/or activity of said protein encoded by said hc1 gene.

In other embodiments, a heterologous regulatory element has been inserted into the genome of said plant, wherein said heterologous regulatory element modulates expression of said hc1 gene. In some embodiments, said heterologous regulatory element is a promoter, for example a promoter inserted into the plant genome within about 2 kbp of said hc1 gene. In certain embodiments, said promoter is a cauliflower mosaic virus 35S promoter, an enhanced CaMV 35S promoter, a CaMV 19S promoter, a cassava vein mosaic virus promoter, a prolifera promoter, an Ap3 promoter, a heat shock promoter, a T-DNA 1'- or 2'-promoter of *A. tumefaciens*, a polygalacturonase promoter, achalcone synthase A (CHS-A) promoter, a PR-1α promoter, a ubiquitin promoter, an actin promoter, a alcA gene promoter, a pin2 promoter, a maize WipI promoter, a maize trpA gene promoter, a maize CDPK gene promoter, a RUBISCO SSU promoter, a Cald5H promoter, a SAD promoter, a XCP1 promoter, a CAD promoter, a CesA1 promoter, a CesA2 promoter, a CesA3 promoter, a tubulin gene (TUB) promoter, a lipid transfer protein gene (LTP) promoter, a coumarate-4-hydroxylase gene (C4H) promoter, a Cab1 promoter, a Cab19 promoter, a PPDK promoter, a ribulose biphosphate carboxylase (RBCS) promoter, an Act1 promoter, an AS-1 promoter, a RBC-3A promoter, a Figwort Mosaic Virus (FMV) promoter, a mannopine synthase (mas) promoter, an octopine synthase (ocs) promoter, a nos promoter, an Adh promoter, a sucrose synthase promoter, an α-tubulin promoter, an actin promoter, a cab promoter, a PEPCase promoter, a promoter associated with the R gene complex, a 4-coumarate Co-enzyme A ligase (4CL) promoter, a β-phaseolin promoter, a glycinin promoter, or a MEG1 promoter.

In yet other embodiments, said heterologous regulatory element is an enhancer. In some embodiments, said enhancer is a CaMV 35S enhancer, a SV40 enhancer, a maize shrunken-1 enhancer, PetE enhancer, or a rice α-amylase enhancer.

In another aspect, the invention provides a transformed or transgenic plant, plant tissue, or plant cell having increased growth rate, yield, and/or resistance to drought conditions, wherein expression of an hc1 gene, and/or function and/or activity of a protein encoded by an hc1 gene is increased, wherein said hc1 gene comprises a nucleotide sequence encoding a polypeptide comprising the amino acid sequence any of SEQ ID NOs:2, 4, or 7-105, or a fragment thereof having substantially the same biological activity. In some embodiments, expression of said hc1 gene and/or expression or activity of said protein encoded by an hc1 gene is up-regulated in the plant. In certain embodiments, said plant is of the genus *Abies, Acacia, Acer, Aegilops, Aesculus, Ailanthus, Alnus, Amborella, Amelanchier, Arabidopsis, Arbutus, Arctostaphylos, Artemisia, Asiminia, Atriplex, Aucuba, Berberis, Betula, Brachypodium, Buddleia, Buxus, Calocedrus, Camellia, Campsis, Capsella, Carpinus, Carya, Castanea, Catalpa, Ceanothus, Cedrus, Celastrus, Celtis, Cephalanthus, Cercidium, Cercis, Chaenomeles, Chamaecyparis, Chilopsis, Chionanthus, Chrysothamnus, Cicer, Cistus, Citrus, Cladrastis, Clematis, Coleogynia, Cornus, Corylus, Cotinus, Cotoneaster, Cowania, Crataegus, Crataegus, Cucumis, Cupressus, Cytisus, Daphne, Deutzia, Diospyros, Elaeagnus, Ephedra, Erythranthe, Escallonia, Eucalyptus, Euonymus, Eutrema, Fagus, Forsythia, Fragaria, Fraxinus, Gaultheria, Genlisea, Ginkgo, Gleditsia, Glycine, Grevillea, Gymnocladus, Hamamelis, Hebe, Hibiscus, Hordeum, Hydrangea, Hypericum, Ilex, Juglans, Juniperus, Kalmia, Kerria, Koelreuteria, Lagerstroemia, Larix, Larrea, Libocedrus, Ligustrum, Liquidambar, Liriodendron, Lonicera, Lotus, Maclura, Magnolia, Mahonia, Malus, Medicago, Menispermum, Morus, Myrica, Nyssa, Oryza, Osmanthus, Ostrya, Oxydendron, Parthenocissus, Phaseolus, Philadelphus, Photinia, Physocarpus, Picea, Pinus, Pittosporum, Platanus, Populus, Prosopis, Prunus, Pseudotsuga, Ptelea, Purshia, Pyrus, Quercus, Rhamnus, Rhaphiolepis, Rhododendron, Rhus, Ribes, Ricinus, Robinia, Rosa, Rubus, Salix, Sambucus, Sassafras, Sequoia, Setaria, Shepherdia, Smilax, Solanum, Sophora, Sorbus, Sorghum, Spiraea, Staphylea, Stewartia, Symphoricarpos, Syringa, Taxodium, Taxus, Theobroma, Thuja, Tilia, Triticum, Tsuga, Ulmus, Umbellularia, Vaccinium, Viburnum, Vitis, Zanthoxylum, Zea*, or *Zelkova*.

In some embodiments, said plant is transformed with a polynucleotide that is stably incorporated into the genome of the plant, wherein expression of the polynucleotide up-regulates expression of said hc1 gene, and/or up-regulates expression and/or activity of said protein encoded by the hc1 gene.

In other embodiments, a heterologous regulatory element has been inserted into the genome of said plant, wherein said heterologous regulatory element modulates expression of said hc1 gene. In some embodiments, said heterologous regulatory element is a promoter, for example a promoter inserted into the plant genome within about 2 kbp of said hc1 gene. In certain embodiments, said promoter is a cauliflower mosaic virus 35S promoter, an enhanced CaMV 35S promoter, a CaMV 19S promoter, a cassava vein mosaic virus promoter, a prolifera promoter, an Ap3 promoter, a heat shock promoter, a T-DNA 1'- or 2'-promoter of *A. tumefaciens*, a polygalacturonase promoter, achalcone synthase A (CHS-A) promoter, a PR-1α promoter, a ubiquitin promoter, an actin promoter, a alcA gene promoter, a pin2 promoter, a maize WipI promoter, a maize trpA gene promoter, a maize CDPK gene promoter, a RUBISCO SSU promoter, a Cald5H promoter, a SAD promoter, a XCP1 promoter, a CAD promoter, a CesA1 promoter, a CesA2 promoter, a CesA3 promoter, a tubulin gene (TUB) promoter, a lipid transfer protein gene (LTP) promoter, a coumarate-4-hydroxylase gene (C4H) promoter, a Cab1 promoter, a Cab19 promoter, a PPDK promoter, a ribulose biphosphate carboxylase (RBCS) promoter, an Act1 promoter, an AS-1 promoter, a RBC-3A promoter, a Figwort Mosaic Virus (FMV) promoter, a mannopine synthase (mas) promoter, an octopine synthase (ocs) promoter, a nos promoter, an Adh promoter, a sucrose synthase promoter, an α-tubulin promoter, an actin promoter, a cab promoter, a PEPCase promoter, a promoter associated with the R gene complex, a 4-coumarate Co-enzyme A ligase (4CL) promoter, a β-phaseolin promoter, a glycinin promoter, or a MEG1 promoter.

In yet other embodiments, said heterologous regulatory element is an enhancer. In some embodiments, said enhancer is a CaMV 35S enhancer, a SV40 enhancer, a maize shrunken-1 enhancer, PetE enhancer, or a rice α-amylase enhancer.

In yet another aspect, the invention provides methods for preparing a transformed or transgenic plant, plant tissue, or plant cell having increased growth rate, yield, and/or resistance to drought conditions comprising incorporating a polynucleotide in a cell of the plant, wherein expression of the polynucleotide increases expression of an hc1 gene, and/or increases the function and/or activity of a protein encoded by an hc1 gene in the plant, wherein said hc1 gene comprises a nucleotide sequence encoding a polypeptide comprising the amino acid sequence any of SEQ ID NOs:2, 4, or 7-105, or a fragment thereof having substantially the same biological activity. In some embodiments, expression of said hc1 gene and/or expression or activity of said protein encoded by an hc1 gene is up-regulated. In other embodiments, said plant is of the genus *Abies, Acacia, Acer, Aegilops, Aesculus, Ailanthus, Alnus, Amborella, Amelanchier, Arabidopsis, Arbutus, Arctostaphylos, Artemisia, Asiminia, Atriplex, Aucuba, Berberis, Betula, Brachypodium, Buddleia, Buxus, Calocedrus, Camellia, Campsis, Capsella, Carpinus, Carya, Castanea, Catalpa, Ceanothus, Cedrus, Celastrus, Celtis, Cephalanthus, Cercidium, Cercis, Chaenomeles, Chamaecyparis, Chilopsis, Chionanthus, Chrysothamnus, Cicer, Cistus, Citrus, Cladrastis, Clematis, Coleogynia, Cornus, Corylus, Cotinus, Cotoneaster, Cowania, Crataegus, Crataegus, Cucumis, Cupressus, Cytisus, Daphne, Deutzia, Diospyros, Elaeagnus, Ephedra, Erythranthe, Escallonia, Eucalyptus, Euonymus, Eutrema, Fagus, Forsythia, Fragaria, Fraxinus, Gaultheria, Genlisea, Ginkgo, Gleditsia, Glycine, Grevillea, Gymnocladus, Hamamelis, Hebe, Hibiscus, Hordeum, Hydrangea, Hypericum, Ilex, Juglans, Juniperus, Kalmia, Kerria, Koelreuteria, Lagerstroemia, Larix, Larrea, Libocedrus, Ligustrum, Liquidambar, Liriodendron, Lonicera, Lotus, Maclura, Magnolia, Mahonia, Malus, Medicago, Menispermum, Morus, Myrica, Nyssa, Oryza, Osmanthus, Ostrya, Oxydendron, Parthenocissus, Phaseolus, Philadelphus, Photinia, Physocarpus, Picea, Pinus, Pittosporum, Platanus, Populus, Prosopis, Prunus, Pseudotsuga, Ptelea, Purshia, Pyrus, Quercus, Rhamnus, Rhaphiolepis, Rhododendron, Rhus, Ribes, Ricinus, Robinia, Rosa, Rubus, Salix, Sambucus, Sassafras, Sequoia, Setaria, Shepherdia, Smilax, Solanum, Sophora, Sorbus, Sorghum, Spiraea, Staphylea, Stewartia, Symphoricarpos, Syringa, Taxodium, Taxus, Theobroma, Thuja, Tilia, Triticum, Tsuga, Ulmus, Umbellularia, Vaccinium, Viburnum, Vitis, Zanthoxylum, Zea,* or *Zelkova.*

In some embodiments, said plant is transformed with a polynucleotide that is stably incorporated into the genome of the plant, wherein expression of said polynucleotide up-regulates expression of said hc1 gene, and/or up-regulates expression and/or activity of said protein encoded by said hc1 gene.

In other embodiments, a heterologous regulatory element has been inserted into the genome of the plant, wherein said heterologous regulatory element modulates expression of said hc1 gene. In some embodiments, said heterologous regulatory element is a promoter, for example a promoter inserted into the plant genome within about 2 kbp of said hc1 gene. In certain embodiments, said promoter is a cauliflower mosaic virus 35S promoter, an enhanced CaMV 35S promoter, a CaMV 19S promoter, a cassava vein mosaic virus promoter, a prolifera promoter, an Ap3 promoter, a heat shock promoter, a T-DNA 1'- or 2'-promoter of *A. tumefaciens*, a polygalacturonase promoter, achalcone synthase A (CHS-A) promoter, a PR-1α promoter, a ubiquitin promoter, an actin promoter, a alcA gene promoter, a pin2 promoter, a maize WipI promoter, a maize trpA gene promoter, a maize CDPK gene promoter, a RUBISCO SSU promoter, a Cald5H promoter, a SAD promoter, a XCP1 promoter, a CAD promoter, a CesA1 promoter, a CesA2 promoter, a CesA3 promoter, a tubulin gene (TUB) promoter, a lipid transfer protein gene (LTP) promoter, a coumarate-4-hydroxylase gene (C4H) promoter, a Cab1 promoter, a Cab19 promoter, a PPDK promoter, a ribulose biphosphate carboxylase (RBCS) promoter, an Act1 promoter, an AS-1 promoter, a RBC-3A promoter, a Figwort Mosaic Virus (FMV) promoter, a mannopine synthase (mas) promoter, an octopine synthase (ocs) promoter, a nos promoter, an Adh promoter, a sucrose synthase promoter, an α-tubulin promoter, an actin promoter, a cab promoter, a PEPCase promoter, a promoter associated with the R gene complex, a 4-coumarate Co-enzyme A ligase (4CL) promoter, a β-phaseolin promoter, a glycinin promoter, or a MEG1 promoter.

In yet other embodiments, said heterologous regulatory element is an enhancer. In some embodiments, said enhancer is a CaMV 35S enhancer, a SV40 enhancer, a maize shrunken-1 enhancer, PetE enhancer, or a rice α-amylase enhancer.

BRIEF DESCRIPTION OF THE SEQUENCES

Figure 1:
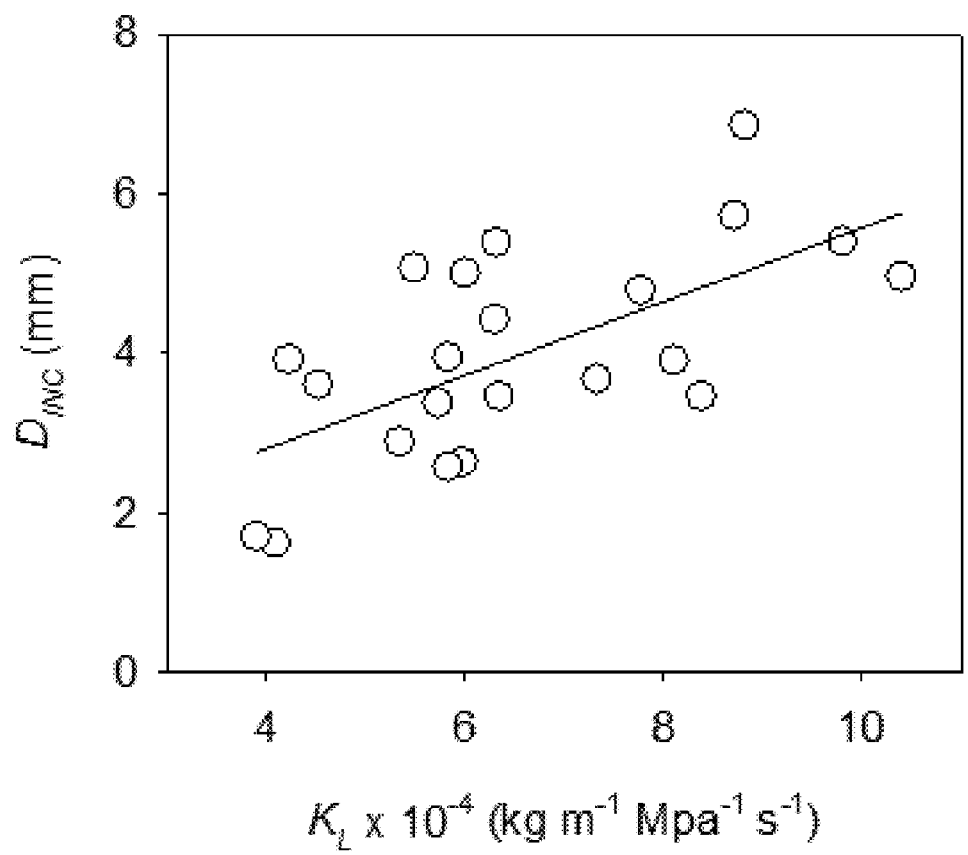
FIG. 1—Shows a linear regression plot demonstrating the positive association ($r^2$=0.4164, P=0.0012) between leaf-specific hydraulic conductivity ($K_L$) and diameter increment ($D_{INC}$). Points are progeny genotype means.

SEQ ID NO:1—Nucleotide sequence of the coding region of an hc1 gene that encodes the amino acid sequence of SEQ ID NO:2.

SEQ ID NO:2—Amino acid sequence of a protein encoded by an hc1 gene having the nucleotide sequence of SEQ ID NO:1.

SEQ ID NO:3—Genomic nucleotide sequence that comprises the coding region of an hc1 gene that encodes the amino acid sequence of SEQ ID NO:2.

SEQ ID NO: 4—Amino acid sequence of a protein encoded by a poplar hc1 gene.

SEQ ID NO: 5—A conserved motif within protein sequences encoded by hc1 genes.

SEQ ID NO: 6—A conserved motif within protein sequences encoded by hc1 genes.

SEQ ID NOs: 7-105—Homologs of the poplar HC1 sequence having SEQ ID NO: 4.

DETAILED DESCRIPTION OF THE INVENTION

The subject invention concerns materials and methods for modulating plant biomass and yield. In one aspect, the invention concerns materials and methods for increasing growth rates and/or biomass in plants. The subject invention also provides for improved resistance to drought conditions in a plant. In one embodiment, a method of the invention comprises increasing expression of an hc1 gene (or a homolog thereof that provides for substantially the same activity), or the protein encoded by an hc1 gene thereof, in a plant, wherein expression of the hc1 gene results in increased biomass levels in the plant (relative to biomass levels of a plant having lower levels of hc1 expression). In one embodiment, the hc1 gene encodes a protein comprising the amino acid sequence shown in SEQ ID NOs:2, 4, or 7-105, or a fragment or variant thereof having substantially the same activity as a full-length sequence. In a specific embodiment, the hc1 gene comprises the nucleotide sequence shown in SEQ ID NO:1 or SEQ ID NO:3. In one embodiment, a plant is transformed with a polynucleotide encoding an Hc1 protein, or a fragment or variant thereof having substantially the same activity, wherein the Hc1 protein is expressed in the plant.

In another embodiment, a method of the invention provides for increased expression of an hc1 gene of the invention (or a homolog thereof that provides for substantially the same activity), or a protein encoding portion thereof. In one embodiment, multiple copies of an hc1 gene of the invention, or a protein encoding portion thereof, are incorporated in a plant. In one embodiment, the hc1 gene encodes a protein comprising the amino acid sequence shown in SEQ ID NOs:2, 4, or 7-105, or a fragment or variant thereof having substantially the same activity as a full-length sequence. In a specific embodiment, the hc1 gene comprises the nucleotide sequence shown in SEQ ID NO:1 or SEQ ID NO:3.

In one embodiment, a heterologous hc1-encoding polynucleotide is incorporated into a plant and the polynucleotide expressed therein. In one embodiment, the Hc1 protein encoded by the polynucleotide comprises the amino acid sequence shown in SEQ ID NOs:2, 4, or 7-105, or a fragment or variant thereof having substantially the same activity as a full-length sequence. In a further embodiment, the polynucleotide comprises the nucleotide sequence shown in SEQ ID NO:1 or SEQ ID NO:3. The polynucleotide can comprise regulatory elements such as promoters, etc. that provide for increased expression of the hc1 in the plant.

In another embodiment, a method of the invention comprises introducing a polynucleotide into a plant wherein the polynucleotide, or the expression product thereof, provides for increased expression of an hc1 gene or protein relative to a plant wherein the polynucleotide has not been introduced (e.g., a wildtype plant). In another embodiment, a polynucleotide can be introduced that encodes an Hc1 protein that exhibits increased activity. In a further embodiment, a polynucleotide can be introduced that encodes a protein having Hc1 activity, wherein the polynucleotide comprises regulatory elements that provide for increased expression of the polynucleotide and/or the protein encoded thereby. Plants containing the polynucleotide, or progeny thereof, optionally can be screened for increased expression of the hc1 gene and/or protein, or increased activity of the protein.

The subject invention also concerns isolated polynucleotides encoding the gene product of an hc1 gene of *Populus*, or a homolog thereof having substantially the same activity. In one embodiment, the polynucleotide encodes a protein comprising the amino acid sequence shown in SEQ ID NOs:2, 4, or 7-105, or a fragment or variant thereof having substantially the same activity. In a specific embodiment, the polynucleotide comprises the nucleotide sequence shown in SEQ ID NO:1 or SEQ ID NO:3.

The subject invention also concerns plants, plant tissue, and plant cells of the invention that exhibit increased expression of an hc1 gene (or homolog thereof) or the protein encoded thereby. In one embodiment, the plant, plant tissue, or plant cell is a woody tree. Plants contemplated within the scope of the present invention include, but are not limited to, plants of the genus *Abies, Acacia, Acer, Aesculus, Ailanthus, Alnus, Amelanchier, Arbutus, Arctostaphylos, Artemisia, Asiminia, Atriplex, Aucuba, Berberis, Betula, Buddleia, Buxus, Calocedrus, Camellia, Campsis, Carpinus, Carya, Castanea, Catalpa, Ceanothus, Cedrus, Celastrus, Celtis, Cephalanthus, Cercidium, Cercis, Chaenomeles, Chamaecyparis, Chilopsis, Chionanthus, Chrysothamnus, Cistus, Cladrastis, Clematis, Coleogynia, Cornus, Corylus, Cotinus, Cotoneaster, Cowania, Crataegus, Crataegus, Cupressus, Cytisus, Daphne, Deutzia, Diospyros, Elaeagnus, Ephedra, Escallonia, Eucalyptus, Euonymus, Fagus, Forsythia, Fraxinus, Gaultheria, Ginkgo, Gleditsia, Grevillea, Gymnocladus, Hamamelis, Hebe, Hibiscus, Hydrangea, Hypericum, Ilex, Juglans, Juniperus, Kalmia, Kerria, Koelreuteria, Lagerstroemia, Larix, Larrea, Libocedrus, Ligustrum, Liquidambar, Liriodendron, Lonicera, Maclura, Magnolia, Mahonia, Malus, Menispermum, Morus, Myrica, Nyssa, Osmanthus, Ostrya, Oxydendron, Parthenocissus, Philadelphus, Photinia, Physocarpus, Picea, Pinus, Pittosporum, Platanus, Populus, Prosopis, Prunus, Pseudotsuga, Ptelea, Purshia, Pyrus, Quercus, Rhamnus, Rhaphiolepis, Rhododendron, Rhus, Ribes, Robinia, Rosa, Rubus, Salix, Sambucus, Sassafras, Sequoia, Shepherdia, Smilax, Sophora, Sorbus, Spiraea, Staphylea, Stewartia, Symphoricarpos, Syringa, Taxodium, Taxus, Thuja, Tilia, Tsuga, Ulmus, Umbellularia, Vaccinium, Viburnum, Vitis, Zanthoxylum,* and *Zelkova*. Plants contemplated within the scope of the present invention further include, but are not limited to, plants of the genus *Aegilops, Amborella, Arabidopsis, Brachypodium, Capsella, Cicer, Citrus, Cucumis, Erythranthe, Eutrema, Fragaria, Genlisea, Glycine, Hordeum, Lotus, Medicago, Oryza, Phaseolus, Ricinus, Setaria, Solanum, Sorghum, Theobroma, Triticum,* and *Zea*.

Plant species contemplated within the scope of the present invention include, but are not limited to, *Aegilops tauschii, Amborella trichopoda, Arabidopsis lyrata* subsp. *lyrata, Arabidopsis thaliana, Brachypodium distachyon, Capsella rubella, Cicer arietinum, Citrus clementina, Citrus sinensis, Cucumis sativus, Erythranthe guttata, Eucalyptus grandis, Eutrema salsugineum, Fragaria vesca* subsp. *vesca, Genlisea aurea, Glycine max, Hordeum vulgare* subsp. *vulgare, Lotus japonicus, Medicago truncatula, Morus notabilis, Oryza sativa Japonica Group, Phaseolus vulgaris, Populus trichocarpa, Prunus persica, Ricinus communis, Setaria italica, Solanum lycopersicum, Solanum tuberosum, Sorghum bicolor, Theobroma cacao, Triticum urartu, Vitis vinifera,* and *Zea mays*.

The plant, plant tissue, or plant cell of the invention can be a hybrid plant or from a hybrid plant. Plants of the invention can have increased growth rates, biomass, and/or improved resistance to drought conditions. In one embodiment, a plant of the invention exhibits increased expression of hc1. In one embodiment, a plant comprises one or more mutations introduced into an hc1 gene of a plant that results in increased transcription of the hc1 gene, or increased translation of hc1 mRNA, and/or that results in an Hc1 protein exhibiting increased activity or function. In one embodiment, a plant, plant tissue, or plant cell comprises a heterologous polynucleotide that encodes a protein comprising the amino acid sequence shown in SEQ ID NOs:2, 4, or 7-105, or a fragment or variant thereof having substantially the same activity. In a specific embodiment, the heterologous polynucleotide comprises the nucleotide sequence shown in SEQ ID NO:1 or SEQ ID NO:3. In one embodiment, a plant, plant tissue, or plant cell of the invention is a transgenic plant, plant tissue, or plant cell that exhibits increased expression of hc1. In another embodiment, a plant, plant tissue, or plant cell of the invention is one that has been obtained through a breeding program.

Optionally, the plants of the present invention may also further exhibit one or more agronomic traits that primarily are of benefit to a seed company, a grower, or a grain processor, for example, herbicide resistance, virus resistance, bacterial pathogen resistance, insect resistance, nematode resistance, and fungal resistance. See, e.g., U.S. Pat. Nos. 5,569,823; 5,304,730; 5,495,071; 6,329,504; and 6,337,431. Such a trait may also be one that increases plant vigor or yield (including traits that allow a plant to grow at different temperatures, soil conditions and levels of sunlight and precipitation), or one that allows identification of a plant exhibiting a trait of interest (e.g., selectable marker gene, seed coat color, etc.). Various traits of interest, as well as methods for introducing these traits into a plant, are described, for example, in U.S. Pat. Nos. 5,569,823; 5,304, 730; 5,495,071; 6,329,504; 6,337,431; 5,767,366; 5,928, 937; 4,761,373; 5,013,659; 4,975,374; 5,162,602; 4,940, 835; 4,769,061; 5,554,798; 5,879,903; 5,276,268; 5,561, 236; 4,810,648; and 6,084,155; in European application No. 0242246; in U.S. Patent Application Publication No. 2001/ 0016956; and on the worldwide web at lifesci.sussex.ac.uk/ home/Neil_Crickmore/Bt/.

Polynucleotides useful in the present invention can be provided in an expression construct. Expression constructs of the invention generally include regulatory elements that are functional in the intended host cell in which the expression construct is to be expressed. Thus, a person of ordinary skill in the art can select regulatory elements for use in bacterial host cells, yeast host cells, plant host cells, insect host cells, mammalian host cells, and human host cells. Regulatory elements include promoters, transcription termination sequences, translation termination sequences, enhancers, and polyadenylation elements. As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

An expression construct of the invention can comprise a promoter sequence operably linked to a polynucleotide sequence encoding a polypeptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site in the expression construct as it is from the transcription start site in its natural genetic environment. Some variation in this distance is permitted without substantial decrease in promoter activity. A transcription start site is typically included in the expression construct.

If the expression construct is to be provided in or introduced into a plant cell, then plant viral promoters, such as, for example, a cauliflower mosaic virus (CaMV) 35S (including the enhanced CaMV 35S promoter (see, for example U.S. Pat. No. 5,106,739)) or a CaMV 19S promoter or a cassava vein mosaic can be used. Other promoters that can be used for expression constructs in plants include, for example, prolifera promoter, Ap3 promoter, heat shock promoters, T-DNA 1'- or 2'-promoter of *A. tumefaciens*, polygalacturonase promoter, chalcone synthase A (CHS-A) promoter from *petunia*, tobacco PR-1α promoter, ubiquitin promoter, actin promoter, alcA gene promoter, pin2 promoter (Xu et al., 1993), maize WipI promoter, maize trpA gene promoter (U.S. Pat. No. 5,625,136), maize CDPK gene promoter, and RUBISCO SSU promoter (U.S. Pat. No. 5,034,322) can also be used. Tissue-specific promoters, for example xylem-specific promoters, such as the promoter of Cald5H, SAD, XCP1, CAD, CesA1, CesA2, CesA3, tubulin gene (TUB) promoter, lipid transfer protein gene (LTP) promoter, or coumarate-4-hydroxylase gene (C4H) promoter (see, for example, Lu et al., 2008; Funk et al., 2002; Sibout et al., 2005; published U.S. Application No. 2008/ 0196125) can be used. Leaf-specific promoters that can be used in a nucleic acid construct of the invention include Cab1 promoter (Brusslan and Tobin, 1992), Cab19 promoter (Bassett et al., 2007), PPDK promoter (Matsuoka et al., 1993), and ribulose biphosphate carboxylase (RBCS) promoter (Matsuoka et al., 1994 and U.S. Pat. No. 7,723,575). Other plant leaf-specific promoters that can be used with an expression construct of the invention include, but are not limited to, the Act1 promoter (U.S. Published Application No. 2009/0031441), AS-1 promoter (U.S. Pat. No. 5,256, 558), RBC-3A promoter (U.S. Pat. No. 5,023,179), the CaMV 35S promoter (Odell et al., 1985), the enhanced CaMV 35S promoter, the Figwort Mosaic Virus (FMV) promoter (Richins et al., 1987), the mannopine synthase (mas) promoter, the octopine synthase (ocs) promoter, or others such as the promoters from CaMV 19S (Lawton et al., 1987), nos (Ebert et al., 1987), Adh (Walker et al., 1987), sucrose synthase (Yang et al., 1990), α-tubulin, ubiquitin, actin (Wang et al., 1992), cab (Sullivan et al., 1989), PEPCase (Hudspeth et al., 1989), or those associated with the R gene complex (Chandler et al., 1989). See also published U.S. Application No. 2007/006346 and Yamamoto et al. (1997); Kwon et al. (1994); and Yamamoto et al. (1994). Other promoters that direct expression in the xylem of plants include the 4-coumarate Co-enzyme A ligase (4CL) promoter of *Populus* described in U.S. Pat. No. 6,831,208. Seed-specific promoters such as the promoter from a β-phaseolin gene (for example, of kidney bean) or a glycinin gene (for example, of soybean), and others, can also be used. Endosperm-specific promoters include, but are not limited to, MEG1 (EPO Application No. EP1528104) and those described by Wu et al. (1998), Furtado et al. (2001), and Hwang et al. (2002). Root-specific promoters, such as any of the promoter sequences described in U.S. Pat. No. 6,455,760 or U.S. Pat. No. 6,696,623, or in published U.S. Patent Application Nos. 2004/0078841; 2004/0067506; 2004/ 0019934; 2003/0177536; 2003/0084486; or 2004/0123349, can be used with an expression construct of the invention. Constitutive promoters (such as the CaMV, ubiquitin, actin, or NOS promoter), developmentally-regulated promoters, and inducible promoters (such as those promoters than can be induced by heat, light, hormones, or chemicals) are also contemplated for use with polynucleotide expression constructs of the invention.

Methods for identifying and characterizing promoter regions in plant genomic DNA are known in the art and include, for example, those described in the following references: Jordano et al. (1989); Bustos et al. (1989); Green et al. (1988); Meier et al. (1991); and Zhang et al. (1996). Published U.S. Application 2009/0199307 also describes methods for identifying tissue-specific promoters using differential display (see, e.g., U.S. Pat. No. 5,599,672). In differential display, mRNAs are compared from different tissue types. By identifying mRNA species which are present in only a particular tissue type, or set of tissue types, corresponding genes can be identified which are expressed in a tissue specific manner. RNA can be transcribed by reverse transcriptase to produce a cDNA, and the cDNA can be used to isolate clones containing the full-length genes. The cDNA can also be used to isolate homeologous or homologous promoters, enhancers or terminators from the respective gene using, for example, suppression PCR. See also U.S. Pat. No. 5,723,763.

Expression constructs of the invention may optionally contain a transcription termination sequence, a translation termination sequence, a sequence encoding a signal peptide, and/or enhancer elements. Transcription termination regions can typically be obtained from the 3' untranslated region of a eukaryotic or viral gene sequence. Transcription termination sequences can be positioned downstream of a coding sequence to provide for efficient termination. A signal peptide sequence is a short amino acid sequence typically present at the amino terminus of a protein that is responsible for the relocation of an operably linked mature polypeptide to a wide range of post-translational cellular destinations, ranging from a specific organelle compartment to sites of protein action and the extracellular environment. Targeting gene products to an intended cellular and/or extracellular destination through the use of an operably linked signal peptide sequence is contemplated for use with the polypeptides of the invention. Classical enhancers are cis-acting elements that increase gene transcription and can also be included in the expression construct. Classical enhancer elements are known in the art, and include, but are not limited to, the CaMV 35S enhancer element, cytomegalovirus (CMV) early promoter enhancer element, and the SV40 enhancer element. Intron-mediated enhancer elements that enhance gene expression are also known in the art. These elements must be present within the transcribed region and are orientation dependent. Examples include the maize shrunken-1 enhancer element (Clancy and Hannah, 2002).

DNA sequences which direct polyadenylation of mRNA transcribed from the expression construct can also be included in the expression construct, and include, but are not limited to, an octopine synthase or nopaline synthase signal. The expression constructs of the invention can also include a polynucleotide sequence that directs transposition of other genes, i.e., a transposon.

Polynucleotides of the present invention can be composed of either RNA or DNA. Preferably, the polynucleotides are composed of DNA. The subject invention also encompasses those polynucleotides that are complementary in sequence to the polynucleotides disclosed herein. Polynucleotides and polypeptides of the invention can be provided in purified or isolated form.

Because of the degeneracy of the genetic code, a variety of different polynucleotide sequences can encode polypeptides of the present invention. A table showing all possible triplet codons (and where U also stands for T) and the amino acid encoded by each codon is described in Lewin (1985). In addition, it is well within the skill of a person trained in the art to create alternative polynucleotide sequences encoding the same, or essentially the same, polypeptides of the subject invention. These variant or alternative polynucleotide sequences are within the scope of the subject invention. As used herein, references to "essentially the same" sequence refers to sequences which encode amino acid substitutions, deletions, additions, or insertions which do not materially alter the functional activity of the polypeptide encoded by the polynucleotides of the present invention. Allelic variants of the nucleotide sequences encoding an Hc1 protein of the invention are also encompassed within the scope of the invention.

Substitution of amino acids other than those specifically exemplified or naturally present in a polypeptide of the invention are also contemplated within the scope of the present invention. For example, non-natural amino acids can be substituted for the amino acids of an Hc1 polypeptide, so long as the polypeptide having the substituted amino acids retains substantially the same functional activity as the polypeptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form. Allelic variants of a protein sequence of a polypeptide of the present invention are also encompassed within the scope of the invention.

Amino acids can be generally categorized in the following classes: non-polar, uncharged polar, basic, and acidic. Conservative substitutions whereby a polypeptide of the present invention having an amino acid of one class is replaced with another amino acid of the same class fall within the scope of the subject invention so long as the polypeptide having the substitution still retains substantially the same functional activity as the polypeptide that does not have the substitution. Polynucleotides encoding a polypeptide having one or more amino acid substitutions in the sequence are contemplated within the scope of the present invention. Table 1 below provides a listing of examples of amino acids belonging to each class.

TABLE 1

Classes of amino acids

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

The subject invention also concerns variants of the polynucleotides of the present invention that encode functional polypeptides of the invention. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Fragments and variants of a polypeptide of the present invention can be generated as described herein and tested for the presence of function using standard techniques known in the art. Thus, an ordinarily skilled artisan can readily prepare and test fragments and variants of a polypeptide of the invention and determine whether the fragment or variant retains functional activity relative to full-length or a non-variant polypeptide.

Polynucleotides and polypeptides contemplated within the scope of the subject invention can also be defined in terms of more particular identity and/or similarity ranges with those sequences of the invention specifically exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, word length=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See the NCBI/NIH website.

The subject invention also contemplates those polynucleotide molecules having sequences which are sufficiently homologous with the polynucleotide sequences exemplified herein so as to permit hybridization with that sequence under standard stringent conditions and standard methods (Maniatis et al., 1982). As used herein, "stringent" conditions for hybridization refers to conditions wherein hybridization is typically carried out overnight at 20-25° C. below the melting temperature (Tm) of the DNA hybrid in 6×SSPE, 5×Denhardt's solution, 0.1% SDS, 0.1 mg/ml denatured DNA. The melting temperature, Tm, is described by the following formula (Beltz et al., 1983):

$$Tm=81.5° C.+16.6 \text{ Log } [Na^+]+0.41(\% G+C)-0.61(\% \text{ formamide})-600/\text{length of duplex in base pairs.}$$

Washes are typically carried out as follows:
(1) Twice at room temperature for 15 minutes in 1×SSPE, 0.1% SDS (low stringency wash).
(2) Once at Tm-20° C. for 15 minutes in 0.2×SSPE, 0.1% SDS (moderate stringency wash).

As used herein, the terms "nucleic acid" and "polynucleotide" refer to a deoxyribonucleotide, ribonucleotide, or a mixed deoxyribonucleotide and ribonucleotide polymer in either single- or double-stranded form, and unless otherwise limited, would encompass known analogs of natural nucleotides that can function in a similar manner as naturally-occurring nucleotides. The polynucleotide sequences include the DNA strand sequence that is transcribed into RNA and the strand sequence that is complementary to the DNA strand that is transcribed. The polynucleotide sequences also include both full-length sequences as well as shorter sequences derived from the full-length sequences. Allelic variations of the exemplified sequences also fall within the scope of the subject invention. The polynucleotide sequence includes both the sense and antisense strands either as individual strands or in the duplex.

Techniques for transforming plant cells with a gene are known in the art and include, for example, *Agrobacterium* infection, biolistic methods, electroporation, calcium chloride treatment, PEG-mediated transformation, etc. (see, for example, Nagel et al., 1990; Song et al., 2006; de la Pena et al., 1987; and Klein et al., 1993). U.S. Pat. No. 5,661,017 teaches methods and materials for transforming an algal cell with a heterologous polynucleotide. Transformed cells can be selected, redifferentiated, and grown into plants that contain and express a polynucleotide of the invention using standard methods known in the art. The seeds and other plant tissue and progeny of any transformed or transgenic plant cells or plants of the invention are also included within the scope of the present invention.

The subject invention also concerns methods for producing a plant that exhibits increased hc1 content and/or protein functional activity relative to a wildtype plant. In one embodiment, a polynucleotide encoding an Hc1 or a mutant Hc1 protein of the present invention is introduced into a plant cell and the polypeptide(s) encoded by the polynucleotide(s) is expressed. In one embodiment, the polynucleotide or polynucleotides is incorporated into the genome of the plant cell and a plant is grown from the plant cell. In a preferred embodiment, the plant grown from the plant cell stably expresses the incorporated polynucleotide or polynucleotides.

The subject invention also concerns methods and materials for selecting for plants having increased levels of plant growth, biomass, and/or resistance to drought conditions. In one embodiment, an hc1 gene or polynucleotide is utilized as a genetic marker. In a specific embodiment, the Hc1 protein comprises an amino acid sequence of SEQ ID NOs:2, 4, or 7-105, or a fragment or variant thereof having substantially the same activity as the full-length sequence. In a specific embodiment, the hc1 gene or polynucleotide comprises a nucleotide sequence of SEQ ID NO:1 or SEQ ID NO:3, or a fragment or variant thereof. Methods of the invention comprise determining whether a plant, plant tissue, or plant cell contains an hc1 gene or polynucleotide of the invention, and/or determining whether a plant, plant tissue, or plant cell comprises or expresses an Hc1 protein of the present invention. In one embodiment, the presence of an hc1 gene or polynucleotide is determined by screening nucleic acid from the plant, plant tissue, or plant cell for hybridization with a nucleic acid probe (e.g., an oligonucleotide of the invention) that hybridizes with an hc1 gene or polynucleotide of the invention. In another embodiment, the presence of an hc1 gene or polynucleotide is determined by restriction fragment length polymorphism (RFLP) analysis, by polymerase chain reaction (PCR) amplification of specific hc1 nucleic acid sequences, or by sequencing hc1-encoding nucleic acid from the plant, plant tissue, or plant cell and identifying whether the gene or polynucleotide comprises a sequence that provides for increased hc1 mRNA levels or increased hc1 activity.

The subject invention also concerns methods for marker assisted selection and breeding in plants using a gene or polynucleotide that provides for modulated expression (increased or decreased) of hc1 or the gene product thereof for selecting for plants, plant tissue, or plant cells that exhibit a phenotypic characteristic of interest, e.g., increased plant biomass and/or growth rates. Methods for marker assisted selection are known in the art.

The subject invention also concerns oligonucleotide probes and primers, such as polymerase chain reaction (PCR) primers, that can hybridize to a coding or non-coding sequence of a polynucleotide of the present invention. Oligonucleotide probes of the invention can be used in methods for detecting and quantitating nucleic acid sequences encoding a polypeptide of the invention. Oligonucleotide primers of the invention can be used in PCR methods and other methods involving nucleic acid amplification. In a preferred embodiment, a probe or primer of the invention can hybridize to a polynucleotide of the invention under stringent conditions. Probes and primers of the invention can optionally comprise a detectable label or reporter molecule, such as fluorescent molecules, enzymes, radioactive moiety (e.g., $^3$H, $^{35}$S, $^{125}$I, etc.), and the like. Probes and primers of the invention can be of any suitable length for the method or assay in which they are being employed. Typically, probes and primers of the invention will be 10 to 500 or more nucleotides in length. Probes and primers that are 10 to 20, 21 to 30, 31 to 40, 41 to 50, 51 to 60, 61 to 70, 71 to 80, 81 to 90, 91 to 100 or more nucleotides in length are contemplated within the scope of the invention. Probes and primers of the invention can have complete (100%) nucleotide sequence identity with the polynucleotide sequence, or the sequence identity can be less than 100%. For example, sequence identity between a probe or primer and a sequence can be 99%, 98%, 97%, 96%, 95%, 90%, 85%, 80%, 75%, 70% or any other percentage sequence identity so long as the probe or primer can hybridize under stringent conditions to a nucleotide sequence of a polynucleotide of the invention. In one embodiment, a probe or primer of the invention has 70% or greater, 75% or greater, 80% or greater, 85% or greater, 90% or greater, or 95% to 100% sequence identity with a nucleotide sequence of SEQ ID NO:1 or SEQ ID NO:3, or the complement thereof.

The subject invention also concerns isolated Hc1 polypeptides. In a specific embodiment, a polypeptide of the invention has an amino acid sequence as shown in SEQ ID NOs:2, 4, or 7-105, or functional fragment or variant thereof that exhibits substantially the same activity as a full-length amino acid sequence. A polypeptide of the invention can be purified using standard techniques known in the art. In one embodiment, a polynucleotide of the invention encoding an Hc1 polypeptide is incorporated into a microorganism, such as E. coli, and the polypeptide expressed in the microorganism and then isolated therefrom.

Polypeptides of the invention, and functional peptide fragments thereof, can be used to generate antibodies that bind specifically to a polypeptide of the invention, and such antibodies are contemplated within the scope of the invention. The antibodies of the invention can be polyclonal or monoclonal and can be produced and isolated using standard methods known in the art. In one embodiment, an antibody of the invention binds specifically to a polypeptide that comprises the amino acid sequence shown in SEQ ID NOs:2, 4, or 7-105, or a fragment or variant thereof. Antigen binding fragments (such as Fab or Fab$_2$ or Fv fragments) of antibodies of the invention can be routinely prepared and are also contemplated within the scope of the invention.

Fragments of a polypeptide of the invention, as described herein, can be obtained by cleaving the polypeptides of the invention with a proteolytic enzyme (such as trypsin, chymotrypsin, or collagenase) or with a chemical reagent, such as cyanogen bromide (CNBr). Alternatively, polypeptide fragments can be generated in a highly acidic environment, for example at pH 2.5. Polypeptide fragments can also be prepared by chemical synthesis or using host cells transformed with an expression vector comprising a polynucleotide encoding a fragment of a polypeptide of the invention, for example, a polypeptide that is a fragment of the amino acid sequence shown in SEQ ID NOs:2, 4, or 7-105. Fragments of a polypeptide of the invention also contemplated herein include fragments of the polypeptides wherein all or a part of a transit or signal sequence of the polypeptide is removed.

The subject invention also concerns cells transformed with a polynucleotide of the present invention encoding an Hc1 polypeptide of the invention, or that exhibit increased expression of an Hc1 encoding polynucleotide or the protein encoded by the polynucleotide, or that expresses a mutant hc1 polynucleotide or a mutant Hc1 protein that is characterized by increased expression or activity or function, or a fragment or variant thereof. In one embodiment, the cell is transformed with a polynucleotide sequence comprising a sequence encoding the amino acid sequence shown in SEQ ID NOs:2, 4, or 7-105, or a functional fragment or variant thereof. In a specific embodiment, the cell is transformed with a polynucleotide sequence shown in SEQ ID NO:1 and/or SEQ ID NO:3, or a sequence encoding a functional fragment or variant of SEQ ID NOs:2, 4, or 7-105. In one embodiment, the polynucleotide sequence is provided in an expression construct of the invention. The transformed cell can be a prokaryotic cell, for example, a bacterial cell such as E. coli or B. subtilis, or the transformed cell can be a eukaryotic cell, for example, a plant cell, including protoplasts, or an animal cell. Plant cells include, but are not limited to, dicotyledonous, monocotyledonous, and gymnosperm cells, such as conifer cells. In one embodiment, the plant cell is a cell from a Populus plant. The plant cell can be a cell from a hybrid plant, e.g., a poplar hybrid. Animal cells include human cells, mammalian cells, avian cells, and insect cells. Mammalian cells include, but are not limited to, COS, 3T3, and CHO cells.

The present invention further comprises any method for modulating the expression of an hc1 sequence provided herein or a homolog thereof in a plant. Such methods include introducing an hc1 gene or homolog into a plant, or enhancing the expression of an endogenous hc1 gene in a plant. In some embodiments, the present invention provides methods for transforming a plant of interest with an expression construct comprising a promoter that is capable of driving expression in the plant, operably linked to an hc1 sequence. In other embodiments, a promoter or enhancer element is inserted into the genome of a plant at a site that increases the expression of an endogenous hc1 coding sequence in the plant using the sequences provided herein.

Promoters for use in modulating the expression of an endogenous hc1 gene or homolog according to the present invention include any promoter known in the art. A promoter may be located near the transcription start site of a gene for which it regulates expression, such as an hc1 sequence provided herein. For example, a promoter may be located on the same strand of DNA and upstream of a coding sequence to be regulated. In some embodiments of the present invention, a promoter is inserted within about 5 kb of a coding sequence for which expression is to be regulated. A promoter may be inserted within about 1500 kb, within about 1000 kb, or within about 500 kb of an hc1 coding sequence for which expression will be regulated. A promoter may be inserted within about 200 bp of an hc1 coding sequence, or directly proximal to an hc1 coding sequence to be regulated.

Exemplary promoters which can be inserted into a plant genome to modulate expression of an hc1 gene according to the present invention include a cauliflower mosaic virus 35S (CaMV 35S) promoter (Odell et al., 1985), including an enhanced CaMV 35S promoter (U.S. Pat. No. 5,106,739) or a CaMV 19S promoter (Lawton et al., 1987), or a cassava vein mosaic virus promoter. Other promoters that can be used in plants of the present invention include, for example, a prolifera promoter, an Ap3 promoter, heat shock promoters, a T-DNA 1'- or 2'-promoter of *A. tumefaciens*, a polygalacturonase promoter, a chalcone synthase A (CHS-A) promoter, a tobacco PR-1α promoter, a ubiquitin promoter, an actin promoter, an alcA gene promoter, a pin2 promoter, a maize WipI promoter, a maize trpA gene promoter, a maize CDPK gene promoter, and a RUBISCO SSU promoter. Tissue-specific promoters, for example xylem-specific promoters, such as a promoter of the Cald5H, SAD, XCP1, CAD, CesA1, CesA2, CesA3 genes, a tubulin gene (TUB) promoter, a lipid transfer protein gene (LTP) promoter, or a coumarate-4-hydroxylase gene (C4H) promoter can be used. Leaf-specific promoters that can be used in the invention include a Cab1 promoter (Brusslan and Tobin, 1992), a Cab19 promoter (Bassett et al., 2007), a PPDK promoter (Matsuoka et al., 1993), and ribulose biphosphate carboxylase (RBCS) promoter (Matsuoka et al., 1994 and U.S. Pat. No. 7,723,575). Other plant leaf-specific promoters that can be used with an expression construct of the invention include, but are not limited to, an Act1 promoter (U.S. Published Application No. 2009/0031441), an AS-1 promoter (U.S. Pat. No. 5,256,558), a RBC-3A promoter (U.S. Pat. No. 5,023,179), a Figwort Mosaic Virus (FMV) promoter (Richins et al., 1987), a mannopine synthase (mas) promoter, an octopine synthase (ocs) promoter, or others such as the promoters from nos (Ebert et al., 1987), Adh (Walker et al., 1987), sucrose synthase (Yang et al., 1990), α-tubulin, ubiquitin, actin (Wang et al., 1992), cab (Sullivan et al., 1989), PEPCase (Hudspeth et al., 1989), or those associated with the R gene complex (Chandler et al., 1989). Other promoters that direct expression in the xylem of plants include the 4-coumarate Co-enzyme A ligase (4CL) promoter of *Populus* described in U.S. Pat. No. 6,831,208. Seed-specific promoters such as the promoter from a β-phaseolin gene (for example, of kidney bean) or a glycinin gene (for example, of soybean), and others, can also be used. Endosperm-specific promoters include, but are not limited to, MEG1 (EPO Application No. EP1528104) and those described by Wu et al. (1998), Furtado et al. (2001), and Hwang et al. (2002). Root-specific promoters, such as any of the promoter sequences described in U.S. Pat. No. 6,455,760 or U.S. Pat. No. 6,696,623, or in published U.S. Patent Application Nos. 2004/0078841; 2004/0067506; 2004/0019934; 2003/0177536; 2003/0084486; or 2004/0123349, can be used. Constitutive promoters (such as the CaMV, ubiquitin, actin, or NOS promoter), developmentally-regulated promoters, and inducible promoters (such as those promoters than can be induced by heat, light, hormones, or chemicals) are also contemplated for use in embodiments of the invention.

Enhancers include any molecule capable of enhancing gene expression when inserted into the genome of a plant. Thus, an enhancer can be inserted in a region of the genome upstream or downstream of the hc1 sequence using the sequences provided herein to enhance hc1 expression. Enhancers may be cis-acting, and can be located anywhere within the genome relative to a gene for which expression will be enhanced. For example, an enhancer may be positioned within about 1 Mbp, within about 100 kbp, within about 30 kbp, within about 20 kbp, or within about 10 kbp of a gene for which it enhances expression. An enhancer may also be located within about 1500 bp of a gene for which it enhances expression, or may be directly proximal to or located within an intron of a gene for which it enhances expression. Enhancers for use in modulating the expression of an endogenous hc1 gene or homolog according to the present invention include classical enhancer elements such as the CaMV 35S enhancer element, cytomegalovirus (CMV) early promoter enhancer element, and the SV40 enhancer element, and also intron-mediated enhancer elements that enhance gene expression such as the maize shrunken-1 enhancer element (Clancy and Hannah, 2002). Further examples of enhancers which may be introduced into a plant genome to modulate expression of an hc1 gene include a PetE enhancer (Chua, et al., 2003), or a rice α-amylase enhancer (Chen et al., 2002), or any enhancer known in the art (Chudalayandi, 2011). In some embodiments, the present invention comprises a subdomain, fragment, or duplicated enhancer element (Benfrey et al., 1990).

The invention further provides methods for modulating hc1 in a plant by inserting a promoter or enhancer into a plant genome such that it modulates expression of an endogenous or exogenous hc1 sequence. Methods for determining an insertion site for a promoter or enhancer using the sequences provided herein and methods for inserting a promoter or enhancer sequence into a plant genome at a given insertion site are known in the art (Podevin, et al., 2013; Wei et al., 2013). Such methods include the use of meganucleases (Bayer Research, vol. 24, pp. 68-71; WO 2013/026740), CRISPR/Cas9 sequences (Feng, et al., 2013), and TALENs (Zhang et al., 2012). Additional methods include Cre-lox site-specific recombination (Dale et al., 1995; Lyznik, et al., 2007); FLP-FRT recombination (Li, et al., 2009); Bxb1-mediated integration (Yau et al., 2011); zinc-finger mediated integration (Wright et al., 2005); Cai et al., 2009); and homologous recombination (Lieberman-Lazarovich and Levy, 2011); Puchta, 2002).

The subject invention also concerns plant tissue and plant parts, including, but not limited to, plant cells, plant protoplasts, plant cell tissue cultures from which plants can be regenerated, plant calli, plant clumps, and plant cells that are intact in plants or parts of plants such as branches, kernels, ears, cobs, husks, root tips, anthers, seeds, roots, embryos, hypocotyls, cotyledons, pollen, ovules, anthers, shoots, stalks, stems, leaves, fruits, and flowers, derived from a plant of the invention. The subject invention also concerns cuttings produced from a plant of the invention. In one embodiment, the cutting is a rootstock or a scion. In one embodiment, the cutting is a stem or branch from a young plant of the invention. In a specific embodiment, the stem is from a poplar plant comprising an hc1 gene, or the protein encoding portion thereof. In one embodiment, the poplar plant stem or branch is from a hybrid poplar plant.

The subject invention also encompasses plants and plant tissue that are bred from or otherwise derived from a plant of the present invention comprising a polynucleotide encoding an Hc1 polypeptide of the invention, or a fragment or variant thereof that provides for substantially the same activity. Seeds encompassed within the scope of the invention include hybrid seeds produced from a cross of a plant of the invention with another plant, such as an inbred plant.

In one embodiment, the plant of the invention and/or the other plant is a homozygous inbred line. In one embodiment, the other plant can be one that exhibits desirable agronomic traits and/or fruit quality. In a specific embodiment, the other plant is one that exhibits resistance to one or more plant pathogens, diseases, or herbicides. The subject invention also concerns hybrid plants grown from hybrid seed or cuttings of the invention. The subject invention also concerns plants on which plant tissue of the subject invention has been grafted. In one embodiment, the Hc1 protein encoded by the polynucleotide comprises the amino acid sequence shown in SEQ ID NOs:2, 4, or 7-105, or a fragment or variant thereof having substantially the same activity as a full-length sequence. In a further embodiment, the polynucleotide comprises the nucleotide sequence shown in SEQ ID NO:1 or SEQ ID NO:3. All patents, patent applications, provisional applications, and publications referred to or cited herein are incorporated by reference in their entirety, including all figures and tables, to the extent they are not inconsistent with the explicit teachings of this specification.

EXAMPLES

Following are examples that illustrate procedures for practicing the invention. These examples should not be construed as limiting. All percentages are by weight and all solvent mixture proportions are by volume unless otherwise noted.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

Example 1

Plant Material, Propagation, and Growth Measurements

The pedigree used to identify hc1 was a pseudo-backcross of the hybrid female parent 52-225 (*Populus trichocarpa* 93-968×*P. deltoides* ILL-101, *P. t×d*) and male parent D124 (*Populus deltoides*), hereafter referred to as Family 52-124. The parental plants and 100 individuals from the segregating population were clonally propagated as root cuttings, transplanted to deep pots, and placed randomly in a checkerboard arrangement on a flood bench. The plants were grown for 60 days, during which time the flood benches were flooded twice daily for approximately 30 minutes with a nutrient solution. Temperatures in the greenhouse ranged between 22° C. and 38° C., and interior photosynthetically active radiation ranged up to 1200 µmol s$^{-1}$ m$^{-2}$ (over the waveband 400-700 nm) during the daily 14 hours of natural irradiance.

Example 2

Plant Harvest, Biomass, and Growth Measurements

Sixty days after up-potting, plants were harvested. At the time of the harvest, plant final diameters and heights were recorded. Shoots were cut at the root collar and immediately re-cut under water, removing at least 5 cm from the cut end. Stem segments at least 10-cm long were stored in 15-mL conical tubes with deionized, distilled water in a cooler with ice for up to 5 hours until hydraulic conductivity could be measured. All leaves, sylleptic (lateral) branches, stems, and woody roots were dried in paper envelopes at 65° C., and weighed for calculation of total plant biomass. Height (H$_{INC}$ and diameter (D$_{INC}$) growth increments, were calculated as final (60 days growth) minus initial (30 days growth) measurements.

Example 3

Hydraulic Conductivity and Xylem Vessel Measurements

Hydraulic conductivity was determined two ways: first by the low pressure flow method on a subset of individuals, and then by the theoretical calculation of hydraulic conductivity on all individuals. Prior to the low pressure flow measurements, the stems were allowed to equilibrate to room temperature (25° C.), and re-cut under water with fresh razor blades. Stem segments contained multiple nodes, which were wrapped with parafilm to prevent leaks during measurement. To control for ion effects on pit membrane conductivity, the perfusion solution contained 20 mM KCl in distilled, deionized water, deaerated by sparging with helium (to reduce embolism formation), filtered to 0.2 µm, and adjusted to pH 2 with HCl (to control microbial growth). Stems were connected under water to a hydraulic apparatus containing the perfusion solution, and measurements were not taken until the zero-pressure (background) flow was zero. Flow of the solution through the stems at low pressure (4 kPa), to prevent flushing native embolism, was recorded on a balance connected to a computer and converted to initial conductivity (K$_{native}$, kg s$^{-1}$ m MPa$^{-1}$). Embolisms were then flushed with a higher pressure (>100 kPa) produced by a syringe mounted in a caulk gun, and the flow was recorded again and converted to maximum conductivity (K$_{max}$, kg m MPa$^{-1}$ s$^{-1}$). Percent loss of conductivity (PLC) was calculated as: PLC=100*(K$_{max}$−K$_{native}$)/K$_{max}$. After conductivity measurements were completed, all stems were placed in 15-mL conical tubes with 50% ethanol in deionized, distilled water, and stored at 4° C. until cross-sections were made. Cross-sections (approximately 50-µm thick) were made approximately 2 cm from the upstream end of the stem with a vibratome and mounted in deionized distilled water. Images of the xylem were captured by a digital camera attached to a light microscope at 3× magnification. In each cross-section, vessel area was measured by automated tracing and, when needed, manual drawing of the inner perimeter of the vessel lumen. The individual vessel areas were converted to diameters (d) and counted (n), and vessels per sapwood area (VSA, count per mm$^2$) and mean hydraulic diameter (D$_h$, ((Σd$^4$)n$^{-1}$)$^{1/4}$) were calculated. To determine theoretical conductivity, d was used to calculate lumen resistivity for each vessel as follows:

$$R_L = \frac{128 * \eta}{\pi * d^4}, \qquad (3)$$

where η is the viscosity of water at 25° C. to agree with low pressure flow meter measurements (8.9×10$^{-10}$ MPa s). Lumen conductivity for each vessel was calculated as the inverse of R$_L$ (Ohm's Law), and then summed (conductances in parallel are additive) to determine theoretical conductivity, K$_t$, in m$^4$ MPa$^{-1}$ s$^{-1}$. The K$_t$ values were converted to the same units as $K_{max}$ (kg m $MPa^{-1}$ $s^{-1}$) by multiplying by 1000 kg $m^{-3}$ $H_2O$. Sapwood specific conductivity ($K_S=K_t/SA$, kg $m^{-1}$ $MPa^{-1}$ $s^{-1}$) and leaf specific conductivity ($K_L=K_t/LA$, kg $m^{-1}$ $MPa^{-1}$ $s^{-1}$, where LA is total leaf area distal to the stem segment) were also calculated.

Example 4

Measured and Theoretical Conductivity

Using 29 young poplar stems, $K_t$ was established as a good predictor of $K_{max}$ ($K_{max}=1.46*K_t$, non-significant intercept, $r^2=0.9266$, $P<0.0001$). Overall, the strength of the relationship between $K_{max}$ and $K_t$, and the fact that the overestimate was consistent across the range of conductivity, support the conclusion that $K_t$ is an excellent predictor of the more difficult-to-measure $K_{max}$. In addition, with the low pressure flow method, PLC averaged <3%, and the maximum observed PLC was about 9%, suggesting that watering twice a day was sufficient to minimize embolism and that $K_t$ would be similar to $K_h$ in the experiments described herein. Thus, all hydraulic conductivity and specific conductivity results presented are based on $K_t$ measurements.

Example 5

Statistical Analysis

Regression analysis was used to relate hydraulic traits to growth. Means of all ramets per genotype were used in the plots and regression analyses, which were performed with SigmaPlot version 10.0 (Systat Software, Inc., San Jose, Calif., USA).

Figure 2:
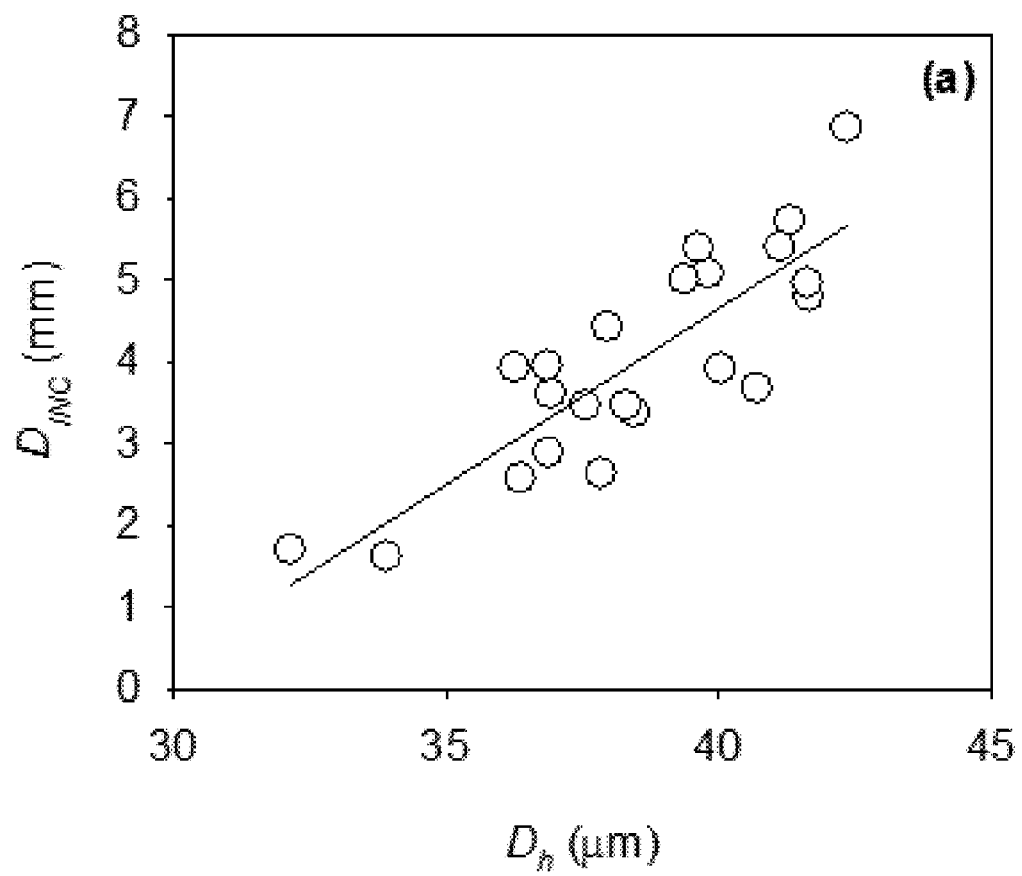
FIG. 2—Shows a linear regression plot demonstrating the positive association ($r^2$=0.7196, P<0.0001) between hydraulic vessel diameter ($D_h$) and diameter increment ($D_{INC}$). Points are progeny genotype means.

Genetic and phenotypic correlations were determined among growth and hydraulic conductivity traits. Phenotypically, hydraulic conductivity was positively correlated with diameter and height increment. A significant positive genetic correlation was also detected between diameter and height increment, and vessel diameter and conductivity (Table 2), which indicated a pleiotropic contribution of hydraulic conductivity to plant growth. The strongest phenotypic correlation occurred between $D_{INC}$ and $K_L$ (FIG. 1). Both $D_h$ and VSA also had strong phenotypic and genetic correlations with $D_{INC}$, with large vessels correlated with greater diameter increment (FIG. 2). $K_L$ also had a very strong positive genetic correlation with $D_h$ (0.82±0.11). The strong genetic correlation between hydraulic conductivity and productivity, particularly $K_L$ and diameter increment, indicates that genes that regulate hydraulic conductivity are candidates for the regulation of growth in Populus. The positive direction of this correlation also supports the hypothesis that high hydraulic conductivity is a prerequisite for fast growth in angiosperms.

TABLE 2

Within-family broad sense heritabilities (diagonal, bold type), genetic correlations (above diagonal), and phenotypic correlations (below diagonal) for progeny genotypes (standard errors in parentheses).

| Trait | $D_{INC}$ | $H_{INC}$ | $D_h$ | $K_S$ | $K_L$ | BIO |
|---|---|---|---|---|---|---|
| Diameter increment ($D_{INC}$) | 0.45 (0.13) | 0.88 (0.08) | 0.89 (0.09) | 0.45 (0.28) | 0.71 (0.18) | 0.92 (0.06) |
| Height increment ($H_{INC}$) | 0.89 (0.03) | 0.31 (0.13) | 0.68 (0.19) | 0.24 (0.35) | 0.27 (0.33) | 0.79 (0.14) |
| Vessel diameter | 0.81 | 0.77 | 0.29 | 0.73 | 0.82 | 0.64 |
| ($D_h$) | (0.05) | (0.06) | (0.13) | (0.17) | (0.11) | (0.22) |
| Sapwood hydraulic conductivity ($K_S$) | 0.51 (0.10) | 0.48 (0.10) | 0.87 (0.04) | 0.29 (0.13) | — | 0.19 (0.34) |
| Leaf hydraulic conductivity ($K_L$) | 0.66 (0.08) | 0.56 (0.10) | 0.88 (0.03) | — | 0.34 (0.13) | 0.34 (0.30) |
| Total plant biomass (BIO) | 0.86 (0.03) | 0.79 (0.05) | 0.66 (0.08) | 0.40 (0.12) | 0.48 (0.11) | 0.41 (0.14) |

Correlations that are not biologically applicable (—).

Example 6

Transcriptome Analysis of Family 52-124

A set of 396 individuals from Family 52-124 were propagated and grown as described above. From a common set of 192 randomly selected individuals, 180 samples of differentiating xylem and 183 expanding leaves were collected for gene expression analysis. Collected tissues were immediately flash-frozen in liquid nitrogen and stored at −80° C. until lyophilization and RNA extraction. RNA was extracted from each lyophilized sample by a standard protocol, converted to double-stranded cDNA, labeled with cy3, and hybridized to microarrays. Hybridizations were carried out using a previously described four-plex NimbleGen (Madison, Wis.) microarray platform (Gene Expression Omnibus Accession# GPL7234) using probes designed to minimize the effects of sequence polymorphism on the estimates of gene expression. The microarray comprised one probe per gene for 55,793 previously described gene models derived from the annotation of the genome sequence of P. trichocarpa clone 'Nisqually-1' (version 1.1), and a set of non-annotated ESTs. Raw data from hybridizations were background subtracted, $log_2$-transformed, and quantile-normalized separately on a tissue-by-tissue basis. Raw and normalized gene expression data is publically available (Gene Expression Omnibus Accession # GSE12623, GSE20117, and GSE20118).

Example 7

Quantitative Trait Analysis

Quantitative trait loci (QTL) for growth, hydraulic, and physiological traits were identified using composite interval mapping performed with QTL Cartographer V2.5 on a previously established, high quality single-tree map of the hybrid mother of family 52-124 using each quantile-normalized gene expression value. The standard model (model 6) was used, with a walk speed of 2 cM, and significance level of $P<0.05$, determined by performing 1000 permutation tests. The magnitude of the QTL effect was calculated as the percentage variance explained (PVE). The likelihood ratio (LR) was converted to an equivalent log of odds (LOD) score by multiplying LR by 0.2171.

Significance of eQTL Log of Odds (LOD) values was estimated for xylem, leaf, and root using a global permutation threshold. eQTL were declared on the basis of a strategy wherein eQTL composed of unimodal LOD curves are located by the peak position. Bimodal peaks were declared as separate eQTL if the trough between them exceeded 2 LOD. The eQTL were classified as cis- or trans-regulated based on co-localization of the eQTL LOD peak with the genetic map marker bin containing the gene model in the 'Nisqually-1' genome sequence.

Vessel diameter QTL were detected between genetic markers at positions 28.5-36.9 megabase pair (Mbp) of chromosome 1, where a QTL for total plant biomass growth was previously mapped (Novaes et al., *New Phytol* 182:878-90, 2009) in the same population. Of 827 genes within the interval, 53 were previously recorded as expressed primarily in tissues derived from the vascular cambium (Quesada et al., *New Phytol* 180:408-20, 2008), where meristematic cell differentiation into vessels takes place. Transcriptional variation of these genes, measured in differentiating xylem of the pseudo-backcross population (Drost et al., *PNAS USA* 107:8492-7, 2010), was analyzed as a quantitative phenotype and cis-regulated expression QTL were identified for four genes. Assuming that regulation of vessel properties and hydraulic conductivity occurs at the transcriptional level, further analysis was conducted on these four genes that are positioned within the trait QTL interval and that are cis-regulated. Among the possible candidates, hc1 was selected as the most likely regulator of vessel formation, hydraulic conductivity, and growth.

Figure 3:
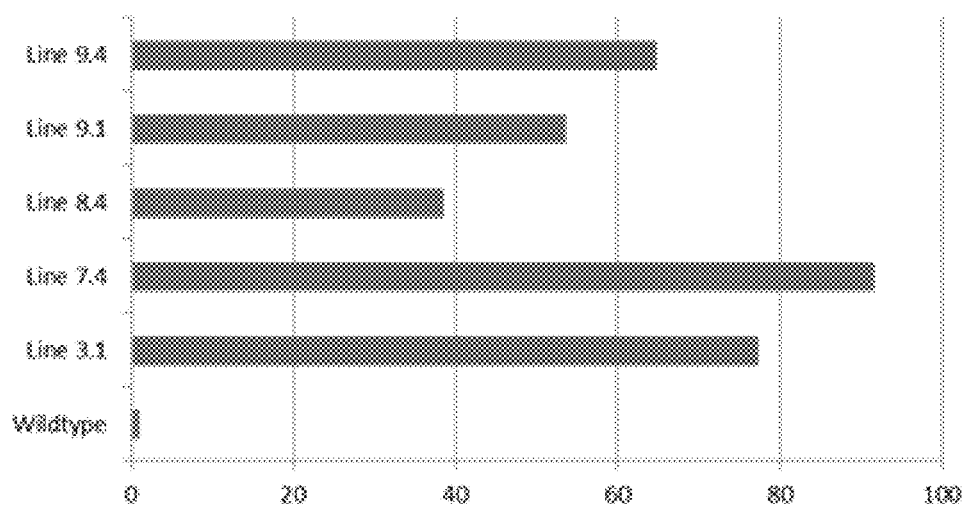
FIG. 3—Shows a graph depicting up to a 90-fold increase in expression of hc1 in comparison to wildtype (level of expression=1) using Delta Delta CT analysis. Actin was used as the control gene.

Multiple significant (P<0.05) QTL were identified for growth and hydraulic traits (FIG. 3). Of particular interest for this study were co-localized QTL detected in linkage group one, for $D_{INC}$, $H_{INC}$, $D_h$, $K_t$, $K_S$ and $K_L$. The data suggests that the observed genetic and phenotypic correlation among these traits is driven by single or few common genetic elements. Therefore, a genetic/genomics approach was used to identify these elements, where information from expression QTL analysis was used to define a putative regulator of the growth, hydraulic, and physiological traits.

Example 8

Genetic/Genomic Analysis of Growth, Hydraulic, and Physiological Traits

In order to identify candidate genes affecting hydraulic conductivity and growth in *Populus*, growth and hydraulic conductivity traits were quantified, differentiating xylem and leaves were sampled, and gene expression profiles of segregating progeny of *P. deltoides* and *P. trichocarpa* were obtained. Candidate genes for regulating a trait transcriptionally were expected to be regulated in cis, and to contain an expression QTL that co-localizes with the trait QTLs. In this analysis, a gene of unknown function was identified, annotated in the *P. trichocarpa* genome as POPTR_0001 s33660 (or estExt_Genewise1_v1.C_LG_I3118 in the first annotation of the genome). The gene was located within the interval of the QTL for $D_{INC}$, $H_{INC}$, $D_h$, $K_t$, $K_S$ and $K_L$, and genetic regulation of its expression in leaves and xylem was regulated by the same locus.

Example 9

Modification of the Expression of hc1

To verify the role of hc1 (previously referred to as POPTR_0001 s33660) in the regulation of growth and hydraulic conductivity traits, its expression was altered by developing transgenic lines using RNAi-mediated gene silencing and ectopic expression using 35S promoter to generate loss- and gain-of-function variants, respectively. The coding sequence of hc1, obtained from *P. trichocarpa* reference genotype Nisqually-1, was cloned into pCAPT Transitive for the RNAi and pCAPO for overexpression. *Agrobacterium*-mediated transformation using strain GUV3101 was performed in the *Populus tremula×P. alba* (717-1B4 genotype) background. RNAi (i.e., loss of function) was lethal and did not generate any transgenics. Overexpression independent transgenic lines were screened for hc1 expression using RT-PCR, and the three lines that showed different levels of up-regulation were clonally replicated and planted in a greenhouse, and in growth chambers at the University of Florida.

Example 10

Hydraulic Conductivity and Xylem Vessel Measurements of Transgenic Lines

Figure 5:
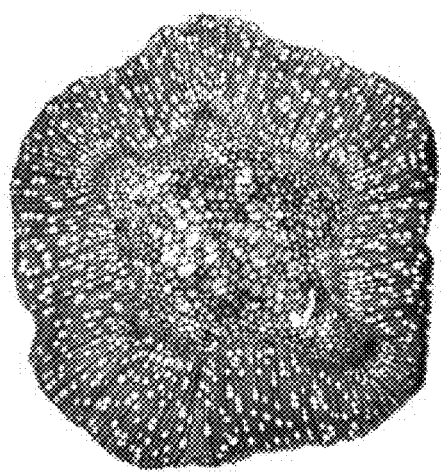
FIG. 5—Shows light microscopy images of xylem cross-sections demonstrating higher vessel number and diameter in a transgenic line overexpressing hc1 (panel A) compared to wildtype (panel B).
Figure 5:
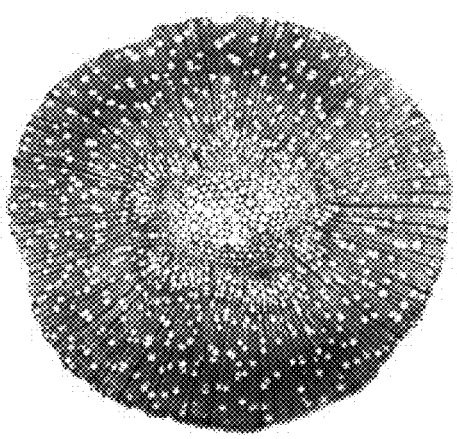
Figure 6:
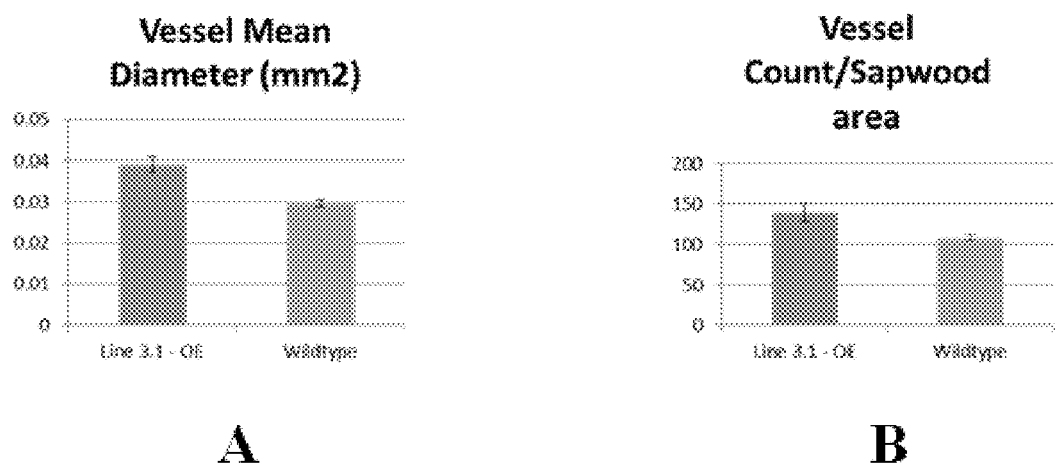
FIG. 6—Shows bar graphs demonstrating vessel mean diameter (panel A) and number (panel B) in a transgenic line overexpressing POPTR_0001 s33660, compared to wildtype.

Stem vessel properties were characterized in the transgenic line with the highest growth rate observed in greenhouse (FIG. 4), using the conditions and methods described previously. Measurements showed that the transgenic line contains a significantly larger number of vessels per sapwood area, as well as larger vessel element diameter and height (FIGS. 5 and 6 and Table 3). Consequently, the area occupied by vessels per sapwood area is also significantly higher.

TABLE 3

Vessel element area, mean diameter, and number of vessels measured in the transgenic line 3.1 overexpressing hc1, and in the wildtype. All measurements have been normalized to total sapwood area, and are based on the analysis of three biological replicates of transgenic and wildtype. Standard deviations are presented in parenthesis.

| Trait | Transgenic 3.1 | Wildtype |
| --- | --- | --- |
| Vessel element area per sapwood area | 0.1925 (0.0111) | 0.0878 (0.0057) |
| Vessel number per sapwood area | 139.1264 (11.62) | 108.32 (3.70) |
| Vessel element mean diameter (mm$^2$) | 0.0390 (0.0019) | 0.0297 (0.0008) |
| Vessel element height (mm$^2$) | 0.4549 (0.1386) | 0.3439 (0.0924) |

Figure 4:
FIG. 4—Shows growth comparisons demonstrating visibly higher growth of transgenic lines overexpressing hc1 compared to wildtype.

It was also observed that line 3.1, as well as other transgenic lines, grew significantly more in greenhouse, compared to wildtype (FIG. 4). Therefore, growth traits were subsequently measured under highly controlled growth chamber conditions. Over-expression of hc1 may not only lead to higher growth through higher hydraulic conductivity, but it has also been shown that poplar trees with higher vessel diameter have also higher drought tolerance, because they can support better control of the stomatal aperture under water-limiting conditions.

Hydraulic conductivity was also measured in the transgenic lines and wildtype, to evaluate if the change in vessel properties would imply higher conductivity. As expected, hydraulic conductivity was significantly higher in all three transgenic lines relative to wildtype (average 28% increase), reflecting that flow is proportional to the fourth power of vessel diameter (Tyree et al., Xylem Structure and the Ascent of Sap. New York: Springer-Verlag, 2002).

Example 11

Growth of Transgenic Lines Under Standard and Heat Stress Conditions

Five to six biological replicates of each of three transgenic lines with the highest level of hc1 expression, and six biological replicates of the wildtype, were grown for up to 16 weeks in growth chamber with a continuous water supply. The temperature of the growth chamber was maintained at 25° C., and the interior photosynthetically active radiation ranged up to 600 μmol s$^{-1}$ m$^{-2}$ (over the waveband 400-700 nm) during the daily 12 hours of irradiance. Plant heights were measured weekly. For the first eight weeks, height growth rates remained consistent among transgenic and wildtype lines. As the plants reached >90 cm, growth rates increased 10-18% in the three transgenic lines compared to wildtype. The acceleration of growth is presumed to occur because, as the plants became larger and had higher leaf area, transpiration demand increased sufficiently to the point that hydraulic conductivity became restrictive in the wildtype.

Under heat stress, plants may reduce or cease growth when the transpiration demand surpasses what can be supported by the plant's hydraulic conductivity. In order to address if transgenic plants with higher hydraulic conductivity would be more tolerant to heat stress and thus support growth longer, transgenic and wildtype plants were grown under the same conditions described above, except that temperature was maintained at 33° C. after an acclimation period. Height growth was measured weekly in six biological replicates of three transgenic lines and wildtype until the weekly growth increment ceased or was less than 1 cm. For the first 11 weeks, height growth rates exceeded 1 cm per day in both transgenic and wildtype lines. Between the 11$^{th}$ and 12$^{th}$ week, height growth increment decreased dramatically in the wildtype (0.6 cm/week), and ceased in the following week. Among the three transgenic lines, height growth rates remained above 1 cm/week for an additional two weeks, before ceasing growth in the 15$^{th}$ week of the growth chamber experiment. Thus, the higher hydraulic conductivity provided the capability for the transgenic plants to maintain active growth for 2-3 additional weeks compared to wildtype plants.

Example 12

Identification of HC1 Homologs

Homologs of the HC1 protein (also referred to as EVE) were identified by querying the poplar amino acid sequence of Potri.001G329000.1 against translated genomic DNA sequences, using TBLASTN (National Center for Biotechnology Information). A putative homolog was declared when the expected value of the sequence alignment (E-value) was <1e-10, and when the alignment covered 90% or more of the HC1 protein sequence. Furthermore, homologues were only declared if the predicted protein sequence contained DUF3339 conserved amino acids tryptophan at position 4, proline at positions 19 and 26, and glycine at position 20. A wide variety of copy number of HC1 was detected in sequenced land plant genomes, from 2-3 copies in mosses (*Physcomitrella patens*) to over 30 copies in grasses (*Oryza sativa*).

To determine whether HC1 was vertically inherited throughout a broader range of land plants that expands beyond those for which a genome sequence is available, a multiple sequence alignment was generated using transcriptome data from the One Thousand Plant Transcriptome Project (1KP, onekp.com). Representative taxa from every major land plant lineage were selected from the 1KP database. Over 30 green algae transcriptomes were also searched, including from the Zygnematales, the order of streptophyte green algae likely to be the sister group to land plants. Transcripts matching any copy of the domain DUF3339 from *Physcomitrella patens* or *Oryza sativa* were detected using EXONERATE v 2.22.4 (Slater and Birney, 2005). 139 copies of HC1 were identified in 46 transcriptomes, including several species of streptophyte green algae. No copies of HC1 were found in the six published genomes (and ten additional transcriptomes) of chlorophyte green algae, which are more distantly related to land plants. In land plants, copies of HC1 could be found in most phyla, including Bryophyta (mosses), Marchantiophyta (liverworts), Lyopodiophyta (club mosses), and seed plants. Among the monilophytes (ferns and horsetails), HC1 can be found in some ancestral lineages (*Ophioglossum* and *Sceptridium*) but appears to have been lost in the more derived leptosporangiate ferns.

Example 13

Sequence Comparison of HC1 Homologs

Figure 7:
FIG. 7—Shows an alignment of HC1 sequences according to the present invention. Table 4 identifies the Accession numbers listed in the Figure by their corresponding SEQ ID NOs, wherein the Accession numbers correspond to SEQ ID NOs: 4 and 7-105.
Figure 7:
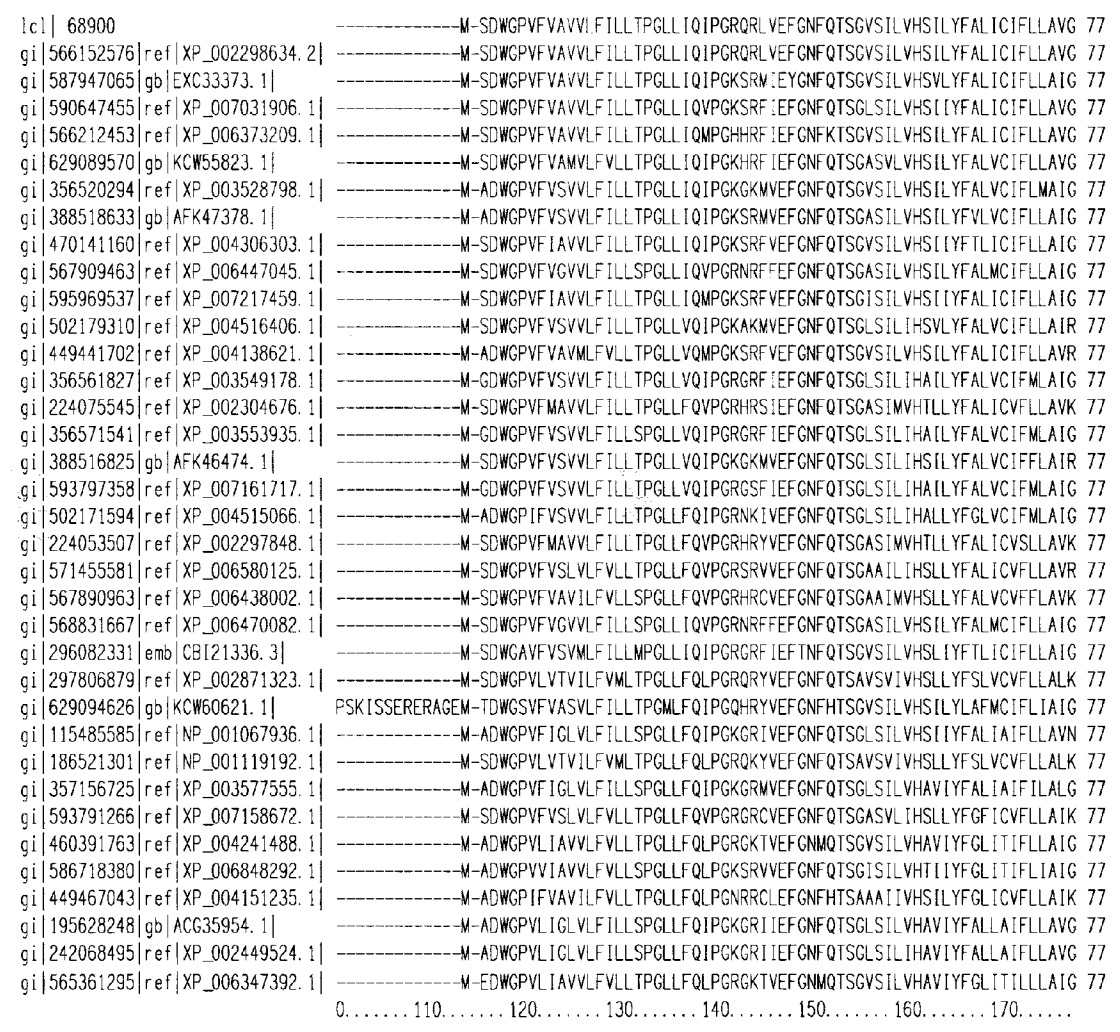
Figure 7:
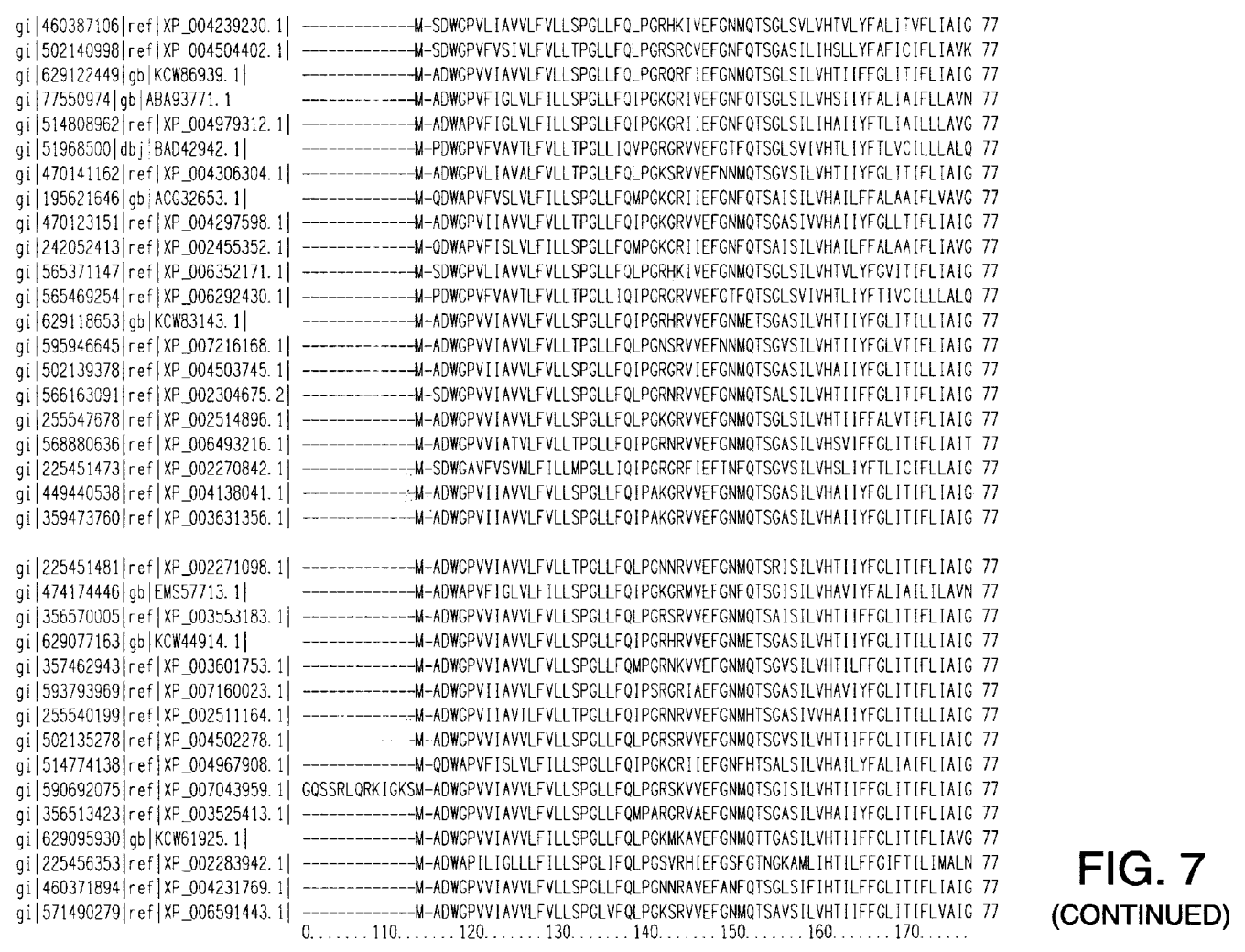

A sequence alignment of HC1 homologs was prepared using the HC1 poplar sequence as the reference sequence (FIG. 7). The alignment was prepared by querying the poplar HC1 sequence (SEQ ID NO:4; listed in the figure as lcl|168900) in BLAST (National Center for Biotechnology Information). The resulting BLAST hits were aligned using the COBALT tool (National Center for Biotechnology Information). The FASTA alignments were downloaded from the COBALT output, then aligned using Clustal X2 software. Table 4 shows HC1 homologs identified based on the HC1 poplar sequence provided herein.

Several conserved motifs were identified among the aligned sequences. LTPGL (SEQ ID NO:5) and GNFQTSGVSILV (SEQ ID NO:6) are well-conserved among the aligned sequences.

TABLE 4

HC1 homologs identified based on the HC1 poplar sequence.

| Accession No. | SEQ ID NO. | Sequence | Genus/Species |
|---|---|---|---|
| Poplar HC1 reference sequence | 4 | MSDWGPVFVAVVLFILLTPGLLIQIPGRQRLVEFGNF QTSGVSILVHSILYFALICIFLLAVGVHVYVGS | |
| XP_002298634.2 | 7 | MSDWGPVFVAVVLFILLTPGLLIQIPGRQRLVEFGNF QTSGVSILVHSILYFALICIFLLAVGVHVCSLCTPSMLD | *Populus trichocarpa* |
| EXC33373.1 | 8 | MSDWGPVFVAVVLFILLTPGLLIQVIPGKSRMIEYGNF QTSGVSILVHSVLYFALICIFLLAIGVHMYLGS | *Morus notabilis* |

TABLE 4-continued

HC1 homologs identified based on the HC1 poplar sequence.

| Accession No. | SEQ ID NO. | Sequence | Genus/Species |
|---|---|---|---|
| XP_007031906.1 | 9 | MSDWGPVFAVVLFILLTPGLLIQVPGKSRFIEFGNF QTSGLSILVHSIIYFALICIFLLAVGVHMYVGS | Theobroma cacao |
| XP_006373209.1 | 10 | MSDWGPVFAVVLFILLTPGLLIQMPGHHRFIEFGN FKTSGVSILVHSILYFALICIFLLAVGVHMYVGS | Populus trichocarpa |
| KCW55823.1 | 11 | MSDWGPVFAMVLFVLLTPGLLIQIPGKHRFIEFGN FQTSGASVLVHSILYFALVCIFLLAVGVHVYIGS | Eucalyptus grandis |
| XP_003528798.1 | 12 | MADWGPVFVSVVLFILLTPGLLIQIPGKGKMVEFGN FQTSGVSILVHSILYFALVCIFLMAIGVHMYTGS | Glycine max |
| AFK47378.1 | 13 | MADWGPVFVSVVLFILLTPGLLIQIPGKSRMVEFGN FQTSGASILVHSILYFVLVCIFLLAIGVHMYMG | Lotus japonicus |
| XP_004306303.1 | 14 | MSDWGPVFIAVVLFILLTPGLLIQIPGKSRFVEFGNF QTSGVSILVHSIIYFTLICIFLLAIGVHMYIVHGLGILIL TSYSDVKFEALDLKEMADWGPVLIGVVLFILLQPGL LFSLPGNGKQVEFGSMKTNGKAIAVHTLIEFALYAIL ILAVHVHIYTG | Fragaria vesca subsp. vesca |
| XP_006447045.1 | 15 | MSDWGPVFGVVLFILLSPGLLIQVPGRNRFFLFGN FQTSGASILVHSILYFALMCIFLLAIGVHMYLG | Citrus clementina |
| XP_007217459.1 | 16 | MSDWGPVFIAVVLFILLTPGLLIQMPGKSRFVEFGNF QTSGISILVHSIIYFALICIFLLAIGVHMYEIIMADWGP ILIGVVLFILLQPGLLFSLPGNSRQVEFGSMKTNGKAI AVHTLIEFALYAILILAVHVHIYTG | Prunus persica |
| XP_004516406.1 | 17 | MSDWGPVFVSVVLFILLTPGLLVQIPGKAKMVEFGN FQTSGLSILIHSVLYFALVCIFLLAIRIHMYLG | Cicer arietinum |
| XP_004138621.1 | 18 | MADWGPVFAVMLFVLLTPGLLVQMPGKSRFVEF GNFQTSGVSILVHSILYFALICIFLLAVRVHVYNGISE TMSDWAPVVIGVVLFVLLSPGLLFQFPGNNRQEEFG SMKTNGKAVAIHTLIEEVLYAVFILALHIHIYTG | Cucumis sativus |
| XP_003549178.1 | 19 | MGDWGPVFVSVVLFILLTPGLLVQIPGRGRFIEFGNF QTSGLSILIHAILYFALVCIFMLAIGIHMYMG | Glycine max |
| XP_002304676.1 | 20 | MSDWGPVFMAVVLFILLTPGLLFQVPGRHRSIEFGN FQTSGASIMVHTLLYFALICVFLLAVKVHLYLG | Populus trichocarpa |
| XP_003553935.1 | 21 | MGDWGPVFVSVVLFILLSPGLLVQIPGRGRFIEFGNF QTSGLSILIHAILYFALVCIFMLAIGIHMYMG | Glycine max |
| AFK46474.1 | 22 | MSDWGPVFVSVVLFILLTPGLLVQIPGKGKMVEFGN FQTSGLSILIHSILYFALVCIFFLAIRIHMYMG | Medicago truncatula |
| XP_007161717.1 | 23 | MGDWGPVFVSVVLFILLTPGLLVQIPGRGSFIEFGNF QTSGLSILIHAILYFALVCIFMLAIGIHMYMG | Phaseolus vulgaris |
| XP_004515066.1 | 24 | MADWGPIFVSVVLFILLTPGLLFQIPGRNKIVEFGNF QTSGLSILIHALLYFGLVCIFMLAIGIHMYAG | Cicer arietinum |
| XP_002297848.1 | 25 | MSDWGPVFMAVVLFILLTPGLLFQVPGRHRYVEFG NFQTSGASIMVHTLLYFALICVSLLAVKVHLYLG | Populus trichocarpa |
| XP_006580125.1 | 26 | MSDWGPVFVSLVLFVLLTPGLLFQVPGRSRVVEFG NFQTSGAAILIHSLLYFALICVFLLAVRIHFYLG | Glycine max |
| XP_006438002.1 | 27 | MSDWGPVFAVILFVLLSPGLLFQVPGRHRCVEFGN FQTSGAAIMVHSLLYFALVCVFFLAVKVHLYLG | Citrus clementina |
| XP_006470082.1 | 28 | MSDWGPVFGVVLFILLSPGLLIQVPGRNRFFLFGN FQTSGASILVHSILYFALMCIFLLAIGVHICNTSTMAD WGPVVIGVVLFVLLQPGLLFQLPGHSRLLEFGSMKT NGKAISVHTLIFFVLYAILILAVHVHIYSG | Citrus sinensis |
| CBI21336.3 | 29 | MSDWGAVFVSVMLFILLMPGLLIQIPGRGRFIEFTNF QTSGVSILVHSLIYFTLICIFLLAIGVHMYIG | Vitis vinifera |
| XP_002871323.1 | 30 | MSDWGPVLVTVILFVMLTPGLLFQLPGRQRYVEFG NFQTSAVSIVIHSLLYFSLVCVFLLALKIHIYIG | Arabidopsis lyrata subsp. lyrata |

TABLE 4-continued

HC1 homologs identified based on the HC1 poplar sequence.

| Accession No. | SEQ ID NO. | Sequence | Genus/Species |
|---|---|---|---|
| KCW60621.1 | 31 | TSSITFEVIIFTIILPQNYPSKISSERERAGEMTDWGSV FVASVLFILLTPGMLFQIPGQHRYVEFGNFHTSGVSI LVHSILYLAFMCIFLIAIGVHMYIGS | *Eucalyptus grandis* |
| NP_001067936.1 | 32 | MADWGPVFIGLVLFILLSPGLLFQIPGKGRIVEFGNF QTSGLSILVHSIIYFALIAIFLLAVNVHMYLG | *Oryza sativa* Japonica Group |
| NP_001119192.1 | 33 | MSDWGPVLVTVILFVMLTPGLLFQLPGRQKYVEFG NFQTSAVSVIVHSLLYFSLVCVFLLALKIHIYIG | *Arabidopsis thaliana* |
| XP_003577555.1 | 34 | MADWGPVFIGLVLFILLSPGLLFQIPGKGRMVEFGN FQTSGLSILVHAVIYFALIAIFILALGVHVYLG | *Brachypodium distachyon* |
| XP_007158672.1 | 35 | MSDWGPVFVSLVLFVLLTPGLLFQVPGRGRCVEFG NFQTSGASVLIHSLLYFGFICVFLLAIKIHLYLG | *Phaseolus vulgaris* |
| XP_004241488.1 | 36 | MADWGPVLIAVVLFVLLTPGLLFQLPGRGKTVEFG NMQTSGVSILVHAVIYFGLITIFLLAIGVHVYVG | *Solanum lycopersicum* |
| XP_006848292.1 | 37 | MADWGPVVIAVVLFVLLSPGLLFQLPGKSRVVEFG NFQTSGISILVHTIIYFGLITIFLIAIGVHIYTG | *Amborella trichopoda* |
| XP_004151235.1 | 38 | MADWGPIFVAVILFVLLTPGLLFQLPGNRRCLEFGN FHTSAAAIIVHSILYFGLICVFLLAIKVHLYIGS | *Cucumis sativus* |
| ACG35954.1 | 39 | MADWGPVLIGLVLFILLSPGLLFQIPGKGRIIEFGNFQ TSGLSILVHAVIYFALLAIFLLAVGVHIYLG | *Zea mays* |
| XP_002449524.1 | 40 | MADWGPVLIGLVLFILLSPGLLFQIPGKGRIIEFGNFQ TSGLSILIHAVIYFALLAIFLLAVGVHIYLG | *Sorghum bicolor* |
| XP_006347392.1 | 41 | MEDWGPVLIAVVLFVLLTPGLLFQLPGRGKTVEFG NMQTSGVSILVHAVIYFGLITILLLAIGVHVYVG | *Solanum tuberosum* |
| XP_004239230.1 | 42 | MSDWGPVLIAVVLFVLLSPGLLFQLPGRHKIVEFGN MQTSGLSVLVHTVLYFALITVFLIAIGVHIHTG | *Solanum lycopersicum* |
| XP_004504402.1 | 43 | MSDWGPVFSIVLFVLLTPGLLFQLPGRSRCVEFGN FQTSGASILIHSLLYFAFICIFLIAVKIHLCNLQKLVM AADWGPVVISVVLFVLLSPGLLFQLPAKGRVVAFGS MQTSGISILVHTIIFFGLITIFLLAIGIHIYSG | *Cicer arietinum* |
| KCW86939.1 | 44 | MADWGPVVIAVVLFVLLSPGLLFQLPGRQRFIEFGN MQTSGLSILVHTIIFFGLITIFLIAIGVHIYTG | *Eucalyptus grandis* |
| ABA93771.1 | 45 | MADWGPVFIGLVLFILLSPGLLFQIPGKGRIVEFGNF QTSGLSILVHSIIYFALIAIFLLAVNVHMFLEFGYLPWI | *Oryza sativa* Japonica Group |
| XP_004979312.1 | 46 | MADWAPVFIGLVLFILLSPGLLFQIPGKGRIIEFGNFQ TSGLSILIHAIIYFTLIAILLLAVGVHVYLG | *Setaria italica* |
| BAD42942.1 | 47 | MPDWGPVFAVTLFVLLTPGLLIQVPGRGRVVEFG TFQTSGLSVIVHTLIYFTLVCILLLALQIHMYIG | *Arabidopsis thaliana* |
| XP_004306304.1 | 48 | MADWGPVLIAVALFVLLTPGLLFQLPGKSRVVEFN NMQTSGVSILVHTIIYFGLITIFLIAIGVHIYTGGGD | *Fragaria vesca* subsp. *vesca* |
| ACG32653.1 | 49 | MQDWAPVFVSLVLFILLSPGLLFQMPGKCRIIEFGNF QTSAISILVHAILEFALAAIFLVAVGVHMYLGS | *Zea mays* |
| XP_004297598.1 | 50 | MADWGPVIIAVVLFVLLTPGLLFQIPGKGRVVEFGN MQTSGASIVVHAIIYFGLLTIFLIAIGVHIYTG | *Fragaria vesca* subsp. *vesca* |
| XP_002455352.1 | 51 | MQDWAPVFISLVLFILLSPGLLFQMPGKCRIIEFGNF QTSAISILVHAILEFALAAIFLIAVGVHMYLGS | *Sorghum bicolor* |
| XP_006352171.1 | 52 | MSDWGPVLIAVVLFVLLSPGLLFQLPGRHKIVEFGN MQTSGLSILVHTVLYFGVITIFLIAIGVHIHTG | *Solanum tuberosum* |
| XP_006292430.1 | 53 | MPDWGPVFAVTLFVLLTPGLLIQIPGRGRVVEFGT FQTSGLSVIVHTLIYFTIVCILLLALQIHMYIG | *Capsella rubella* |
| KCW83143.1 | 54 | MADWGPVVIAVVLFVLLSPGLLFQIPGRHRVVEFGN METSGASILVHTIIYFGLITILLIAIGVHIYTG | *Eucalyptus grandis* |

TABLE 4-continued

HC1 homologs identified based on the HC1 poplar sequence.

| Accession No. | SEQ ID NO. | Sequence | Genus/Species |
|---|---|---|---|
| XP_007216168.1 | 55 | MADWGPVVIAVVLFVLLTPGLLFQLPGNSRVVEFN NMQTSGVSILVHTIIYFGLVTIFLIAIGVHIYTG | Prunus persica |
| XP_004503745.1 | 56 | MADWGPVIIAVVLFVLLSPGLLFQIPGRGRVIEFGN MQTSGASILVHAIIYFGLITILLIAIGVHIYTG | Cicer arietinum |
| XP_002304675.2 | 57 | SCNTFALPYINREFDIRAAVRRISIKHQHPEKKKEAM SDWGPVVIAVVLFVLLSPGLLFQLPGRNRVVEFGN MQTSALSILVHTIIFFGLITIFLIAIGVHIYTG | Populus trichocarpa |
| XP_002514896.1 | 58 | MADWGPVVIAVVLFVLLSPGLLFQLPGKGRVVEFG NMQTSGLSILVHTIIEFALVTIFLIAIGVHIYTG | Ricinus communis |
| XP_006493216.1 | 59 | MADWGPVVIATVLFVLLTPGLLFQIPGRNRVVEFGN MQTSGASILVHSVIEFGLITIFLIAITVHIYTG | Citrus sinensis |
| XP_002270842.1 | 60 | MSDWGAVFVSVMLFILLMPGLLIQIPGRGRFIEFTNF QTSGVSILVHSLIYFTLICIFLLAIGVHMCDIFEMADW APVLVGVVLFVLLSPGLLFQLPGHYRHVDFGGMKT NGKSIAVHTLIFVAIFAVLIMALHLHIYTG | Vitis vinifera |
| XP_004138041.1 | 61 | MADWGPVIIAVVLFVLLSPGLLFQIPAKGRVVEFGN MQTSGASILVHAIIYFGLITIFLIAIGVHIYTG | Cucumis sativus |
| XP_003631356.1 | 62 | MTDWGPVVATVLFVLLTPGLLCQIPGRGRVVEFG NMSTSGLSILVHAVIYFALVTIFVIAVSVHIYSGSG | Vitis vinifera |
| XP_002271098.1 | 63 | MADWGPVVIAVVLFVLLTPGLLFQLPGNNRVVEFG NMQTSRISILVHTIIYFGLITIFLIAIGVHIYTG | Vitis vinifera |
| EMS57713.1 | 64 | MADWAPVFIGLVLFILLSPGLLFQIPGKGRMVEFGN FQTSGISILVHAVIYFALIAILILAVNVHVFLG | Triticum urartu |
| XP_003553183.1 | 65 | MADWGPVVIAVVLFVLLSPGLLFQLPGRSRVVEFG NMQTSAISILVHTIIFFGLITIFLIAIGVHIYTG | Glycine max |
| KCW44914.1 | 66 | MKGGIRGWAEQGNGWFLSAVTNRAKPQKWSRRSR FKFKKKFTRRRRRRRKGRMADWGPVVIAVVLFVLL SPGLLFQIPGRHRVVEFGNMETSGASILVHTIIYFGLI TILLIAIGVHIYTG | Eucalyptus grandis |
| XP_003601753.1 | 67 | MADWGPVVIAVVLFVLLSPGLLFQMPGRNKVVEFG NMQTSGVSILVHTILFFGLITIFLIAIGVHINTG | Medicago truncatula |
| XP_007160023.1 | 68 | MADWGPVIIAVVLFVLLSPGLLFQIPSRGRIAEFGNM QTSGASILVHAVIYFGLITIFLIAIGVHIYTG | Phaseolus vulgaris |
| XP_002511164.1 | 69 | MADWGPVIIAVILFVLLTPGLLFQIPGRNRVVEFGN MHTSGASIVVHAIIYFGLITILLIAIGIHIYAG | Ricinus communis |
| XP_004502278.1 | 70 | MADWGPVVIAVVLFVLLSPGLLFQLPGRSRVVEFG NMQTSGVSILVHTIIFFGLITIFLIAIGVHINTG | Cicer arietinum |
| XP_004967908.1 | 71 | MQDWAPVFISLVLFILLSPGLLFQIPGKCRIIEFGNFH TSALSILVHAILYFALIAIFLIAIGVRMYLGS | Setaria italica |
| XP_007043959.1 | 72 | MNMFYSIFIVDFIGEFVFNLGSQAESWFCNSSTSATI MPLQEVNVCHLFVNSVGQSSRLQRKIGKSMADWGP VVIAVVLFVLLSPGLLFQLPGRSKVVEFGNMQTSGIS ILVHTIIFFGLITIFLIAIGVHIYTG | Theobroma cacao |
| XP_003525413.1 | 73 | MLTRLARRRSIRFRLSDFVYLCPPEALKLFSALKMA DWGPVVIAVVLFVLLSPGLLFQMPARGRVAEFGNM QTSGASILVHAIIYFGLITIFLIAIGVHIYTG | Glycine max |
| KCW61925.1 | 74 | MADWGPVVIAVVLFILLSPGLLFQLPGKMKAVEFG NMQTTGASILVHTIIEECLITIFLIAVGVHIYTG | Eucalyptus grandis |
| XP_002283942.1 | 75 | MADWAPILIGLLLFILLSPGLIFQLPGSVRHIEFGSFG TNGKAMLIHTILEEGIFTILIMALNIHIYLAESVMAD WGPVLIAVVLFVLLTPGLLFQVPGKNRVVEFGSMH TSGASILVHTIIYFGLITIFLIAIGVHIYTG | Vitis vinifera |

TABLE 4-continued

HC1 homologs identified based on the HC1 poplar sequence.

| Accession No. | SEQ ID NO. | Sequence | Genus/Species |
|---|---|---|---|
| XP_004231769.1 | 76 | MADWGPVVIAVVLFVLLSPGLLFQLPGNNRAVEFA<br>NFQTSGLSIFIHTILEEGLITIFLIAIGVHIYTG | Solanum lycopersicum |
| XP_006591443.1 | 77 | MADWGPVVIAVVLFVLLSPGLVFQLPGKSRVVEFG<br>NMQTSAVSILVHTIIEEGLITIFLVAIGVHIYTG | Glycine max |
| EYU42082.1 | 78 | MADWGPVVIAVVLFVLLSPGLLFQLPGRRVVEFG<br>NMQTSGLSILVHTVIEEGLITIFLIAIGVHIYAA | Erythranthe guttata |
| XP_006436859.1 | 79 | MADWGPVVIATVLFVLLTPGLLFQIPGRNRVVEFGN<br>MQTSGASILVHSVIEEGLITIFLIAITVHIYLADFLYPV<br>SSVSCCFYLFLVSTFLEFEKVFLFVL | Citrus clementina |
| XP_006395489.1 | 80 | MSDWGPVFVAVTLFVLLTPGVLIQIPGKNRVVEFGT<br>FQTSGVSVIVHTLIYFTLVCILLLALQIHIVIVKFLSFF<br>LLELCVNSLFCLAPLSKGVTFLPSHSQKTTTMADWA<br>PVLVGVILFVILSPGLLFSLPGNNRAVDFGTLKTNGK<br>AIAVHTLIEFAIYSILILAVNLHIYTG | Eutrema salsugineum |
| EMT04963.1 | 81 | MADWGPVIVATVLFVLLTPGLLCTLPGRGRVAEFG<br>SMHTSGLSILIHAVLYFALVTIFLIAVGVHVYTG | Aegilops tauschii |
| XP_006404231.1 | 82 | MADWGPVVAVILFVLLTPGLLFQIPARGRIVEFGN<br>MQTSGASILVHTIIYFGLITIFTIAIRLHIYTG | Eutrema salsugineum |
| XP_006438001.1 | 83 | MADWGPVVIAVVLFVLLSPGLLFQLPGRNRVVEFG<br>NMHTSGLSILVHTIIEEGLVTIFLIAIGVHIHTG | Citrus clementina |
| XP_006338707.1 | 84 | MADWGPVVIAVVLFVLLSPGLLFQLPGNNRVVQFA<br>NFQTSGLSIFIHTILEEGLITIFLIAIGVHIYTG | Solanum tuberosum |
| XP_007038005.1 | 85 | MKRSEIRKDPTQDNRSRWNHNTSSGESSHVRSLVSR<br>HPRSIQCERNPSRFVCILCPISFTLPSLFSSFLFPKPFSH<br>SRCTLLFLLEEIFILSGKNQKPQGRGQMADWGPVLV<br>ATVLFVLLSPGLLFQIPGRNKVVEFGNMQTSGASIL<br>VHAIIYFGLITIFCIAIGVHIYASQ | Theobroma cacao |
| XP_002321710.2 | 86 | MADWGPVIVAVVLFVLLTPGLLFQIPGKSRVVEFGN<br>MQTSGASIAVHAIVFSGLITIFLVAIGVHIYAAK | Populus trichocarpa |
| XP_004236928.1 | 87 | MLDWGPVLVSVILFILLSPGLLFQLPGHRHCVEFGN<br>FHTSGASIMIHTLLYFALVCVEELAVKVHLYLG | Solanum lycopersicum |
| XP_002439094.1 | 88 | MSDWGPVVIGLVLFVLLSPGLLIQLPGRHHFVEFGN<br>LQTSAVSILVHSIIYFALITIFVIVIGVHITTGN | Sorghum bicolor |
| NP_001052628.1 | 89 | MADWGPVVATVLFVLLTPGLLCTVPGRGRVAEFG<br>SFHTSGLAIIVHAVLYFALLTIFLIAIGVHIYAG | Oryza sativa Japonica Group |
| XP_007163777.1 | 90 | MADWGPVVIAVVLFVLLSPGLLFQLPGKNRVVEFG<br>KMQTSGVSILVHTIIFFGLITIFLIAIGVHINTG | Phaseolus vulgaris |
| EMS45275.1 | 91 | MADWGPVIVATVLFVLLTPGLLCTLPGRGRVAEFG<br>SMHTSGLSLLIHAVLYFALVTIFLIAVGVHVYTG | Triticum urartu |
| BAJ92955.1 | 92 | MADWGPVIVATVLFVLLTPGLLCTLPGRGRVAEFG<br>SMHTSGLSILIHAVLYFALVTIFIIAVGVHVYTG | Hordeum vulgare subsp. vulgare |
| CBI15682.3 | 93 | MGTGMGTFPDPASFFLEAESVMADWGPVLIAVVLF<br>VLLTPGLLFQVPGKNRVVEFGSMHTSGASILVHTIIY<br>FGLITIFLIAIGVHIYTDLQTLASICFKNRGNCMIRKP<br>VPHALKNRGLDDVNLWRSTPQLPTWHYP | Vitis vinifera |
| XP_007225875.1 | 94 | MADWGPVVIAVVLFVLLSPGLLFQLPGRGRVVEFG<br>SMHTSGISILVHTIIFFGLLTIFLIAIGVHIYTG | Prunus persica |
| XP_002276548.1 | 95 | MSADWGPIFVSVVLFVLLSPGLLFQLPGSNRCVEFG<br>NLRTSGASIMLHALLEFALICLFLLGFKIHLYIGS | Vitis vinifera |
| NP_190435.1 | 96 | MADWGPVVVAVILFVLLTPGLLFQIPARGRVVEFG<br>NMQTSGASILVHTIIFFGLITIFTIAIRLHIYTGTRQLA<br>LVWFIGIRVQIGIEY | Arabidopsis thaliana |

TABLE 4-continued

HC1 homologs identified based on the HC1 poplar sequence.

| Accession No. | SEQ ID NO. | Sequence | Genus/Species |
|---|---|---|---|
| XP_006594529.1 | 97 | MADWGPMVIAVVLFVLLSPGLLFQLPGKSKVVEFG NMQTRAVSILVHTIIFFGLITIFLVAIGVHIYTG | Glycine max |
| ACG41546.1 | 98 | MSDWGPVVIGLVLFVLLSPGLLVQLPGRHHLVEFG NLKTSAVSILVHSIIYFALITLFVIVIGVHITTGD | Zea mays |
| ACF80966.1 | 99 | MADWGPVIVATVLFVVLTPGLLCTLPGRGRVAEFG SMHTSGLAILVHAVLYFALITIFLIAIGIHVYAG | Zea mays |
| NP_189339.1 | 100 | MPDWGPVFVAVTLFVLLTPGLLIQVPGRGRVVEFG TFQTSGLSVIVHTLIYFTLVCILLLALQIHICNLFSTSM ADWAPVLVGVVLFVILSPGLLFSLPGNNRTVDFGGL KTNGKAIAVHTLIEFAIYTILILALNLHIYTG | Arabidopsis thaliana |
| XP_002877012.1 | 101 | MPDWGPVFVAVTLFVLLTPGLLIQVPGRGRVVEFG TFQTSGLSVIVHTLIYFTLVCILLLALQIHICNLFSTSM ADWAPVLVGVVLFVILSPGLLFSLPGNNRTVDFGGL KTNGKAIAVHTLIEFAIYSILILALNLHIYTG | Arabidopsis lyrata subsp. lyrata |
| EPS61900.1 | 102 | MADWGPVLIATVLFVLLTPGLLFQLPGRNRVVDFG TMHTSGLSILVHTVIYFGLITLLLVAVGVHIYAG | Genlisea aurea |
| XP_006292149.1 | 103 | MADWGPVVIAVILFVLLTPGLLFQIPARGRVVEFGN MQTSGASILVHTIIEFGLITIFTIAIRLHIYTG | Capsella rubella |
| EMT00249.1 | 104 | MADWAPVFIALVLFVLLSPGLLFQVPGKNRFLEFGN KQTSGVSVLFHAVIYFALIAIFTLAVRVHVILG | Aegilops tauschii |
| XP_003579615.1 | 105 | MADWGPVIVATVLFVLLTPGLLCTLPGRGRVAEFG SMHTTGLAILVHAVLYFALATIFLIAIGVHVYTG | Brachypodium distachyon |

REFERENCES

U.S. Pat. No. 4,761,373
U.S. Pat. No. 4,769,061
U.S. Pat. No. 4,810,648
U.S. Pat. No. 4,940,835
U.S. Pat. No. 4,975,374
U.S. Pat. No. 4,987,071
U.S. Pat. No. 5,013,659
U.S. Pat. No. 5,023,179
U.S. Pat. No. 5,034,322
U.S. Pat. No. 5,093,246
U.S. Pat. No. 5,106,739
U.S. Pat. No. 5,116,742
U.S. Pat. No. 5,162,602
U.S. Pat. No. 5,164,316
U.S. Pat. No. 5,196,525
U.S. Pat. No. 5,256,558
U.S. Pat. No. 5,276,268
U.S. Pat. No. 5,304,730
U.S. Pat. No. 5,322,938
U.S. Pat. No. 5,359,142
U.S. Pat. No. 5,424,200
U.S. Pat. No. 5,495,071
U.S. Pat. No. 5,554,798
U.S. Pat. No. 5,561,236
U.S. Pat. No. 5,569,823
U.S. Pat. No. 5,599,672
U.S. Pat. No. 5,625,136
U.S. Pat. No. 5,661,017
U.S. Pat. No. 5,723,763
U.S. Pat. No. 5,767,366
U.S. Pat. No. 5,879,903
U.S. Pat. No. 5,928,937
U.S. Pat. No. 6,084,155
U.S. Pat. No. 6,329,504
U.S. Pat. No. 6,337,431
U.S. Pat. No. 6,455,760
U.S. Pat. No. 6,696,623
U.S. Pat. No. 6,831,208
U.S. Pat. No. 7,723,575
U.S. Published Patent Application No. 20030084486
U.S. Published Patent Application No. 20030177536
U.S. Published Patent Application No. 20040019934
U.S. Published Patent Application No. 20040067506
U.S. Published Patent Application No. 20040078841
U.S. Published Patent Application No. 20040123349
U.S. Published Patent Application No. 20070006346
U.S. Published Patent Application No. 20080196125
U.S. Published Patent Application No. 20090031441
U.S. Published Patent Application No. 20090199307
PCT Patent Publication 2013/026740
EPO Application No. EP1528104
EPO Application No. EP0242246
Altschul, S. F. et al. (1997) "Gapped BLAST and PSI-BLAST: A New Generation of Protein Database Search Programs" *Nucl. Acids Res.* 25:3389-3402.
Bartel, D. and Szostak, J. W. (1993) *Science* 261:1411-1418.
Bassett, C. L., Callahan, A., Artlip, T., Scorza, R. Srinivasan, C. (2007) "A minimal peach type II chlorophyll a/b-binding protein promoter retains tissue-specificity and light regulation in tomato" *BMC Biotechnol.*, 7:47.
Bayer Research, vol. 24, pp. 68-71.
Beltz, G. A., Jacobs, K. A., Eickbush, T. H., Cherbas, P. T., Kafatos, F. C. (1983) "Isolation of multigene families and determination of homologies by filter hybridization methods" *Methods of Enzymology*, R. Wu, L. Grossman and K. Moldave [eds.] Academic Press, New York 100:266-285.

Benfrey et al. (1990) *EMBO J* 9:1677-1684.
Brusslan, J. A. and Tobin, E. M. (1992) "Light-independent developmental regulation of cab gene expression in *Arabidopsis thaliana* seedlings" *Proc Natl Acad Sci USA*, 89(16):7791-5.
Bustos et al. (1989) *Plant Cell*, 1:839-854.
Cai et al. (2009) *Plant Mol Biol* 69:699-709.
Chandler et al. (1989) "Two Regulatory Genes of the Maize Anthocyanin Pathway Are Homologous: Isolation of B Utilizing R Genomic Sequences" *The Plant Cell*, 1:1175-1183.
Chen et al. (2002) *J. Biol. Chem.* 277:13641-13649.
Chua et al. (2003) *Plant Cell* 15:11468-1479.
Chudalayandi, S. (2011) *Methods Mol. Biol.* 701:285-300.
Clancy, M. and Hannah, L.C. (2002) "Splicing of the maize Sh1 first intron is essential for enhancement of gene expression, and a T-rich motif increases expression without affecting splicing" *Plant Physiol.* 130(2):918-29.
Dale et al. (1995) *Plant J* 7:649-659.
de la Pena (1987) *Nature* 325:274-276.
Ebert et al. (1987) *Proc. Nat'l Acad. Sci. USA.* 84:5745-5749.
Feng, et al. *Cell Research* 23:1229-1232, 2013.
Funk, V., B. Kositsup, C. Zhao, and E. P. Beers. 2002. The *Arabidopsis xylem* peptidase XCP1 is a tracheary element vacuolar protein that may be a papain ortholog. *Plant Physiology*, 128:84-94.
Furtado, A. et al. (2002) "Tools for Use in the Genetic Engineering of Barley" *Proceedings of the 10th Australian Barley technical Symposium, Canberra, ACT, Australia.*
Green et al., *EMBO J.*, 7:4035-4044 (1988).
Haseloff and Gerlach (1988) *Nature* 334:585-591.
Hudspeth et al. (1989) *Plant Mol. Biol.*, 12:579-589.
Hwang, Y-S. et al. (2002) "Analysis of the Rice Endosperm-Specific Globulin Promoter in Transformed Rice Cells" *Plant Cell Rep.* 20:842-847.
Jordano et al., *Plant Cell*, 1:855-866 (1989).
Karlin S. and Altschul, S. F. (1990) "Methods for Assessing the Statistical Significance of Molecular Sequence Features by Using General Scoring Schemes" *Proc. Natl. Acad. Sci. USA* 87:2264-2268.
Karlin S. and Altschul, S. F. (1993) "Applications and Statistics for Multiple High-Scoring Segments in Molecular Sequences" *Proc. Natl. Acad. Sci. USA* 90:5873-5877.
Klein et al. (1993) *Biotechnology* 4:583-590.
Kwon et al. (1994) *Plant Physiol.* 105:357-67.
Lawton et al. (1987) *Plant Mol. Biol.* 9:315-324.
Lewin, B. (1985) *Genes II*, John Wiley & Sons, Inc., p. 96.
Li et al. (2009) *Plant Physiol* 151:1087-1095.
Lieberman-Lazarovich and Levy (2011) *Methods Mol Biol* 701: 51-65.
Lu, S., L. Laigene, Y. Xiaoping, C. P. Joshi, and V. L. Chiang. 2008. Differential expression of three *eucalyptus* secondary cell wall-related cellulose synthase genes in response to tension stress. *Journal of Experimental Botany*, pp. 1-15.
Lyznik et al. (2007) *Transgenic Plant J* 1:1-9.
Maniatis, T., E. F. Fritsch, J. Sambrook (1982) "Nuclease Bal31" *Molecular Cloning: A Laboratory Manual*, Cold Spring Harbor Laboratory, Cold Spring Harbor, N.Y.
Matsuoka et al. (1993) "Tissue-specific light—regulated expression directed by the promoter of a C4 gene, maize pyruvate, orthophosphate dikinase, in a C3 plant, rice" *PNAS USA*, 90(20):9586-90.
Matsuoka et al. (1994) *Plant J.* 6:311-319.
Meier et al. (1991) *Plant Cell*, 3:309-316.
Nagel et al. (1990) *Microbiol. Lett.* 67:325.
Odell et al. (1985) *Nature* 313:810-812.
Podevin, et al. *Trends Biotechnology*, online publication, 2013.
Puchta, H. (2002) *Plant Mol Biol* 48:173-182.
Richins et al. (1987) *Nucleic Acids Res.* 20:8451.
Sibout, R., A. Eudes, G. Mouille, B. Pollet, C. Lapierre, L. Jouanin, and A. Seguin. 2005. CINNAMYL ALCOHOL DEHYDROGENASE-C and -D are the primary genes involved in lignin biosynthesis in the floral stem of Arabidopsis. *The Plant Cell*, 17:2059-2076.
Song, J. Y., S. F. Lu, Z. Z. Chen, R. Lourenco, and V. L. Chiang. 2006. Genetic transformation of *Populus trichocarpa* genotype Nisqually-1: A functional genomic tool for woody plants. *Plant Cell Physiol.* 47: 1582-1589.
Sullivan et al. (1989) "Isolation and characterization of a maize chlorophyll a/b binding protein gene that produces high levels of mRNA in the dark" *Mol. Gen. Genet.*, 215(3):431-440.
Walker et al. (1987) *Proc. Nat'l Acad. Sci. USA*, 84:6624-6628.
Wang et al. (1992) "Characterization of cis-Acting Elements Regulating Transcription from the Promoter of a Constitutively Active Rice Actin Gene" *Molecular and Cellular Biology*, 12(8):3399-3406.
Wei et al., *J Gen Genomics*, 2013.
Wright et al. (2005) *Plant J* 44:693-705.
Wu, C-L. et al. (1998) "Promoters of Rice Seed Storage Protein Genes Direct Endosperm-Specific Gene Expression in Transgenic Rice" *Plant and Cell Physiology*, 39(8):885-889.
Xu, D., McElroy, D., Thornburg, R. W., Wu, R. et al. (1993) "Systemic induction of a potato pin2 promoter by wounding, methyl jasmonate, and abscisic acid in transgenic rice plants" *Plant Molecular Biology* 22:573-588.
Yau et al. *Plant J* (2011) 701:147-166.
Yamamoto et al. (1994) *Plant Cell Physiol.* 35:773-778.
Yamamoto et al. (1997) *Plant J.* 12(2):255-265.
Yang et al. (1990) *Proc. Nat'l Acad. Sci. USA*, 87:4144-4148.
Zhang et al. (1996) *Plant Physiology*, 110:1069-1079.
Zhang et al., *Plant Physiol.*, 2012.
www.lifesci.sussex.ac.uk/home/Neil_Crickmore/Bt/

What is claimed is:

1. A method for increasing growth rate, yield, and/or resistance to drought conditions in a plant, comprising expressing in said plant a polynucleotide comprising a nucleotide sequence encoding a polypeptide having at least 95% sequence identity to the amino acid sequence of SEQ ID NO:10, wherein said expressing increases growth rate, yield, and/or resistance to drought conditions in the plant relative to a plant wherein the polynucleotide has not been introduced, and wherein the polynucleotide is operably linked to a heterologous regulatory element.

2. The method according to claim 1, wherein said plant is of the genus *Abies, Acacia, Acer, Aegilops, Aesculus, Ailanthus, Alnus, Amborella, Amelanchier, Arabidopsis, Arbutus, Arctostaphylos, Artemisia, Asiminia, Atriplex, Aucuba, Berberis, Betula, Brachypodium, Buddleia, Buxus, Calocedrus, Camellia, Campsis, Capsella, Carpinus, Carya, Castanea, Catalpa, Ceanothus, Cedrus, Celastrus, Celtis, Cephalan-* thus, Cercidium, Cercis, Chaenomeles, Chamaecyparis, Chilopsis, Chionanthus, Chrysothamnus, Cicer, Cistus, Citrus, Cladrastis, Clematis, Coleogynia, Cornus, Corylus, Cotinus, Cotoneaster, Cowania, Crataegus, Crataegus, Cucumis, Cupressus, Cytisus, Daphne, Deutzia, Diospyros, Elaeagnus, Ephedra, Erythranthe, Escallonia, Eucalyptus, Euonymus, Eutrema, Fagus, Forsythia, Fragaria, Fraxinus, Gaultheria, Genlisea, Ginkgo, Gleditsia, Glycine, Grevillea, Gymnocladus, Hamamelis, Hebe, Hibiscus, Hordeum, Hydrangea, Hypericum, Ilex, Juglans, Juniperus, Kalmia, Kerria, Koelreuteria, Lagerstroemia, Larix, Larrea, Libocedrus, Ligustrum, Liquidambar, Liriodendron, Lonicera, Lotus, Maclura, Magnolia, Mahonia, Malus, Medicago, Menispermum, Morus, Myrica, Nyssa, Oryza, Osmanthus, Ostrya, Oxydendron, Parthenocissus, Phaseolus, Philadelphus, Photinia, Physocarpus, Picea, Pinus, Pittosporum, Platanus, Populus, Prosopis, Prunus, Pseudotsuga, Ptelea, Purshia, Pyrus, Quercus, Rhamnus, Rhaphiolepis, Rhododendron, Rhus, Ribes, Ricinus, Robinia, Rosa, Rubus, Salix, Sambucus, Sassafras, Sequoia, Setaria, Shepherdia, Smilax, Solanum, Sophora, Sorbus, Sorghum, Spiraea, Staphylea, Stewartia, Symphoricarpos, Syringa, Taxodium, Taxus, Theobroma, Thuja, Tilia, Triticum, Tsuga, Ulmus, Umbellularia, Vaccinium, Viburnum, Vitis, Zanthoxylum, Zea, or Zelkova.

3. The method according to claim 1, wherein said polynucleotide is stably incorporated into the genome of said plant.

4. The method according to claim 1, wherein the heterologous regulatory element has been inserted into the genome of said plant.

5. The method of claim 1, wherein said heterologous regulatory element is a promoter.

6. The method of claim 5, wherein said promoter is inserted into the plant genome within about 2 kbp of said polynucleotide.

7. The method of claim 5, wherein said promoter is a cauliflower mosaic virus 35S promoter, an enhanced CaMV 35S promoter, a CaMV 19S promoter, a cassava vein mosaic virus promoter, a prolifera promoter, an Ap3 promoter, a heat shock promoter, a T-DNA 1'- or 2'-promoter of A. tumefaciens, a polygalacturonase promoter, achalcone synthase A (CHS-A) promoter, a PR-1α promoter, a ubiquitin promoter, an actin promoter, an alcA gene promoter, a pin2 promoter, a maize WipI promoter, a maize trpA gene promoter, a maize CDPK gene promoter, a RUBISCO SSU promoter, a Cald5H promoter, a SAD promoter, a XCP1 promoter, a CAD promoter, a CesA1 promoter, a CesA2 promoter, a CesA3 promoter, a tubulin gene (TUB) promoter, a lipid transfer protein gene (LTP) promoter, a coumarate-4-hydroxylase gene (C4H) promoter, a Cab1 promoter, a Cab19 promoter, a PPDK promoter, a ribulose biphosphate carboxylase (RBCS) promoter, an Act1 promoter, an AS-1 promoter, a RBC-3A promoter, a Figwort Mosaic Virus (FMV) promoter, a mannopine synthase (mas) promoter, an octopine synthase (ocs) promoter, a nos promoter, an Adh promoter, a sucrose synthase promoter, an α-tubulin promoter, an actin promoter, a cab promoter, a PEPCase promoter, a promoter associated with a R gene complex, a 4-coumarate Co-enzyme A ligase (4CL) promoter, a β-phaseolin promoter, a glycinin promoter, or a MEG1 promoter.

8. The method of claim 1, wherein said heterologous regulatory element is an enhancer.

9. The method of claim 8, wherein said enhancer is a CaMV 35S enhancer, a SV40 enhancer, a maize shrunken-1 enhancer, a PetE enhancer, or a rice α-amylase enhancer.

10. A transformed or transgenic plant, plant tissue, or plant cell having increased growth rate, yield, and/or resistance to drought conditions, wherein said plant, plant tissue, or plant cell comprises a polynucleotide that comprises a nucleotide sequence encoding a polypeptide having at least 95% sequence identity to the amino acid sequence of SEQ ID NO:10, wherein said polypeptide increases growth rate, yield, and/or resistance to drought conditions in said plant plant tissue or plant cell relative to a plant, plant tissue or plant cell wherein said polynucleotide has not been introduced, and wherein the polynucleotide is operably linked to a heterologous regulatory element.

11. The transformed or transgenic plant, plant tissue, or plant cell according to claim 10, wherein said plant is of the genus Abies, Acacia, Acer, Aegilops, Aesculus, Ailanthus, Alnus, Amborella, Amelanchier, Arabidopsis, Arbutus, Arctostaphylos, Artemisia, Asiminia, Atriplex, Aucuba, Berberis, Betula, Brachypodium, Buddleia, Buxus, Calocedrus, Camellia, Campsis, Capsella, Carpinus, Carya, Castanea, Catalpa, Ceanothus, Cedrus, Celastrus, Celtis, Cephalanthus, Cercidium, Cercis, Chaenomeles, Chamaecyparis, Chilopsis, Chionanthus, Chrysothamnus, Cicer, Cistus, Citrus, Cladrastis, Clematis, Coleogynia, Cornus, Corylus, Cotinus, Cotoneaster, Cowania, Crataegus, Crataegus, Cucumis, Cupressus, Cytisus, Daphne, Deutzia, Diospyros, Elaeagnus, Ephedra, Erythranthe, Escallonia, Eucalyptus, Euonymus, Eutrema, Fagus, Forsythia, Fragaria, Fraxinus, Gaultheria, Genlisea, Ginkgo, Gleditsia, Glycine, Grevillea, Gymnocladus, Hamamelis, Hebe, Hibiscus, Hordeum, Hydrangea, Hypericum, Ilex, Juglans, Juniperus, Kalmia, Kerria, Koelreuteria, Lagerstroemia, Larix, Larrea, Libocedrus, Ligustrum, Liquidambar, Liriodendron, Lonicera, Lotus, Maclura, Magnolia, Mahonia, Malus, Medicago, Menispermum, Morus, Myrica, Nyssa, Oryza, Osmanthus, Ostrya, Oxydendron, Parthenocissus, Phaseolus, Philadelphus, Photinia, Physocarpus, Picea, Pinus, Pittosporum, Platanus, Populus, Prosopis, Prunus, Pseudotsuga, Ptelea, Purshia, Pyrus, Quercus, Rhamnus, Rhaphiolepis, Rhododendron, Rhus, Ribes, Ricinus, Robinia, Rosa, Rubus, Salix, Sambucus, Sassafras, Sequoia, Setaria, Shepherdia, Smilax, Solanum, Sophora, Sorbus, Sorghum, Spiraea, Staphylea, Stewartia, Symphoricarpos, Syringa, Taxodium, Taxus, Theobroma, Thuja, Tilia, Triticum, Tsuga, Ulmus, Umbellularia, Vaccinium, Viburnum, Vitis, Zanthoxylum, Zea, or Zelkova.

12. The transformed or transgenic plant, plant tissue, or plant cell according to claim 10, wherein said polynucleotide is stably incorporated into the genome of said transformed or transgenic plant, plant tissue, or plant cell.

13. The transformed or transgenic plant, plant tissue, or plant cell according to claim 10, wherein the heterologous regulatory element has been inserted into the genome of said transformed or transgenic plant, plant tissue, or plant cell.

14. The transformed or transgenic plant, plant tissue, or plant cell according to claim 13, wherein said heterologous regulatory element is a promoter.

15. The transformed or transgenic plant, plant tissue, or plant cell according to claim 14, wherein said promoter is inserted into the plant genome within about 2 kbp of said polynucleotide.

16. The transformed or transgenic plant, plant tissue, or plant cell according to claim 15, wherein said promoter is cauliflower mosaic virus 35S promoter, an enhanced CaMV 35S promoter, a CaMV 19S promoter, a cassava vein mosaic virus promoter, a prolifera promoter, an Ap3 promoter, a heat shock promoter, a T-DNA 1'- or 2'-promoter of A. tumefaciens, a polygalacturonase promoter, achalcone synthase A (CHS-A) promoter, a PR-1α promoter, a ubiquitin promoter, an actin promoter, an alcA gene promoter, a pin2 promoter, a maize WipI promoter, a maize trpA gene promoter, a maize CDPK gene promoter, a RUBISCO SSU promoter, a Cald5H promoter, a SAD promoter, a XCP1 promoter, a CAD promoter, a CesA1 promoter, a CesA2 promoter, a CesA3 promoter, a tubulin gene (TUB) promoter, a lipid transfer protein gene (LTP) promoter, a coumarate-4-hydroxylase gene (C4H) promoter, a Cab1 promoter, a Cab19 promoter, a PPDK promoter, a ribulose biphosphate carboxylase (RBCS) promoter, an Act1 promoter, an AS-1 promoter, a RBC-3A promoter, a Figwort Mosaic Virus (FMV) promoter, a mannopine synthase (mas) promoter, an octopine synthase (ocs) promoter, a nos promoter, an Adh promoter, a sucrose synthase promoter, an α-tubulin promoter, an actin promoter, a cab promoter, a PEPCase promoter, a promoter associated with a R gene complex, a 4-coumarate Co-enzyme A ligase (4CL) promoter, a β-phaseolin promoter, a glycinin promoter, or a MEG1 promoter.

17. The transformed or transgenic plant, plant tissue, or plant cell according to claim 13, wherein said heterologous regulatory element is an enhancer.

18. The transformed or transgenic plant, plant tissue, or plant cell according to claim 17, wherein said enhancer is a CaMV 35S enhancer, a SV40 enhancer, a maize shrunken-1 enhancer, a PetE enhancer, or a rice α-amylase enhancer.

19. A method for preparing a transformed or transgenic plant, plant tissue, or plant cell having increased growth rate, yield, and/or resistance to drought conditions comprising incorporating a polynucleotide in a cell of said plant, wherein said polynucleotide comprises a nucleotide sequence encoding a polypeptide having at least 95% sequence identity to the amino acid sequence of SEQ ID NO:10, wherein said polypeptide increases growth rate, yield, and/or resistance to drought conditions in said plant, plant tissue or plant cell relative to a plant, plant tissue or plant cell wherein said polynucleotide has not been introduced, and wherein the polynucleotide is linked to a heterologous regulatory element.

20. The method according to claim 19, wherein said plant is of the genus *Abies, Acacia, Acer, Aegilops, Aesculus, Ailanthus, Alnus, Amborella, Amelanchier, Arabidopsis, Arbutus, Arctostaphylos, Artemisia, Asiminia, Atriplex, Aucuba, Berberis, Betula, Brachypodium, Buddleia, Buxus, Calocedrus, Camellia, Campsis, Capsella, Carpinus, Carya, Castanea, Catalpa, Ceanothus, Cedrus, Celastrus, Celtis, Cephalanthus, Cercidium, Cercis, Chaenomeles, Chamaecyparis, Chilopsis, Chionanthus, Chrysothamnus, Cicer, Cistus, Citrus, Cladrastis, Clematis, Coleogynia, Cornus, Corylus, Cotinus, Cotoneaster, Cowania, Crataegus, Crataegus, Cucumis, Cupressus, Cytisus, Daphne, Deutzia, Diospyros, Elaeagnus, Ephedra, Erythranthe, Escallonia, Eucalyptus, Euonymus, Eutrema, Fagus, Forsythia, Fragaria, Fraxinus, Gaultheria, Genlisea, Ginkgo, Gleditsia, Glycine, Grevillea, Gymnocladus, Hamamelis, Hebe, Hibiscus, Hordeum, Hydrangea, Hypericum, Ilex, Juglans, Juniperus, Kalmia, Kerria, Koelreuteria, Lagerstroemia, Larix, Larrea, Libocedrus, Ligustrum, Liquidambar, Liriodendron, Lonicera, Lotus, Maclura, Magnolia, Mahonia, Malus, Medicago, Menispermum, Morus, Myrica, Nyssa, Oryza, Osmanthus, Ostrya, Oxydendron, Parthenocissus, Phaseolus, Philadelphus, Photinia, Physocarpus, Picea, Pinus, Pittosporum, Platanus, Populus, Prosopis, Prunus, Pseudotsuga, Ptelea, Purshia, Pyrus, Quercus, Rhamnus, Rhaphiolepis, Rhododendron, Rhus, Ribes, Ricinus, Robinia, Rosa, Rubus, Salix, Sambucus, Sassafras, Sequoia, Setaria, Shepherdia, Smilax, Solanum, Sophora, Sorbus, Sorghum, Spiraea, Staphylea, Stewartia, Symphoricarpos, Syringa, Taxodium, Taxus, Theobroma, Thuja, Tilia, Triticum, Tsuga, Ulmus, Umbellularia, Vaccinium, Viburnum, Vitis, Zanthoxylum, Zea,* or *Zelkova.*

21. The method according to claim 19, wherein said polynucleotide is stably incorporated into the genome of said plant.

22. The method according to claim 19, wherein said heterologous regulatory element has been inserted into the genome of said plant.

23. The method of claim 22, wherein said heterologous regulatory element is a promoter.

24. The method of claim 23, wherein said promoter is inserted into the plant genome within about 2 kbp of said polynucleotide.

25. The method of claim 24, wherein said promoter is a cauliflower mosaic virus 35S promoter, an enhanced CaMV 35S promoter, a CaMV 19S promoter, a cassava vein mosaic virus promoter, a prolifera promoter, an Ap3 promoter, a heat shock promoter, a T-DNA 1'- or 2'-promoter of *A. tumefaciens,* a polygalacturonase promoter, achalcone synthase A (CHS-A) promoter, a PR-1α promoter, a ubiquitin promoter, an actin promoter, an alcA gene promoter, a pin2 promoter, a maize WipI promoter, a maize trpA gene promoter, a maize CDPK gene promoter, a RUBISCO SSU promoter, a Cald5H promoter, a SAD promoter, a XCP1 promoter, a CAD promoter, a CesA1 promoter, a CesA2 promoter, a CesA3 promoter, a tubulin gene (TUB) promoter, a lipid transfer protein gene (LTP) promoter, a coumarate-4-hydroxylase gene (C4H) promoter, a Cab1 promoter, a Cab19 promoter, a PPDK promoter, a ribulose biphosphate carboxylase (RBCS) promoter, an Act1 promoter, an AS-1 promoter, a RBC-3A promoter, a Figwort Mosaic Virus (FMV) promoter, a mannopine synthase (mas) promoter, an octopine synthase (ocs) promoter, a nos promoter, an Adh promoter, a sucrose synthase promoter, an α-tubulin promoter, an actin promoter, a cab promoter, a PEPCase promoter, a promoter associated with a R gene complex, a 4-coumarate Co-enzyme A ligase (4CL) promoter, a β-phaseolin promoter, a glycinin promoter, or a MEG1 promoter.

26. The method of claim 22, wherein said heterologous regulatory element is an enhancer.

27. The method of claim 26, wherein said enhancer is a CaMV 35S enhancer, a SV40 enhancer, a maize shrunken-1 enhancer, a PetE enhancer, or a rice α-amylase enhancer.

28. The method of claim 1, wherein said polypeptide comprises SEQ ID NO:10.

29. The transformed or transgenic plant of claim 10, wherein said polypeptide comprises SEQ ID NO:10.

30. The method of claim 19, wherein said polypeptide comprises SEQ ID NO:10.

\* \* \* \* \*